US008268773B2

(12) United States Patent
Presnell et al.

(10) Patent No.: US 8,268,773 B2
(45) Date of Patent: Sep. 18, 2012

(54) METHODS OF TREATING MULTIPLE SCLEROSIS (MS) USING AN IL-17A AND IL-17F ANTAGONIST

(75) Inventors: Scott R. Presnell, Tacoma, WA (US); Steven K. Burkhead, Hershey, PA (US); Steven D. Levin, Seattle, WA (US); Rolf E. Kuestner, Bothell, WA (US); Zeren Gao, Redmond, WA (US); Stephen R. Jaspers, Brewster, NY (US); Janine Bilsborough, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/015,304

(22) Filed: Jan. 27, 2011

(65) Prior Publication Data
US 2011/0177083 A1 Jul. 21, 2011

Related U.S. Application Data

(62) Division of application No. 11/150,533, filed on Jun. 10, 2005, now Pat. No. 7,910,540.

(60) Provisional application No. 60/578,805, filed on Jun. 10, 2004.

(51) Int. Cl.
A61K 38/00 (2006.01)

(52) U.S. Cl. .............. 514/1.1; 424/130.1; 424/134.1; 530/350; 530/351

(58) Field of Classification Search .................. None
See application file for complete search history.

(56) References Cited

U.S. PATENT DOCUMENTS

| 5,684,032 | A | 11/1997 | Elliot et al. |
| 6,569,645 | B2 | 5/2003 | Chen et al. |
| 6,579,520 | B2 | 6/2003 | Chen et al. |
| 7,115,398 | B2 | 10/2006 | Chen et al. |
| 7,247,442 | B1 | 7/2007 | Ruben et al. |
| 7,619,071 | B2 | 11/2009 | Presnell et al. |
| 7,622,116 | B2 | 11/2009 | Kuestner et al. |
| 7,790,676 | B2 | 9/2010 | Levin et al. |
| 7,842,665 | B2 | 11/2010 | Levin et al. |
| 7,910,540 | B2 | 3/2011 | Levin et al. |
| 7,910,701 | B2 | 3/2011 | Presnell et al. |
| 8,084,231 | B2 | 12/2011 | Levin et al. |
| 8,093,355 | B2 | 1/2012 | Kuestner et al. |
| 2002/0119130 | A1 | 8/2002 | Eaton et al. |
| 2002/0177188 | A1 | 11/2002 | Chen et al. |
| 2002/0182673 | A1 | 12/2002 | Chen et al. |
| 2003/0008815 | A1 | 1/2003 | Chen et al. |
| 2003/0040471 | A1 | 2/2003 | Watson et al. |
| 2003/0046196 | A1 | 3/2003 | Kelly |
| 2003/0073623 | A1 | 4/2003 | Drmanac et al. |
| 2003/0092881 | A1 | 5/2003 | Gorman |
| 2003/0100051 | A1 | 5/2003 | Ruben et al. |
| 2003/0180857 | A1 | 9/2003 | Eaton et al. |
| 2003/0181669 | A1 | 9/2003 | Eaton et al. |
| 2003/0199041 | A1 | 10/2003 | Presnell et al. |
| 2004/0009479 | A1 | 1/2004 | Wohlgemuth et al. |
| 2004/0048249 | A1 | 3/2004 | Tang et al. |
| 2004/0091959 | A1 | 5/2004 | Baker et al. |
| 2004/0097447 | A1 | 5/2004 | Dobie |
| 2006/0002925 | A1 | 1/2006 | Presnell et al. |
| 2007/0036763 | A1 | 2/2007 | Presnell et al. |
| 2007/0036791 | A1 | 2/2007 | Presnell et al. |
| 2007/0037968 | A1 | 2/2007 | Presnell et al. |
| 2007/0048257 | A1 | 3/2007 | Presnell et al. |
| 2007/0048824 | A1 | 3/2007 | Presnell et al. |
| 2007/0048826 | A1 | 3/2007 | Presnell et al. |
| 2007/0238658 | A1 | 10/2007 | Levin et al. |
| 2007/0249533 | A1 | 10/2007 | Levin et al. |

FOREIGN PATENT DOCUMENTS

| WO | WO 96/29408 | 9/1996 |
| WO | WO 98/37193 | 8/1998 |
| WO | WO 98/49307 | 11/1998 |
| WO | WO 99/07848 | 2/1999 |
| WO | WO 99/14240 | 3/1999 |
| WO | WO 99/58660 | 11/1999 |
| WO | WO 01/04304 | 1/2001 |
| WO | WO 01/46420 | 6/2001 |
| WO | 01/66722 A1 | 9/2001 |
| WO | 01/90358 A2 | 11/2001 |
| WO | WO 01/90357 | 11/2001 |
| WO | 02/04519 A2 | 1/2002 |
| WO | WO 02/38764 | 5/2002 |
| WO | 2005/010044 A2 | 2/2005 |

(Continued)

OTHER PUBLICATIONS

Haak et al. IL-17A and IL-17F do not contribute vitally to autoimmune neuro-inflammation in mice. J Clin Invest. Jan. 2009;119(1):61-9.*
Aggarwal et al., J. Biol. Chem. 278(3): 1910-1914, 2003.
Le Grand et al., Arthritis Rheum. 44(9): 2078-2083, 2001.
Barczyk et al., Respir. Med. 97: 726-733, 2003.
Cai et al., Cytokine 16(1): 10-21, Oct. 2001.
Chabaud et al., Arthritis Rheum. 42(5): 963-970, May 1999.
Dumont, Expert Opin. Ther. Patents 13(3): 287-303, 2003.
Fossiez et al., J. Exp. Med. 183: 2593-2603, Jun. 1996.
Fossiez et al., Int. Rev. Immunol. 16: 541-551, 1998.
Gerritsen et al., Br. J. Pharmacol. 140(4): 595-610, 2003.
Haudenschild et al., J. Biol. Chem. 277(6): 4309-4316, 2002.
Hellings et al., Am. J. Respir. Cell Mol. Biol. 28: 42-50, 2003.
Hurst et al., J. Immunol. 169: 443-453, 2002.
Hymowitz et al., EMBO J. 20(19): 5332-5341, 2001.
Ivanov et al., European Respiratory Journal 22(44 (Supple): 42s, 2003.

(Continued)

Primary Examiner — Dong Jiang
(74) Attorney, Agent, or Firm — Nelson Mullins Riley & Scarborough LLP; Jane E. Remillard, Esq.; Jill Gorny Sloper, Esq.

(57) ABSTRACT

The present invention relates to blocking, inhibiting, reducing, antagonizing or neutralizing the activity of IL-17F, IL-17A, or both IL-17A and IL-17F polypeptide molecules. IL-17A and IL-17F are cytokines that are involved in inflammatory processes and human disease. ZcytoR14 is a common receptor for IL-17A and IL-17F. The present invention includes soluble ZcytoR14, anti-ZcytoR14 antibodies and binding partners, as well as methods for antagonizing IL-17F, IL-17A or both IL-17A and IL-17F using such soluble receptors, antibodies and binding partners.

6 Claims, No Drawings

FOREIGN PATENT DOCUMENTS

| | | |
|---|---|---|
| WO | 2005/065711 A2 | 7/2005 |
| WO | 2006/088833 A2 | 8/2006 |
| WO | 2007/038703 A2 | 4/2007 |

OTHER PUBLICATIONS

Jovanovic et al., *J. Immunol. 160*: 3513-3521, 1998.
Kawaguchi et al., *J. Immunol. 167*: 4430-4435, 2001.
Kotake et al., *J. Clin. Invest. 103*: 1345-1352, 1999.
Laan et al., *Eur. Respir. J. 21*: 387-393, 2003.
Linden et al., *Eur. Respir. J. 15*: 973-977, 2000.
Novatchkova et al., *Trends Biochem. Sci. 28*(5): 226-229, May 2003.
Oda et al., *Am. J. Respir. Crit. Care Med. 171*: 12-18, 2005.
Pellagatti et al., *Br. J. Haematol. 125*(5): 576-83, 2004.
GenBank, Accession No. AV010326, May 10, 1999.
UniProt Database, Accession No. Q8K4X1, Oct. 2002.
UniProt Database, Accession No. Q8N2D7, Oct. 2002.
UniProt Database, Accession No. Q8BPI5, Mar. 2003.
Starnes et al. *J. Immunol. 167*: 4137-4140, 2001.
Tian et al., *Oncogene 19*(17): 2098-2109, 2000.
Tsibris et al., *Biochem. Biophys. Res. Commun. 312*(1): 249-254, 2003.
Van Bezooijen et al., *J. Bone Miner. Res. 14*(9): 1513-1521, 1999.
Yan et al., *Science 290*(20):523-527, Oct. 2000.
Yao et al., *Immunity 3*(6):811-821, Dec. 1995.
Yao et al., *J. Immunol. 155*: 5483-5486, 1995.
Yao et al., *Cytokine 9*(11): 794-800, Nov. 1997.
Ye et al., *Am. J. Respir. Cell Mol. Biol. 25*: 335-340, 2001
Database EMBL Online! EBI; Accession No. Al261248, Nov. 16, 1998.
Database EMBL Online! EBI; Accession No. AL133097, Feb. 18, 2002.
Albanesi, Cristina et al., "IL-17 Is Produced by Nickel-Specific T Lymphocytes and Regulates ICAM-1 Expression and Chemokine Production in Human Keratinocytes: Synergistic or Antagonist Effects with IFN-gamma dn TNF-alpha," The Journal of Immunology, vol. 162:494-502 (1999).
Antonysamy, Mary A. et al., "Evidence for a Role of IL-17 in Organ Allograft Rejection: IL-17 Promotes the Functional Differentiation of Dendritic Cell Progenitors," The Journal of Immunology, vol. 162:577-584 (1999).
Fujino, S. et al., "Increased expression of interleukin 17 in inflammatory bowel disease," Gut, vol. 52:65-70 (2003).
Kurasawa, Kazuhiro et al., "Increased Interleukin-17 Production in Patients with Systemic Sclerosis," Arthritis & Rheumatism, vol. 43(11):2455-2463 (2000).
Linden, Anders, "Role of Interleukin-17 and the Neutrophil in Asthma," Int. Arch. Allergy Immunol., vol. 126:179-184 (2001).
Loong, Che-Chuan et al., "Evidence for the early involvement of interleukin 17 in human and experimental renal allograft rejection," Journal of Pathology, vol. 197:322-332 (2002).
Lubberts, Erik, "The role of IL-17 and family members in the pathogenesis of arthritis," Current Opinion in Investigational Drugs, vol. 4(5):572-577 (2003).
Matusevicius, D. et al., "Interleukin-17 mRNA expression in blood and CSF mononuclear cells is augmented in multiple sclerosis," Multiple Sclerosis, vol. 5:101-104 (1999).
Molet, Sophie et al., "IL-17 is increased in asthmatic airways and induces human bronchial fibroblasts to produce cytokines," J. Allergy Clin. Immunol., vol. 108(3):430-438 (2001).
Moseley, T.A. et al., "Interleukin-17 family and IL-17 receptors," Cytokine & Growth Factor Reviews, vol. 14:155-174 (2003).
Nakae, Susumu et al., "Suppression of Immune Induction of Collagen-Induced Arthritis in IL-17-Deficient Mice," The Journal of Immunology, vol. 171:6173-6177 (2003).
Rahman, M.S. et al., "IL-17R activation of human airway smooth muscle cells induces CXCL-8 production via a transcriptional-dependent mechanism," Clinical Immunology, vol. 115:268-276 (2005).
Rouvier, Eric et al., "CTLA-8, Cloned from an Activated T Cell, Bearing AU-Rich Messenger RNA Instability Sequences, and Homologous to a Herpesvirus Saimiri Gene," The Journal of Immunology, vol. 150(12):5445-5456 (1993).
Shalom-Barak, Tali et al., "Interleukin-17-induced Gene Expression in Articular Chondrocytes is Associated with Activation of Mitogen-activated Protein Kinases and NF-kB," The Journal of Biological Chemistry, vol. 273 (42):27467-27473 (1998).
Teunissen, Marcel B.M. et al., "Interleukin-17 and Interferon-gamma Synergize in the Enhancement of Proinflammatory Cytokine Production by Human Keratinocytes," J. Invest. Dermatol., vol. 111:645-649 (1998).
Haudenschild, Dominik R. et al., "Generation of Interleukin-17 Receptor-Like Protein (IL-17RL) in Prostate by Alternative Splicing of RNA," The Prostate, vol. 66:1268-1274 (2006).
Incyte Corporation Accession No. LIN1878466F6 (1997).
Incyte Pharmaceuticals, Inc. Sequence INC5424219.
Kramer, Jill M. et al., "Cutting Edge: Evidence for Ligand-Independent Multimerization of the IL-17 Receptor," The Journal of Immunology, vol. 176:711-715 (2006).
Parnet, Patricia et al., "IL-1Rrp Is a Novel Receptor-like Molecule Similar to the Type I Interleukin-1 Receptor and Its Homologues T1/ST2 and IL-1R AcP," The Journal of Biological Chemistry, vol. 271(8):3967-3970 (1996).
TIGR Tentative Human Consensus Accession No. THC__ THC160674 (1997).
Vukicevic, Slobodan et al., "Induction of nephrogenic mesenchyme by osteogenic protein 1 (bone morphogenetic protein 7)," Proc. Natl. Acad. Sci. USA, vol. 93:9021-9026 (1996).
Yan, Minhong et al., "Two-Amino Acid Molecular Switch in an Epithelial Morphogen That Regulates Binding to Two District Receptors," Science, vol. 290:523-527 (2000).
Zabarovsky, E. et al., "Shot-gun sequencing strategy for long range genome mapping: first results," Accession No. Z22374 (1995).
International Preliminary Report on Patentability and Written Opinion for Application No. PCT/US2005/020521, 7 pages, dated Dec. 14, 2006.
International Search Report for Application No. PCT/US2005/020521, 4 pages, dated Jan. 2, 2006.

\* cited by examiner

METHODS OF TREATING MULTIPLE SCLEROSIS (MS) USING AN IL-17A AND IL-17F ANTAGONIST

REFERENCE TO RELATED INVENTIONS

This application is a divisional of U.S. application Ser. No. 11/150,533, filed Jun. 10, 2005, which claims the benefit of U.S. Provisional Application Ser. No. 60/578,805, filed Jun. 10, 2004, both of which are incorporated herein by reference.

BACKGROUND OF THE INVENTION

Cytokines are soluble, small proteins that mediate a variety of biological effects, including the regulation of the growth and differentiation of many cell types (see, for example, Arai et al., *Annu. Rev. Biochem.* 59:783 (1990); Mosmann, *Curr. Opin. Immunol.* 3:311 (1991); Paul and Seder, *Cell* 76:241 (1994)). Proteins that constitute the cytokine group include interleukins, interferons, colony stimulating factors, tumor necrosis factors, and other regulatory molecules. For example, human interleukin-17 is a cytokine which stimulates the expression of interleukin-6, intracellular adhesion molecule 1, interleukin-8, granulocyte macrophage colony-stimulating factor, and prostaglandin E2 expression, and plays a role in the preferential maturation of CD34+ hematopoietic precursors into neutrophils (Yao et al., *J. Immunol.* 155:5483 (1995); Fossiez et al., *J. Exp. Med.* 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains.

The demonstrated in vivo activities of cytokines and their receptors illustrate the clinical potential of, and need for, other cytokines, cytokine receptors, cytokine agonists, and cytokine antagonists. For example, demonstrated in vivo activities of the pro-inflammatory cytokine family illustrates the enormous clinical potential of, and need for antagonists of pro-inflammatory molecules.

DETAILED DESCRIPTION OF THE INVENTION

The present invention addresses these needs by providing antagonists to pro-inflammatory cytokines IL-17A and IL-17F. Specifically, the pro-inflammatory cytokines IL-17A and IL-17F have a high degree of sequence similarity, share many biological properties, and are both produced by activated T cells. They have both been implicated as factors that contribute to the progression of various autoimmune and inflammatory diseases including rheumatoid arthritis and asthma. In fact, reagents that negate IL-17A function significantly ameliorate disease incidence and severity in several mouse models of human disease. IL-17A mediates its effects through interaction with its cognate receptor, the IL-17 receptor (IL-17R), but the receptor for IL-17F has not yet been identified. We now report that we have identified the IL-17R-related molecule, ZcytoR14 as the receptor for IL-17F. However, we have also noted that this receptor binds to both IL-17A and IL-17F with a similar high affinity. IL-17R on the other hand, binds IL-17A with high affinity, but binds IL-17F with very low affinity. Consistent with this, we have shown that a soluble form of IL-17R blocks IL-17A binding and signaling in cells expressing either receptor, but does not interfere with binding or function of IL-17F to ZcytoR14. In contrast, a soluble form of ZcytoR14 antagonizes both IL-17A and IL-17F, either singly or together, in cells expressing either receptor. Since IL-17A intervention has been proposed as an effective therapy for several auto-immune diseases, using antagonists of the present invention, which may block, inhibit, reduce, antagonize or neutralize the activity of IL-17A, IL-17F, or both IL-17A and IL-17F, which include soluble ZcytoR14 receptors and neutralizing anti-ZcytoR14 antibodies, will have advantages over therapies that target only one of these two cytokines. The invention further provides uses therefor in inflammatory disease, as well as related compositions and methods.

A) Overview

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

A central event in both humoral and cell mediated immune responses is the activation and clonal expansion of helper T cells. Helper T cell activation is initiated by the interaction of the T cell receptor (TCR)-CD3 complex with an antigen-MHC on the surface of an antigen presenting cell. This interaction mediates a cascade of biochemical events that induce the resting helper T cell to enter a cell cycle (the G0 to G1 transition) and results in the expression of a high affinity receptor for IL-2 and sometimes IL-4. The activated T cell progresses through the cycle proliferating and differentiating into memory cells or effector cells.

In addition to the signals mediated through the TCR, activation of T cells involves additional costimulation induced by cytokines released by the antigen presenting cell or through interactions with membrane bound molecules on the antigen presenting cell and the T cell. The cytokines IL-1 and IL-6 have been shown to provide a costimulatory signal. Also, the interaction between the B7 molecule expressed on the surface of an antigen presenting cell and CD28 and CTLA-4 molecules expressed on the T cell surface effect T cell activation. Activated T cells express an increased number of cellular adhesion molecules, such as ICAM-1, integrins, VLA-4, LFA-1, CD56, etc.

T-cell proliferation in a mixed lymphocyte culture or mixed lymphocyte reaction (MLR) is an established indication of the ability of a compound to stimulate the immune system. In many immune responses, inflammatory cells infiltrate the site of injury or infection. The migrating cells may be neutrophilic, eosinophilic, monocytic or lymphocytic as can be determined by histologic examination of the affected tissues. Current Protocols in Immunology, ed. John E. Coligan, 1994, John Wiley & Sons, Inc.

Immune related diseases could be treated by suppressing the immune response. Using soluble receptors and/or neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Interleukin-17 (IL-17A) has been identified as a cellular ortholog of a protein encoded by the T lymphotropic Herpes virus Saimiri (HSV) [see, Rouvier et al., J. Immunol., 150 (12): 5445-5456 (19993); Yao et al., J. Immunol, 122(12): 5483-5486 (1995) and Yao et al., Immunity, 3(6):811-821 (1995)]. Subsequent characterization has shown that this protein is a potent cytokine that acts to induce proinflammatory responses in a wide variety of peripheral tissues. IL-17A is a disulfide-linked homodimeric cytokine of about 32 kDa which is synthesized and secreted only by CD4+ activated memory T cells (reviewed in Fossiez et al., Int. Rev. Immunol, 16: 541-551 [1998]). Specifically, IL-17 is synthesized as a precursor polypeptide of 155 amino acids with an N-terminal signal sequence of 19-23 residues and is secreted as a disulfide-linked homodimeric glycoprotein. 1'-17A is disclosed in WO9518826 (1995), WO9715320 (1997) and WO9704097 (1997), as well as U.S. Pat. No. 6,063,372.

Despite its restricted tissue distribution, IL-17A exhibits pleitropic biological activities on various types of cells. IL-17A has been found to stimulate the production of many cytokines. It induces the secretion of IL-6, IL-8, IL-12, leukemia inhibitory factor (LIF), prostaglandin E2, MCP-1 and G-CSF by adherent cells like fibroblasts, keratinocytes, epithelial and endothelial cells. IL-17A also has the ability to induce ICAM-1 surface expression, proliferation of T cells, and growth and differentiation of CD34.sup.+ human progenitors into neutrophils. IL-17A has also been implicated in bone metabolism, and has been suggested to play an important role in pathological conditions characterized by the presence of activated T cells and TNF-.alpha. production such as rheumatoid arthritis and loosening of bone implants (Van Bezooijen et al., J. Bone Miner. Res. 14: 1513-1521 [1999]). Activated T cells of synovial tissue derived from rheumatoid arthritis patients were found to secrete higher amounts of IL-17A than those derived from normal individuals or osteoarthritis patients (Chabaud et al., Arthritis Rheum. 42: 963-970 [1999]). It was suggested that this proinflammatory cytokine actively contributes to synovial inflammation in rheumatoid arthritis. Apart from its proinflammatory role, IL-17A seems to contribute to the pathology of rheumatoid arthritis by yet another mechanism. For example, IL-17A has been shown to induce the expression of osteoclast differentiation factor (ODF) mRNA in osteoblasts (Kotake et al., J. Clin. Invest., 103: 1345-1352 [1999]). ODF stimulates differentiation of progenitor cells into osteoclasts, the cells involved in bone resorption.

Since the level of IL-17A is significantly increased in synovial fluid of rheumatoid arthritis patients, it appears that IL-17A induced osteoclast formation plays a crucial role in bone resorption in rheumatoid arthritis. IL-17A is also believed to play a key role in certain other autoimmune disorders such as multiple sclerosis (Matusevicius et al., Mult. Scler., 5: 101-104 [1999]). IL-17A has further been shown, by intracellular signalling, to stimulate Ca.sup.2+ influx and a reduction in [cAMP], in human macrophages (Jovanovic et al., J. Immunol, 160:3513 [1998]). Fibroblasts treated with IL-17A induce the activation of NF-.kappa.B, [Yao et al., Immunity, 3:811 (1995), Jovanovic et al., supra], while macrophages treated with it activate NF-.kappa.B and mitogen-activated protein kinases (Shalom-Barek et al., J. Biol. Chem., 273:27467 [1998]).

Additionally, IL-17A also shares sequence similarity with mammalian cytokine-like factor 7 that is involved in bone and cartilage growth. Other proteins with which IL-17A polypeptides share sequence similarity are human embryo-derived interleukin-related factor (EDIRF) and interleukin-20.

Consistent with IL-17A's wide-range of effects, the cell surface receptor for IL-17A has been found to be widely expressed in many tissues and cell types (Yao et al., Cytokine, 9:794 [1997]). While the amino acid sequence of the human IL-17A receptor (IL-17R) (866 amino acids) predicts a protein with a single transmembrane domain and a long, 525 amino acid intracellular domain, the receptor sequence is unique and is not similar to that of any of the receptors from the cytokine/growth factor receptor family. This coupled with the lack of similarity of IL-17A itself to other known proteins indicates that IL-17A and its receptor may be part of a novel family of signalling proteins and receptors. It has been demonstrated that IL-17A activity is mediated through binding to its unique cell surface receptor, wherein previous studies have shown that contacting T cells with a soluble form of the IL-17A receptor polypeptide inhibited T cell proliferation and IL-2 production induced by PHA, concanavali and anti-TCR monoclonal antibody (Yao et al., J. Immunol., 155: 5483-5486 [1995]). As such, there is significant interest in identifying and characterizing novel polypeptides having homology to the known cytokine receptors, specifically IL-17A receptors.

The expression pattern of IL-17F appears to be similar to that of IL-17A, such that it includes only activated CD4+ T cells and monocytes (Starnes et al. J. Immunol. 167: 4137-4140 [2001]). IL-17F has been demonstrated to induce G-CSF, IL-6, and IL-8 in fibroblasts (Hymowitz et al, EMBO J. 20:5322-5341 [2001]) and TGF-b in endothelial cells (Starnes et al. J. Immunol. 167: 4137-4140 [2001]). It has recently been reported that IL-23, a cytokine produced by dendritic cell, can mediate the production of both IL-17A and IL-17F, primarily in memory T cells (Aggarwal et al. J. Biol. Chem. 278:1910-1914 [2003]).

Moreover, over expression or upregulation of both IL-17A and IL-17F have been shown in arthritic and asthmatic individuals (reviewed in Moseley et al. CytokineGrowth Factor Rev 14:155-174 [2003]). With regards to arthritis, these cytokines act in a manner characteristic to the cartilage and joint destruction that is associated with rheumatoid- and osteo-arthritis. For example, IL-17A and IL-17F have been demonstrated to enhance matrix degradation in articular cartilage explants via release of cartilage proteoglycan glycosaminoglycans and collagen fragments, while inhibiting the synthesis of new proteoglycans and collagens (Cai et al. Cytokine 16:10-21 [2001]; Attur et al Arthritis Rheum 44:2078-2083 [2001]).

Similar to IL-17A, overexpression of IL-17F in mice has also been shown to increase lung neutrophil recruitment and result in increased expression of Th1-associated cytokines in the lung, including IL-6, IFN-gamma, IP-10 and MIG (Starnes et al. J. Immunol. 167: 4137-4140 [2001]). IL-17F was also upregulated in T cells from allergen-challenged asthmatics (Kawaguchi et al J. Immunol. 167:4430-4435 [2001]), and found to induce IL-6 and IL-8 production in NHBE. In contrast to IL-17A, IL-17F appears to inhibit angiogenesis in vitro (Starnes et al. J. Immunol. 167: 4137-4140 [2001]).

IL-17F mRNA was not detected by northern blot in various human tissues but was dramatically induced upon activation of CD4+ T cells and monocytes. Id. In mice, Th2 cells and master cells were found to express IL-17F upon activation. See Dumont, Expert Opin. Ther. Patents 13(3) (2003). Like IL-17A, the expression of IL-17F was also found to be upregulated by IL-23 in mouse.

The Il-17 cytokine/receptor families appear to represent a unique signaling system within the cytokine network that will offer innovative approaches to the manipulation of immune and inflammatory responses. Accordingly, the present invention is based on the discovery of a new IL-17 family receptor, ZcytoR14 and its ability to bind both IL-17A and IL-17F.

As such, antagonists to IL-17F and IL-17A activity, such as ZcytoR14 soluble receptors and antibodies thereto including the anti-human-ZcytoR14 monoclonal and neutralizing antibodies of the present invention, are useful in therapeutic treatment of inflammatory diseases, particularly as antagonists to both IL-17F and IL-17A singly or together in the treatment of psoriasis. Moreover, antagonists to IL-17F activity, such as ZcytoR14 soluble receptors and antibodies thereto including the anti-human-ZcytoR14 monoclonal and neutralizing antibodies of the present invention, are useful in therapeutic treatment of other inflammatory diseases for example as bind, block, inhibit, reduce, antagonize or neutralize IL-17F and IL-17A (either individually or together) in the treatment of atopic and contact dermatitis, IBD, colitis, Endotoxemia, arthritis, rheumatoid arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection. intraabdominal adhesions and/or abscesses as results of peritoneal inflammation (i.e. from infection, injury, etc.), systemic lupus erythematosus (SLE), multiple sclerosis, systemic sclerosis, nephrotic syndrome, organ allograft rejection, graft vs. host disease (GVHD), kidney, lung, heart, etc. transplant rejection, streptococcal cell wall (SCW)-induced arthritis, osteoarthritis, gingivitis/periodontitis, herpetic stromal keratitis, cancers including prostate, renal, colon, ovarian, cervical, leukemia, angiogenesis, restenosis and kawasaki disease.

Cytokine receptors subunits are characterized by a multi-domain structure comprising a ligand-binding domain and an effector domain that is typically involved in signal transduction. Multimeric cytokine receptors include monomers, homodimers (e.g., PDGF receptor αα and ββ isoforms, erythropoietin receptor, MPL [thrombopoietin receptor], and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structures and functions. Class I hematopoietic receptors, for example, are characterized by the presence of a domain containing conserved cysteine residues and the WSXWS motif (SEQ ID NO:10). Additional domains, including protein kinase domains; fibronectin type III domains; and immunoglobulin domains, which are characterized by disulfide-bonded loops, are present in certain hematopoietic receptors. Cytokine receptor structure has been reviewed by Urdal, *Ann. Reports Med. Chem.* 26:221-228, 1991 and Cosman, *Cytokine* 5:95-106, 1993. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members.

Amongst other inventions, the present invention provides novel uses for a soluble receptor, designated "ZcytoR14" or "soluble ZcytoR14" or "sZcytoR14", all of which may be used herein interchangeably, or and neutralizing antibodies to ZcytoR14 cytokine receptors. The present invention also provides soluble ZcytoR14 polypeptide fragments and fusion proteins, for use in human inflammatory and autoimmune diseases. The anti-ZcytoR14 antibodies, and soluble ZcytoR14 receptors of the present invention, including the neutralizing anti-ZcytoR14 antibodies of the present invention, can be used to block, inhibit, reduce, antagonize or neutralize the activity of either IL-17F or IL-17A, or both IL-17A and IL-17F in the treatment of inflammation and inflammatory diseases such as psoriasis, psoriatic arthritis, rheumatoid arthritis, endotoxemia, inflammatory bowel disease (IBD), colitis, asthma, allograft rejection, immune mediated renal diseases, hepatobiliary diseases, multiple sclerosis, atherosclerosis, promotion of tumor growth, or degenerative joint disease and other inflammatory conditions disclosed herein.

An illustrative nucleotide sequence that encodes human ZcytoR14 is provided by SEQ ID NO:1; the encoded polypeptide is shown in SEQ ID NO:2. ZcytoR14 functions as a receptor for both IL-17A (SEQ ID NOS:13 & 14) and IL-17F (SEQ ID NOS:15 & 16). ZcytoR14 can act as a monomer, a homodimer or a heterodimer. Preferably, ZcytoR14 acts as a homodimeric receptor for both IL-17A and/or IL-17F. ZcytoR14 can also act as a heterodimeric receptor subunit for a IL-17-related cytokine. ZcytoR14 is disclosed in commonly owned U.S. patent application Ser. No. 10/458, 647, and commonly owned WIPO publication WO 01/04304, both of which are incorporated herein in their entirety by reference. Analysis of a human cDNA clone encoding ZcytoR14 (SEQ ID NO:1) revealed an open reading frame encoding 692 amino acids (SEQ ID NO:2) comprising a putative signal sequence of approximately 20 amino acid residues (amino acid residues 1 to 20 of SEQ ID NO:2), an extracellular ligand-binding domain of approximately 431 amino acid residues (amino acid residues 21-452 of SEQ ID NO:2; SEQ ID NO:3), a transmembrane domain of approximately 20 amino acid residues (amino acid residues 453-473 of SEQ ID NO:2), and an intracellular domain of approximately 203 amino acid residues (amino acid residues 474 to 677 of SEQ ID NO:2). Furthermore, a ligand binding domain is represented by SEQ ID NO:22.

Yet another illustrative nucleotide sequence that encodes a variant human ZcytoR14, designated as "ZcytoR14-1" is provided by SEQ ID NO:4, the encoded polypeptide is shown in SEQ ID NO:5. ZcytoR14-1 is disclosed in commonly owned U.S. patent application Ser. No. 10/458,647, and commonly owned WIPO publication WO 01/04304, both of which are incorporated herein in their entirety by reference. Sequence analysis revealed that Zcytor14-1 is a truncated form of receptor polypeptide. That is, Zcytor14-1 lacks amino acid residues 1-113 of SEQ ID NO:2. SEQ ID NO:10 presents an amino acid sequence of a Zcytor14-1 polypeptide that includes the N-terminal portion of Zcytor14.

A comparison of the Zcytor14 and Zcytor14-1 amino acid sequences also indicated that the two polypeptides represent alternatively spliced variants. The amino acid sequence of Zcytor14 includes a 17 amino acid segment (amino acid residues 339 to 355 of SEQ ID NO:2), which Zcytor14-1 lacks, while Zcytor14 lacks, following amino acid 479, a 13 amino acid segment found in Zcytor14-1 (amino acid residues 350 to 362 of SEQ ID NO:5). A polypeptide that contains both amino acid segments is provided by SEQ ID NO:11, whereas SEQ ID NO:12 presents the amino acid sequence of a polypeptide that lacks both 13 and 17 amino acid segments.

Yet another illustrative nucleotide sequence that encodes a variant human ZcytoR14, designated as "ZcytoR14-6" is provided by SEQ ID NO:23, the encoded polypeptide is shown in SEQ ID NO:24. ZcytoR14-6 contains a 25 amino acid residue deletion as compared to ZcytoR14 as embodied in SEQ ID NO:2. Specifically, ZcytoR14-6 does not contain amino acid residue 94 to amino acid residue 118 of SEQ ID NO:2. Analysis of a human cDNA clone encoding ZcytoR14-6 (SEQ ID NO:23) revealed an extracellular ligand-binding domain of approximately 427 amino acid residues (amino acid residues 1-427 of SEQ ID NO:24), a transmembrane domain of approximately 20 amino acid residues (amino acid residues 428-448 of SEQ ID NO:24), and an intracellular domain of approximately 218 amino acid residues (amino acid residues 449 to 667 of SEQ ID NO:24).

An illustrative nucleotide sequence that encodes a variant murine ZcytoR14 is provided by SEQ ID NO:25; the encoded polypeptide is shown in SEQ ID NO:26. Murine ZcytoR14 functions as a receptor for both murine IL-17A (SEQ ID NOS:17 & 18) and murine IL-17F (SEQ ID NOS:19 & 20). Analysis of a murine cDNA clone encoding ZcytoR14 (SEQ ID NO:1) revealed an extracellular ligand-binding domain of approximately 449 amino acid residues SEQ ID NO:27). Furthermore, a ligand binding domain is represented by SEQ ID NO:28.

Yet another illustrative nucleotide sequence that encodes a variant murine ZcytoR14 is provided by SEQ ID NO:29; the encoded polypeptide is shown in SEQ ID NO:30.

The Zcytor14 gene resides in chromosome 3p25-3p24. As discussed below, this region is associated with various disorders and diseases.

Northern analyses indicate that there is strong expression of the Zcytor14 gene in thyroid, adrenal gland, prostate, and liver tissues, and less expression in heart, small intestine, stomach, and trachea tissues. In contrast, there is little or no expression in brain, placenta, lung, skeletal muscle, kidney, pancreas, spleen, thymus, testis, ovary, colon, peripheral blood leukocytes, spinal cord, lymph node, and bone marrow. These observations show that Zcytor14 sequences can be used differentiate between various tissues.

As described below, the present invention provides isolated polypeptides comprising an amino acid sequence that is at least 70%, at least 80%, or at least 90%, or greater than 95%, such as 96%, 97%, 98%, or greater than 99% or more identical to a reference amino acid sequence of 21-692 of SEQ ID NO:2, wherein the isolated polypeptide specifically binds with an antibody that specifically binds with a polypeptide comprising the amino acid sequence of SEQ ID NO:2. The present invention also provides isolated polypeptides comprising an amino acid sequence that is at least 70%, at least 80%, or at least 90% identical to a reference amino acid sequence selected from the group consisting of: (a) amino acid residues 21 to 452 of SEQ ID NO:2, (b) amino acid residues 21 to 435 of SEQ ID NO:10, (c) amino acid residues 21 to 677 of SEQ ID NO:2, and (d) amino acid residues 1 to 692 of SEQ ID NO:2, wherein the isolated polypeptide specifically binds with an antibody that specifically binds with a polypeptide consisting of either the amino acid sequence of SEQ ID NO:2, or the amino acid sequence of SEQ ID NO:10. Illustrative polypeptides include a polypeptide comprising the amino acid sequence of SEQ ID NO:2, SEQ ID NO:10, SEQ ID NO:11, or SEQ ID NO:12.

The present invention also provides isolated polypeptides comprising an extracellular domain, wherein the extracellular domain comprises either amino acid residues 21 to 452 of the amino acid sequence of SEQ ID NO:2 or amino acid residues 21 to 435 of the amino acid sequence of SEQ ID NO:10. Such polypeptides may further comprise a transmembrane domain that resides in a carboxyl-terminal position relative to the extracellular domain, wherein the transmembrane domain comprises amino acid residues 453 to 473 of SEQ ID NO:2. These polypeptides may also comprise an intracellular domain that resides in a carboxyl-terminal position relative to the transmembrane domain, wherein the intracellular domain comprises either amino acid residues 474 to 677 of SEQ ID NO:2, or amino acid residues 457 to 673 of SEQ ID NO:10, and optionally, a signal secretory sequence that resides in an amino-terminal position relative to the extracellular domain, wherein the signal secretory sequence comprises amino acid residues 1 to 20 of the amino acid sequence of SEQ ID NO:2.

The present invention also includes variant Zcytor14 polypeptides, wherein the amino acid sequence of the variant polypeptide shares an identity with the amino acid sequence of SEQ ID NO:2 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:2 is due to one or more conservative amino acid substitutions.

Moreover, the present invention also provides isolated polypeptides as disclosed above that bind IL-17F (e.g., human IL-17F polypeptide sequence as shown in SEQ ID NO:16). The human IL-17F polynucleotide sequence is shown in SEQ ID NO:15. The mouse IL-17F polynucleotide sequence is shown in SEQ ID NO:19, and corresponding polypeptide is shown in SEQ ID NO:20. The present invention also provides isolated polypeptides as disclosed above that bind IL-17A (e.g., human IL-17A polypeptide sequence as shown in SEQ ID NO:14). The human IL-17A polynucleotide sequence is shown in SEQ ID NO:13. The mouse IL-17A polynucleotide sequence is shown in SEQ ID NO:17, and corresponding polypeptide is shown in SEQ ID NO:18.

The present invention also provides isolated polypeptides and epitopes comprising at least 15 contiguous amino acid residues of an amino acid sequence of SEQ ID NO:2 or 3. Illustrative polypeptides include polypeptides that either comprise, or consist of SEQ ID NO:2 or 3, an antigenic epitope thereof, or a functional IL-17A or IL-17F binding fragment thereof. Moreover, the present invention also provides isolated polypeptides as disclosed above that bind to, block, inhibit, reduce, antagonize or neutralize the activity of IL-17F or IL-17A.

The present invention also includes variant ZcytoR14 polypeptides, wherein the amino acid sequence of the variant polypeptide shares an identity with the amino acid residues of SEQ ID NO:2 selected from the group consisting of at least 70% identity, at least 80% identity, at least 90% identity, at least 95% identity, or greater than 95% identity, such as 96%, 97%, 98%, or greater than 99% or more identity, and wherein any difference between the amino acid sequence of the variant polypeptide and the corresponding amino acid sequence of SEQ ID NO:2 is due to one or more conservative amino acid substitutions. Such conservative amino acid substitutions are described herein. Moreover, the present invention also provides isolated polypeptides as disclosed above that bind to, block, inhibit, reduce, antagonize or neutralize the activity of IL-17F or IL-17A.

The present invention further provides antibodies and antibody fragments that specifically bind with such polypeptides. Exemplary antibodies include neutralizing antibodies, polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. Neutralizing antibodies preferably bind ZcytoR14 such that the interaction of IL-17A and IL-17F with ZcytoR14 is blocked, inhibited, reduced, antagonized or neutralized; anti-ZcytoR14 neutralizing antibodies such that the binding of either IL-17A or IL-17F to ZcytoR14 is blocked, inhibited, reduced, antagonized or neutralized are also encompassed by the present invention. That is, the neutralizing anti-ZcytoR14 antibodies of the present invention can either either bind, block, inhibit, reduce, antagonize or neutralize each of IL-17A or IL-17F singly, or bind, block, inhibit, reduce, antagonize or neutralize IL-17A and IL-17F together. The present invention further includes compositions comprising a carrier and a peptide, polypeptide, or antibody described herein.

In addition, the present invention provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide or antibody described herein.

The present invention also contemplates anti-idiotype antibodies, or anti-idiotype antibody fragments, that specifically bind an antibody or antibody fragment that specifically binds a polypeptide comprising the amino acid sequence of SEQ ID NO:2 or a fragment thereof. An exemplary anti-idiotype antibody binds with an antibody that specifically binds a polypeptide consisting of SEQ ID NO:2.

The present invention also provides fusion proteins, comprising a ZcytoR14 polypeptide and an immunoglobulin moiety. In such fusion proteins, the immunoglobulin moiety may be an immunoglobulin heavy chain constant region, such as a human F$_c$ fragment. The present invention further includes isolated nucleic acid molecules that encode such fusion proteins.

The present invention also provides polyclonal and monoclonal antibodies that bind to polypeptides comprising an ZcytoR14 extracellular domain such as monomeric, homodimeric, heterodimeric and multimeric receptors, including soluble receptors. Moreover, such antibodies can be used antagonize the binding of ZcytoR14 ligands, IL-17F (SEQ ID NO:16), and IL-17A (SEQ ID NO:14), individually or together to the ZcytoR14 receptor.

These and other aspects of the invention will become evident upon reference to the following detailed description. In addition, various references are identified below and are incorporated by reference in their entirety.

B) Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces ZcytoR14 from an expression vector. In contrast, ZcytoR14 can be produced by a cell that is a "natural source" of ZcytoR14, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a ZcytoR14 polypeptide fused with a polypeptide that binds an affinity matrix. Such a fusion protein provides a means to isolate large quantities of ZcytoR14 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly ligand-binding receptor polypeptides that lack transmembrane and cytoplasmic domains, and other linkage to the cell membrane such as via glycophosphoinositol (gpi). Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Soluble receptors can be monomeric, homodimeric, heterodimeric, or multimeric, with multimeric receptors generally not comprising more than 9 subunits, preferably not comprising more than 6 subunits, and most preferably not comprising more than 3 subunits. Receptor polypeptides are said to be substantially free of transmembrane and intracellular polypeptide segments when they lack sufficient portions of these segments to provide membrane anchoring or signal transduction, respectively. Soluble receptors of cytokine receptors generally comprise the extracellular cytokine binding domain free of a transmembrane domain and intracellular domain. For example, representative soluble receptors include soluble receptors for IL-17R as shown in SEQ ID NO:21. It is well within the level of one of skill in the art to delineate what sequences of a known cytokine receptor sequence comprise the extracellular cytokine binding domain free of a transmembrane domain and intracellular domain. Moreover, one of skill in the art using the genetic code can readily determine polynucleotides that encode such soluble receptor polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and the like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ M$^{-1}$.

An "anti-idiotype antibody" is an antibody that binds with the variable region domain of an immunoglobulin. In the present context, an anti-idiotype antibody binds with the variable region of an anti-ZcytoR14 antibody, and thus, an anti-idiotype antibody mimics an epitope of ZcytoR14.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-ZcytoR14 monoclonal antibody fragment binds with an epitope of ZcytoR14.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain. Construction of humanized antibodies for therapeutic use in humans that are derived from murine antibodies, such as those that bind to or neutralize a human protein, is within the skill of one in the art.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a ZcytoR14 polypeptide component.

Examples of an antibody fusion protein include a protein that comprises a ZcytoR14 extracellular domain, and either an Fc domain or an antigen-binding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for ZcytoR14" or a "ZcytoR14 anti-sense oligonucleotide" is an oligonucleotide having a sequence (a) capable of forming a stable triplex with a portion of the ZcytoR14 gene, or (b) capable of forming a stable duplex with a portion of an mRNA transcript of the ZcytoR14 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant ZcytoR14 gene" refers to nucleic acid molecules that encode a polypeptide having an amino acid sequence that is a modification of SEQ ID NO:2. Such variants include naturally-occurring polymorphisms of ZcytoR14 genes, as well as synthetic genes that contain conservative amino acid substitutions of the amino acid sequence of SEQ ID NO:2. Additional variant forms of ZcytoR14 genes are nucleic acid molecules that contain insertions or deletions of the nucleotide sequences described herein. A variant ZcytoR14 gene can be identified, for example, by determining whether the gene hybridizes with a nucleic acid molecule having the nucleotide sequence of SEQ ID NO:1 OR SEQ ID NO:4, or its complement, under stringent conditions.

Alternatively, variant ZcytoR14 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins,"

in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant ZcytoR14 gene or variant ZcytoR14 polypeptide, a variant gene or polypeptide encoded by a variant gene may be functionally characterized the ability to bind specifically to an anti-ZcytoR14 antibody. A variant ZcytoR14 gene or variant ZcytoR14 polypeptide may also be functionally characterized the ability to bind to its ligand, for example, IL-17A and/or IL-17F, using a biological or biochemical assay described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of ZcytoR14 genes. Within the context of this invention, a "functional fragment" of a ZcytoR14 gene refers to a nucleic acid molecule that encodes a portion of a ZcytoR14 polypeptide which is a domain described herein or at least specifically binds with an anti-ZcytoR14 antibody.

Due to the imprecision of standard analytical methods, molecular weights and lengths of polymers are understood to be approximate values. When such a value is expressed as "about" X or "approximately" X, the stated value of X will be understood to be accurate to ±10%.

C) Production of ZcytoR14 Polynucleotides or Genes

Nucleic acid molecules encoding a human ZcytoR14 gene can be obtained by screening a human cDNA or genomic library using polynucleotide probes based upon SEQ ID NO:1 OR SEQ ID NO:4. These techniques are standard and well-established, and may be accomplished using cloning kits available by commercial suppliers. See, for example, Ausubel et al. (eds.), *Short Protocols in Molecular Biology*, 3$^{rd}$ Edition, John Wiley & Sons 1995; Wu et al., *Methods in Gene Biotechnology*, CRC Press, Inc. 1997; Aviv and Leder, *Proc. Nat'l Acad. Sci. USA* 69:1408 (1972); Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47-52.

Nucleic acid molecules that encode a human ZcytoR14 gene can also be obtained using the polymerase chain reaction (PCR) with oligonucleotide primers having nucleotide sequences that are based upon the nucleotide sequences of the ZcytoR14 gene or cDNA. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), Humana Press, Inc., 1993. Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), Humana Press, Inc. 1993. As an alternative, a ZcytoR14 gene can be obtained by synthesizing nucleic acid molecules using mutually priming long oligonucleotides and the nucleotide sequences described herein (see, for example, Ausubel (1995)). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, (Humana Press, Inc. 1993), and Holowachuk et al., *PCR Methods Appl.* 4:299 (1995)). For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

D) Production of ZcytoR14 Gene Variants

The present invention provides a variety of nucleic acid molecules, including DNA and RNA molecules, that encode the ZcytoR14 polypeptides disclosed herein. Those skilled in the art will readily recognize that, in view of the degeneracy of the genetic code, considerable sequence variation is possible among these polynucleotide molecules. Moreover, the present invention also provides isolated soluble monomeric, homodimeric, heterodimeric and multimeric receptor polypeptides that comprise at least one ZcytoR14 receptor subunit that is substantially homologous to the receptor polypeptide of SEQ ID NO:2. Thus, the present invention contemplates ZcytoR14 polypeptide-encoding nucleic acid molecules comprising degenerate nucleotides of SEQ ID NO:1 or SEQ ID NO:4, and their RNA equivalents.

Those skilled in the art will readily recognize that, in view of the degeneracy of the genetic code, considerable sequence variation is possible among these polynucleotide molecules. SEQ ID NO:7 is a degenerate nucleotide sequence that encompasses all nucleic acid molecules that encode the Zcytor14 polypeptide of SEQ ID NO:2. Those skilled in the art will recognize that the degenerate sequence of SEQ ID NO:7 also provides all RNA sequences encoding SEQ ID NO:2, by substituting U for T. Thus, the present invention contemplates Zcytor14 polypeptide-encoding nucleic acid molecules comprising nucleotide 154 to nucleotide 2229 of SEQ ID NO:1, and their RNA equivalents. Similarly, the Zcytor14-1 degenerate sequence of SEQ ID NO:6 also provides all RNA sequences encoding SEQ ID NO:5, by substituting U for T.

Table 1 sets forth the one-letter codes to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
| --- | --- | --- | --- |
| A | A | T | T |
| C | C | G | G |
| G | G | C | C |

TABLE 1-continued

| Nucleotide | Resolution | Complement | Resolution |
|---|---|---|---|
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:3. Variant sequences can be readily tested for functionality as described herein.

Different species can exhibit "preferential codon usage." In general, see, Grantham et al., *Nucl. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

A ZcytoR14-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human ZcytoR14 sequences disclosed herein. In addition, a cDNA library can be used to transform or transfect host cells, and expression of the cDNA of interest can be detected with an antibody to ZcytoR14 polypeptide.

Those skilled in the art will recognize that the sequence disclosed in SEQ ID NO:1 represents a single allele of human ZcytoR14, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of the ZcytoR14 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Using the methods discussed above, one of ordinary skill in the art can prepare a variety of polypeptides that comprise a soluble ZcytoR14 receptor subunit that is substantially homologous to either SEQ ID NO:1 or SEQ ID NO:4, or that encodes amino acids of either SEQ ID NO:2 or SEQ ID NO:5, or allelic variants thereof and retain the ligand-binding properties of the wild-type ZcytoR14 receptor. Such polypeptides may also include additional polypeptide segments as generally disclosed herein.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1 OR SEQ ID NO:4, or to nucleic acid molecules comprising a nucleotide sequence complementary to SEQ ID NO:1 OR SEQ ID NO:4, or fragments thereof.

In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Following hybridization, the nucleic acid molecules can be washed to remove non-hybridized nucleic acid molecules under stringent conditions, or under highly stringent conditions. See, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user-defined criteria. It is well within the abilities of one skilled in the art to adapt hybridization and wash conditions for use with a particular polynucleotide hybrid.

The present invention also provides isolated ZcytoR14 polypeptides that have a substantially similar sequence identity to the polypeptides of SEQ ID NO:2, or their orthologs. The term "substantially similar sequence identity" is used herein to denote polypeptides having at least 70%, at least 80%, at least 90%, at least 95%, such as 96%, 97%, 98%, or greater than 95% sequence identity to the sequences shown in SEQ ID NO:2, or their orthologs. For example, variant and orthologous ZcytoR14 receptors can be used to generate an immune response and raise cross-reactive antibodies to human ZcytoR14. Such antibodies can be humanized, and modified as described herein, and used therapeutically to treat psoriasis, psoriatic arthritis, IBD, colitis, endotoxemia as well as in other therapeutic applications described herein.

The present invention also contemplates ZcytoR14 variant nucleic acid molecules that can be identified using two criteria: a determination of the similarity between the encoded polypeptide with the amino acid sequence of SEQ ID NO:2, and a hybridization assay. Such ZcytoR14 variants include nucleic acid molecules (1) that remain hybridized with a nucleic acid molecule having the nucleotide sequence of SEQ ID NO:1 OR SEQ ID NO:4 (or its complement) under stringent washing conditions, in which the wash stringency is equivalent to 0.5×-2×SSC with 0.1% SDS at 55-65° C., and (2) that encode a polypeptide having at least 70%, at least 80%, at least 90%, at least 95%, or greater than 95% such as 96%, 97%, 98%, or 99%, sequence identity to the amino acid sequence of SEQ ID NO:2. Alternatively, ZcytoR14 variants can be characterized as nucleic acid molecules (1) that remain hybridized with a nucleic acid molecule having the nucleotide sequence of SEQ ID NO:1 OR SEQ ID NO:4 (or its complement) under highly stringent washing conditions, in which the wash stringency is equivalent to 0.1×-0.2×SSC with 0.1% SDS at 50-65° C., and (2) that encode a polypeptide having at least 70%, at least 80%, at least 90%, at least 95% or greater than 95%, such as 96%, 97%, 98%, or 99% or greater, sequence identity to the amino acid sequence of SEQ ID NO:2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative ZcytoR14 variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:2 or SEQ ID NO:3) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with an amino acid sequence disclosed herein. For example, variants can be obtained that contain one or more amino acid substitutions of SEQ ID NO:2, in which an alkyl amino acid is substituted for an alkyl amino acid in a ZcytoR14 amino acid sequence, an aromatic amino acid is substituted for an aromatic amino acid in a ZcytoR14 amino acid sequence, a sulfur-containing amino acid is substituted for a sulfur-containing amino acid in a ZcytoR14 amino acid sequence, a hydroxy-containing amino acid is substituted for a hydroxy-containing amino acid in a ZcytoR14 amino acid sequence, an acidic amino acid is substituted for an acidic amino acid in a ZcytoR14 amino acid sequence, a basic amino acid is substituted for a basic amino acid in a ZcytoR14 amino acid sequence, or a dibasic monocarboxylic amino acid is substituted for a dibasic monocarboxylic amino acid in a ZcytoR14 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3). Particular variants of ZcytoR14 are characterized by having at least 70%, at least 80%, at least 90%, at least 95% or greater than 95% such as 96%, 97%, 98%, or 99% or greater sequence identity to the corresponding amino acid sequence (e.g., SEQ ID NO:2), wherein the variation in amino acid sequence is due to one or more conservative amino acid substitutions.

Conservative amino acid changes in a ZcytoR14 gene can be introduced, for example, by substituting nucleotides for the nucleotides recited in SEQ ID NO:1 OR SEQ ID NO:4. Such "conservative amino acid" variants can be obtained by oligonucleotide-directed mutagenesis, linker-scanning mutagenesis, mutagenesis using the polymerase chain reaction, and the like (see Ausubel (1995); and McPherson (ed.), *Directed Mutagenesis: A Practical Approach* (IRL Press 1991)). A variant ZcytoR14 polypeptide can be identified by the ability to specifically bind anti-ZcytoR14 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tent-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for ZcytoR14 amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

Although sequence analysis can be used to further define the ZcytoR14 ligand binding region, amino acids that play a role in ZcytoR14 binding activity (such as binding of ZcytoR14 to either Il-17A or IL-17F, or to an anti-ZcytoR14 antibody) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, ZcytoR14 labeled with biotin or FITC can be used for expression cloning of ZcytoR14 ligands.

Variants of the disclosed ZcytoR14 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-ZcytoR14 antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of ZcytoR14 polypeptides and nucleic acid molecules encoding such functional fragments. Routine deletion analyses of nucleic acid molecules can be performed to obtain functional fragments of a nucleic acid molecule that encodes a ZcytoR14 polypeptide. As an illustration, DNA molecules having the nucleotide sequence of SEQ ID NO:1 OR SEQ ID NO:4 can be digested with Bal31 nuclease to obtain a series of nested deletions. The fragments are then inserted into expression vectors in proper reading frame, and the expressed polypeptides are isolated and tested for the ability to bind anti-ZcytoR14 antibodies. One alternative to exonuclease digestion is to use oligonucleotide-directed mutagenesis to introduce deletions or stop codons to specify production of a desired fragment. Alternatively, particular fragments of a ZcytoR14 gene can be synthesized using the polymerase chain reaction.

This general approach is exemplified by studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation, Vol.* 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a ZcytoR14 gene that have amino acid changes, compared with an amino acid sequence disclosed herein. A variant ZcytoR14 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant ZcytoR14 gene can hybridize to a nucleic acid molecule comprising a nucleotide sequence, such as SEQ ID NO:1 OR SEQ ID NO:4.

The present invention also includes using functional fragments of ZcytoR14 polypeptides, antigenic epitopes, epitope-bearing portions of ZcytoR14 polypeptides, and nucleic acid molecules that encode such functional fragments, antigenic epitopes, epitope-bearing portions of ZcytoR14 polypeptides. Such fragments are used to generate polypeptides for use in generating antibodies and binding partners that bind, block, inhibit, reduce, antagonize or neutralize activity of IL-17A or IL-17F or both IL-17A and IL-17F. A "functional" ZcytoR14 polypeptide or fragment thereof as defined herein is characterized by its ability to block, inhibit, reduce, antagonize or neutralize IL-17A or IL-17F inflammatory, proliferative or differentiating activity, by its ability to induce or inhibit specialized cell functions, or by its ability to bind specifically to an anti-ZcytoR14 antibody, cell, IL-17A or IL-17F. As previously described herein, ZcytoR14 is characterized by a unique cytokine receptor structure and domains as described herein. Thus, the present invention further contemplates using fusion proteins encompassing: (a) polypeptide molecules comprising one or more of the domains described above; and (b) functional fragments comprising one or more of these domains. The other polypeptide portion of the fusion protein may be contributed by another cytokine receptor, such as IL-10R, IL-13R, IL-17R, IL-10RB (CRF2-4), or by a non-native and/or an unrelated secretory signal peptide that facilitates secretion of the fusion protein.

The present invention also provides polypeptide fragments or peptides comprising an epitope-bearing portion of a ZcytoR14 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides, antigenic peptides, epitopes, and polypeptides of the present invention are useful to raise antibodies that bind with the polypeptides described herein, as well as to identify and screen anti-ZcytoR14 monoclonal antibodies that are neutralizing, and that may bind, block, inhibit, reduce, antagonize or neutralize the activity of IL-17F and IL-17A (individually or together). Such neutralizing monoclonal antibodies of the present invention can bind to an ZcytoR14 antigenic epitope. Hopp/Woods hydrophilicity profiles can be used to determine regions that have the most antigenic potential within SEQ ID NO:2 or 4 (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. In ZcytoR14 these regions can be determined by one of skill in the art. Moreover, ZcytoR14 antigenic epitopes within SEQ ID NO:2 or 4 as predicted by a Jameson-Wolf plot, e.g., using DNASTAR Protean program (DNASTAR, Inc., Madison, Wis.) serve as preferred antigenic epitopes, and can be determined by one of skill in the art. The results of this analysis indicated that the following amino acid sequences of SEQ ID NO:2 would provide suitable antigenic peptides:amino acids 26 to 33 ("antigenic peptide 1"), amino acids 41 to 46 ("antigenic peptide 2"), 74 to 81 ("antigenic peptide 3"), amino acids 95 to 105 ("antigenic peptide 4"), amino acids 109 to 119 ("antigenic peptide 5"), amino acids 95 to 119 ("antigenic peptide 6"), amino acids 178 to 185 ("antigenic peptide 7"), amino acids 200 to 206 ("antigenic peptide 8"), amino acids 231 to 238 ("antigenic peptide 9"), amino acids 231 to 241 ("antigenic peptide 10"), amino acids 264 to 270 ("antigenic peptide 11"), amino acids 274 to 281 ("antigenic peptide 12"), amino acids 317 to 324 ("antigenic peptide 13"), amino acids 357 to 363 ("antigenic peptide 14"), amino acids 384 to 392 ("antigenic peptide 15"), amino acids 398 to 411 ("antigenic peptide 16"), amino acids 405 to 411 ("antigenic peptide 17"), amino acids 423 to 429 ("antigenic peptide 18"), and amino acids 434 to 439 ("antigenic peptide 19"). The present invention contemplates the use of any one of antigenic peptides 1 to 19 to generate antibodies to Zcytor14. The present invention also contemplates polypeptides comprising at least one of antigenic peptides 1 to 19.

In preferred embodiments, antigenic epitopes to which neutralizing antibodies of the present invention bind would contain residues of SEQ ID NO:2 (and corresponding residues of SEQ ID NO:3) or SEQ ID NO:5 that are important to ligand-receptor binding, for example, with ZcytoR14 and IL-17A or IL-17F (individually or together).

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a ZcytoR14 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

For any ZcytoR14 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise ZcytoR14 variants based upon the nucleotide and amino acid sequences described herein.

E) Production of ZcytoR14 Polypeptides

The polypeptides of the present invention, including full-length polypeptides; soluble monomeric, homodimeric, heterodimeric and multimeric receptors; full-length receptors; receptor fragments (e.g. ligand-binding fragments and antigenic epitopes), functional fragments, and fusion proteins, can be produced in recombinant host cells following conventional techniques. To express a ZcytoR14 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, an ZcytoR14 expression vector may comprise a ZcytoR14 gene and a secretory sequence derived from any secreted gene.

ZcytoR14 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from mammalian viral sources, for example, adenovirus, bovine papilloma virus, simian virus, or the like, in which the regulatory signals are associated with a particular gene which has a high level of expression. Suitable transcriptional and translational regulatory sequences also can be obtained from mammalian genes, for example, actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control ZcytoR14 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

In certain embodiments, a DNA sequence encoding a ZcytoR14 soluble receptor polypeptide, or a fragment of ZcytoR14 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase (DHFR), which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

ZcytoR14 polypeptides can also be produced by cultured mammalian cells using a viral delivery system. Exemplary viruses for this purpose include adenovirus, retroviruses, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

ZcytoR14 can also be expressed in other higher eukaryotic cells, such as avian, fungal, insect, yeast, or plant cells. The baculovirus system provides an efficient means to introduce cloned ZcytoR14 genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the ZcytoR14 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed ZcytoR14 polypeptide, for example, a Glu-Glu epitope tag (Grussenmeyer et al., *Proc. Nat'l Acad. Sci.* 82:7952 (1985)). Using a technique known in the art, a transfer vector containing a ZcytoR14 gene is transformed into *E. coli*, and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270: 1543 (1995). In such transfer vector constructs, a short or long version of the basic protein promoter can be used. Moreover, transfer vectors can be constructed which replace the native ZcytoR14 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native ZcytoR14 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147-168 (The Humana Press, Inc. 1991), by Patel et al., "The baculovirus expression system," in *DNA Cloning 2: Expression Systems, 2nd Edition*, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae, Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615, 974, and Bitter, U.S. Pat. No. 4,977,092) and alcohol dehydrogenase genes. See also U.S. Pat. Nos. 4,990,446, 5,063, 154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67-88 (CRC Press, 1993).

Alternatively, ZcytoR14 genes can be expressed in prokaryotic host cells. Suitable promoters that can be used to express ZcytoR14 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloram-phenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Suitable prokaryotic hosts include *E. coli* and *Bacillus subtilus*. Suitable strains of *E. coli* include BL21(DE3), BL21 (DE3) pLysS, BL21(DE3) pLysE, DH1, DH4I, DH5, DH5I, DH51F', DH51MCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)).

When expressing a ZcytoR14 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning* 2: Expression Systems, *2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:2 or 5. As an illustration, polypeptides can comprise at least six, at least nine, or at least 15 contiguous amino acid residues of SEQ ID NO:2 or 5. Within certain embodiments of the invention, the polypeptides comprise 20, 30, 40, 50, 100, or more contiguous residues of these amino acid sequences. Nucleic acid molecules encoding such peptides and polypeptides are useful as polymerase chain reaction primers and probes.

Moreover, ZcytoR14 polypeptides and fragments thereof can be expressed as monomers, homodimers, heterodimers, or multimers within higher eukaryotic cells. Such cells can be used to produce ZcytoR14 monomeric, homodimeric, heterodimeric and multimeric receptor polypeptides that comprise at least one ZcytoR14 polypeptide ("ZcytoR14-comprising receptors" or "ZcytoR14-comprising receptor polypeptides"), or can be used as assay cells in screening systems. Within one aspect of the present invention, a polypeptide of the present invention comprising the ZcytoR14 extracellular domain is produced by a cultured cell, and the cell is used to screen for ligands for the receptor, including the natural ligand, IL-17F, as well as IL-17A, or even agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems. Each component of the monomeric, homodimeric, heterodimeric and multimeric receptor complex can be expressed in the same cell. Moreover, the components of the monomeric, homodimeric, heterodimeric and multimeric receptor complex can also be fused to a transmembrane domain or other membrane fusion moiety to allow complex assembly and screening of transfectants as described above.

To assay the IL-17A and IL-17F antagonist polypeptides and antibodies of the present invention, mammalian cells suitable for use in expressing ZcytoR14-comprising receptors or other receptors known to bind IL-17A or IL-17F (e.g., cells expressing IL-17R) and transducing a receptor-mediated signal include cells that express other receptor subunits that may form a functional complex with ZcytoR14. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, Cell 41: 727-734, (1985)) which is an IL-3 dependent murine pre-B cell line. Other cell lines include BHK, COS-1 and CHO cells. Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the human receptor cDNA can be cloned and used within cell lines from the same species, such as a mouse cDNA in the BaF3 cell line. Cell lines that are dependent upon one hematopoietic growth factor, such as GM-CSF or IL-3, can thus be engineered to become dependent upon another cytokine that acts through the ZcytoR14 receptor, such as IL-17F or IL-17A.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, J. Immunol. Meth. 65: 55-63, (1983)). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., Cell 56:563-572, (1989). A preferred such reporter gene is a luciferase gene (de Wet et al., Mol. Cell. Biol. 7:725, (1987)). Expression of the luciferase gene is detected by luminescence using methods known in the art (e.g., Baumgartner et al., J. Biol. Chem. 269:29094-29101, (1994); Schenborn and Goiffin, Promega Notes 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

An additional screening approach provided by the present invention includes the use of hybrid receptor polypeptides. These hybrid polypeptides fall into two general classes. Within the first class, the intracellular domain of ZcytoR14, is joined to the ligand-binding domain of a second receptor. A second class of hybrid receptor polypeptides comprise the extracellular (ligand-binding) domain of ZcytoR14 (SEQ ID NO:3) with an intracellular domain of a second receptor, preferably a hematopoietic cytokine receptor, and a transmembrane domain. Hybrid ZcytoR14 monomers, homodimers, heterodimers and multimers of the present invention receptors of this second class are expressed in cells known to be capable of responding to signals transduced by the second receptor. Together, these two classes of hybrid receptors enable the identification of a responsive cell type for the development of an assay for detecting IL-17F or IL-17A. Moreover, such cells can be used in the presence of IL-17F or IL-17A to assay the soluble receptor antagonists of the present invention in a competition-type assay. In such assay, a decrease in the proliferation or signal transduction activity of IL-17F or IL-17A in the presence of a soluble receptor of the present invention demonstrates antagonistic activity. Moreover ZcytoR14-soluble receptor binding assays, an cell-based assays, can also be used to assess whether a soluble receptor binds, blocks, inhibits, reduces, antagonizes or neutralizes IL-17F or IL-17A activity.

F) Production of ZcytoR14 Fusion Proteins and Conjugates

One general class of ZcytoR14 analogs are variants having an amino acid sequence that is a mutation of the amino acid sequence disclosed herein. Another general class of ZcytoR14 analogs is provided by anti-idiotype antibodies, and fragments thereof, as described below. Moreover, recombinant antibodies comprising anti-idiotype variable domains can be used as analogs (see, for example, Monfardini et al., Proc. Assoc. Am. Physicians 108:420 (1996)). Since the variable domains of anti-idiotype ZcytoR14 antibodies mimic ZcytoR14, these domains can provide ZcytoR14 binding activity. Methods of producing anti-idiotypic catalytic antibodies are known to those of skill in the art (see, for example, Joron et al., Ann. NY Acad. Sci. 672:216 (1992), Friboulet et al., Appl. Biochem. Biotechnol. 47:229 (1994), and Avalle et al., Ann. NY Acad. Sci. 864:118 (1998)).

Another approach to identifying ZcytoR14 analogs is provided by the use of combinatorial libraries. Methods for constructing and screening phage display and other combinatorial libraries are provided, for example, by Kay et al., Phage Display of Peptides and Proteins (Academic Press 1996), Verdine, U.S. Pat. No. 5,783,384, Kay, et. al., U.S. Pat. No. 5,747,334, and Kauffman et al., U.S. Pat. No. 5,723,323.

ZcytoR14 polypeptides have both in vivo and in vitro uses. As an illustration, a soluble form of ZcytoR14 can be added to cell culture medium to inhibit the effects of the ZcytoR14 ligand (i.e. IL-17F, IL-17A or both) produced by the cultured cells.

Fusion proteins of ZcytoR14 can be used to express ZcytoR14 in a recombinant host, and to isolate the produced ZcytoR14. As described below, particular ZcytoR14 fusion proteins also have uses in diagnosis and therapy. One type of fusion protein comprises a peptide that guides a ZcytoR14 polypeptide from a recombinant host cell. To direct a ZcytoR14 polypeptide into the secretory pathway of a eukaryotic host cell, a secretory signal sequence (also known as a signal peptide, a leader sequence, prepro sequence or pre sequence) is provided in the ZcytoR14 expression vector. While the secretory signal sequence may be derived from ZcytoR14, a suitable signal sequence may also be derived from another secreted protein or synthesized de novo. The secretory signal sequence is operably linked to a ZcytoR14-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of ZcytoR14 or another protein produced by mammalian cells (e.g., tissue-type plasminogen activator signal sequence, as described, for example, in U.S. Pat. No. 5,641,655) is useful for expression of ZcytoR14 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHOS gene). See, for example, Romanos et al., "Expression of Cloned Genes in Yeast," in *DNA Cloning 2: A Practical Approach,* 2$^{nd}$ Edition, Glover and Hames (eds.), pages 123-167 (Oxford University Press 1995).

ZcytoR14 soluble receptor polypeptides can be prepared by expressing a truncated DNA encoding the extracellular domain, for example, a polypeptide which contains SEQ ID NO:3, or the corresponding region of a non-human receptor. It is preferred that the extracellular domain polypeptides be prepared in a form substantially free of transmembrane and intracellular polypeptide segments. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide (Hopp et al., *Biotechnology* 6:1204-1210, (1988); available from Eastman Kodak Co., New Haven, Conn.) or another polypeptide or protein for which an antibody or other specific binding agent is available, can be fused to the receptor polypeptide. Moreover, ZcytoR14 antigenic epitopes from the extracellular cytokine binding domains are also prepared as described above.

In an alternative approach, a receptor extracellular domain of ZcytoR14 or other cytokine receptor component can be expressed as a fusion with immunoglobulin heavy chain constant regions, typically an $F_c$ fragment, which contains two constant region domains and a hinge region but lacks the variable region (See, Sledziewski, A Z et al., U.S. Pat. Nos. 6,018,026 and 5,750,375). The soluble ZcytoR14 polypeptides of the present invention include such fusions. One such fusion is shown in SEQ ID NO:64. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block, inhibit or reduce signals in vitro by specifically titrating out ligand, and as antagonists in vivo by administering them parenterally to bind circulating ligand and clear it from the circulation. To purify ligand, a ZcytoR14-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to regulate inflammatory responses including acute phase responses such as serum amyloid A (SAA), C-reactive protein (CRP), and the like. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_c$ region and used in an ELISA format.

To assist in isolating anti-ZcytoR14 and binding partners of the present invention, an assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.). Moreover, BIACORE technology, described above, can be used to be used in competition experiments to determine if different monoclonal antibodies bind the same or different epitopes on the ZcytoR14 polypeptide, and as such, be used to aid in epitope mapping of neutralizing antibodies of the present invention that bind, block, inhibit, reduce, antagonize or neutralize IL-17F or both IL-17A and IL-17F.

Ligand-binding receptor polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

The present invention further provides a variety of other polypeptide fusions and related multimeric proteins comprising one or more polypeptide fusions. For example, a soluble ZcytoR14 receptor can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble ZcytoR14 fusions can be expressed in genetically engineered cells to produce a variety of multimeric ZcytoR14 receptor analogs. Auxiliary domains can be fused to soluble ZcytoR14 receptor to target them to specific cells, tissues, or macromolecules (e.g., collagen, or cells expressing the ZcytoR14 ligands, IL-17F or IL-17A). A ZcytoR14 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

In bacterial cells, it is often desirable to express a heterologous protein as a fusion protein to decrease toxicity, increase stability, and to enhance recovery of the expressed protein. For example, ZcytoR14 can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a ZcytoR14 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

Another form of fusion protein comprises a ZcytoR14 polypeptide and an immunoglobulin heavy chain constant region, typically an $F_c$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:9). In this fusion protein, an illustrative Fc moiety is a human γ4 chain, which is stable in solution and has little or no complement activating activity. Accordingly, the present invention contemplates a ZcytoR14 fusion protein that comprises a ZcytoR14 moiety and a human Fc fragment, wherein the C-terminus of the ZcytoR14 moiety is attached to the N-terminus of the Fc fragment via a peptide linker, such as a peptide comprising the amino acid sequence of SEQ ID NO:2 or SEQ ID NO:5. The ZcytoR14 moiety can be a ZcytoR14 molecule or a fragment thereof. For example, a fusion protein can comprise the amino acid of SEQ ID NO:3 and an Fc fragment (e.g., a human Fc fragment) (SEQ ID NO:64).

In another variation, a ZcytoR14 fusion protein comprises an IgG sequence, a ZcytoR14 moiety covalently joined to the aminoterminal end of the IgG sequence, and a signal peptide that is covalently joined to the aminoterminal of the ZcytoR14 moiety, wherein the IgG sequence consists of the following elements in the following order: a hinge region, a $CH_2$ domain, and a $CH_3$ domain. Accordingly, the IgG sequence lacks a $CH_1$ domain. The ZcytoR14 moiety displays a ZcytoR14 activity, as described herein, such as the ability to bind with a ZcytoR14 ligand. This general approach to producing fusion proteins that comprise both antibody and nonantibody portions has been described by LaRochelle et al., EP 742830 (WO 95/21258).

Fusion proteins comprising a ZcytoR14 moiety and an Fc moiety can be used, for example, as an in vitro assay tool. For example, the presence of a ZcytoR14 ligand in a biological sample can be detected using a ZcytoR14-immunoglobulin fusion protein, in which the ZcytoR14 moiety is used to bind the ligand, and a macromolecule, such as Protein A or anti-Fc antibody, is used to bind the fusion protein to a solid support. Such systems can be used to identify agonists and antagonists that interfere with the binding of a ZcytoR14 ligands, e.g., IL-17F or both IL-17A and IL-17F, to their receptor.

Other examples of antibody fusion proteins include polypeptides that comprise an antigen-binding domain and a ZcytoR14 fragment that contains a ZcytoR14 extracellular domain. Such molecules can be used to target particular tissues for the benefit of ZcytoR14 binding activity.

The present invention further provides a variety of other polypeptide fusions. For example, part or all of a domain(s) conferring a biological function can be swapped between ZcytoR14 of the present invention with the functionally equivalent domain(s) from another member of the cytokine receptor family. Polypeptide fusions can be expressed in recombinant host cells to produce a variety of ZcytoR14 fusion analogs. A ZcytoR14 polypeptide can be fused to two or more moieties or domains, such as an affinity tag for purification and a targeting domain. Polypeptide fusions can also comprise one or more cleavage sites, particularly between domains. See, for example, Tuan et al., *Connective Tissue Research* 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

ZcytoR14 binding domains can be further characterized by physical analysis of structure, as determined by such techniques as nuclear magnetic resonance, crystallography, electron diffraction or photoaffinity labeling, in conjunction with mutation of putative contact site amino acids of ZcytoR14 ligand agonists. See, for example, de Vos et al., *Science* 255: 306 (1992), Smith et al., *J. Mol. Biol.* 224:899 (1992), and Wlodaver et al., *FEBS Lett.* 309:59 (1992).

The present invention also contemplates chemically modified ZcytoR14 compositions, in which a ZcytoR14 polypeptide is linked with a polymer. Illustrative ZcytoR14 polypeptides are soluble polypeptides that lack a functional transmembrane domain, such as a polypeptide consisting of amino acid residues SEQ ID NO:3. Typically, the polymer is water soluble so that the ZcytoR14 conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce ZcytoR14 conjugates.

ZcytoR14 conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A ZcytoR14 conjugate can also comprise a mixture of such water-soluble polymers.

One example of a ZcytoR14 conjugate comprises a ZcytoR14 moiety and a polyalkyl oxide moiety attached to the N-terminus of the ZcytoR14 moiety. PEG is one suitable polyalkyl oxide. As an illustration, ZcytoR14 can be modified with PEG, a process known as "PEGylation." PEGylation of ZcytoR14 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, ZcytoR14 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a ZcytoR14 polypeptide. An example of an activated PEG ester is PEG esterified to N-hydroxysuccinimide. As used herein, the term "acylation" includes the following types of linkages between ZcytoR14 and a water soluble polymer: amide, carbamate, urethane, and the like. Methods for preparing PEGylated ZcytoR14 by acylation will typically comprise the steps of (a) reacting a ZcytoR14 polypeptide with PEG (such as a reactive ester of an aldehyde derivative of PEG) under conditions whereby one or more PEG groups attach to ZcytoR14, and (b) obtaining the reaction product(s). Generally, the optimal reaction conditions for acylation reactions will be determined based upon known parameters and desired results. For example, the larger the ratio of PEG:ZcytoR14, the greater the percentage of polyPEGylated ZcytoR14 product.

The product of PEGylation by acylation is typically a polyPEGylated ZcytoR14 product, wherein the lysine $\epsilon$-amino groups are PEGylated via an acyl linking group. An example of a connecting linkage is an amide. Typically, the resulting ZcytoR14 will be at least 95% mono-, di-, or tripegylated, although some species with higher degrees of PEGylation may be formed depending upon the reaction conditions. PEGylated species can be separated from unconjugated ZcytoR14 polypeptides using standard purification methods, such as dialysis, ultrafiltration, ion exchange chromatography, affinity chromatography, and the like.

PEGylation by alkylation generally involves reacting a terminal aldehyde derivative of PEG with ZcytoR14 in the presence of a reducing agent. PEG groups can be attached to the polypeptide via a —$CH_2$—NH group.

Moreover, anti-ZcytoR14 antibodies or antibody fragments of the present invention can be PEGylated using methods in the art and described herein.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the $\epsilon$-amino groups of the lysine residues and the $\alpha$-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of ZcytoR14 monopolymer conjugates.

Reductive alkylation to produce a substantially homogenous population of monopolymer ZcytoR14 conjugate molecule can comprise the steps of: (a) reacting a ZcytoR14 polypeptide with a reactive PEG under reductive alkylation conditions at a pH suitable to permit selective modification of the $\alpha$-amino group at the amino terminus of the ZcytoR14, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer ZcytoR14 conjugates, the reductive alkylation reaction conditions are those that permit the selective attachment of the water-soluble polymer moiety to the N-terminus of ZcytoR14. Such reaction conditions generally provide for pKa differences between the lysine amino groups and the $\alpha$-amino group at the N-terminus. The pH also affects the ratio of polymer to protein to be used. In general, if the pH is lower, a larger excess of polymer to protein will be desired because the less reactive the N-terminal $\alpha$-group, the more polymer is needed to achieve optimal conditions. If the pH is higher, the polymer:ZcytoR14 need not be as large because more reactive groups are available. Typically, the pH will fall within the range of 3 to 9, or 3 to 6. This method can be employed for making ZcytoR14-comprising homodimeric, heterodimeric or multimeric soluble receptor conjugates.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to ZcytoR14 will generally be in the range of 1:1 to 100:1. Typically, the molar ratio of water-soluble polymer to ZcytoR14 will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)). This method can be employed for making ZcytoR14-comprising homodimeric, heterodimeric or multimeric soluble receptor conjugates.

The present invention contemplates compositions comprising a peptide or polypeptide, such as a soluble receptor or antibody described herein. Such compositions can further comprise a carrier. The carrier can be a conventional organic or inorganic carrier. Examples of carriers include water, buffer solution, alcohol, propylene glycol, macrogol, sesame oil, corn oil, and the like.

G) Isolation of ZcytoR14 Polypeptides

The polypeptides of the present invention can be purified to at least about 80% purity, to at least about 90% purity, to at least about 95% purity, or greater than 95%, such as 96%, 97%, 98%, or greater than 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of ZcytoR14 purified from natural sources (e.g., human tissue sources), synthetic ZcytoR14 polypeptides, and recombinant ZcytoR14 polypeptides and fusion ZcytoR14 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in ZcytoR14 isolation and purification can be devised by those of skill in the art. For example, anti-ZcytoR14 antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification. Moreover, the ligand-binding properties of ZcytoR14 extracellular domain can be exploited for purification, for example, of ZcytoR14-comprising soluble receptors; for example, by using affinity chromatography wherein IL-17F ligand is bound to a column and the ZcytoR14-comprising receptor is bound and subsequently eluted using standard chromatography methods.

ZcytoR14 polypeptides or fragments thereof may also be prepared through chemical synthesis, as described above. ZcytoR14 polypeptides may be monomers or multimers; glycosylated or non-glycosylated; PEGylated or non-PEGylated; and may or may not include an initial methionine amino acid residue.

H) Production of Antibodies to ZcytoR14 Proteins

Antibodies to ZcytoR14 can be obtained, for example, using the product of a ZcytoR14 expression vector or ZcytoR14 isolated from a natural source as an antigen. Particularly useful anti-ZcytoR14 antibodies "bind specifically" with ZcytoR14. Antibodies are considered to be specifically binding if the antibodies exhibit at least one of the following two properties: (1) antibodies bind to ZcytoR14 with a threshold level of binding activity, and (2) antibodies do not significantly cross-react with polypeptides related to ZcytoR14.

With regard to the first characteristic, antibodies specifically bind if they bind to a ZcytoR14 polypeptide, peptide or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect ZcytoR14, but not presently known polypeptides using a standard Western blot analysis. Examples of known related polypeptides include known cytokine receptors.

Anti-ZcytoR14 antibodies can be produced using antigenic ZcytoR14 epitope-bearing peptides and polypeptides. Antigenic epitope-bearing peptides and polypeptides of the present invention contain a sequence of at least nine, or between 15 to about 30 amino acids contained within SEQ ID NO:2, SEQ ID NO:3, SEQ ID NO:5 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with ZcytoR14. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

As an illustration, potential antigenic sites in ZcytoR14 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549-586 (Plenum Press 1990), and Garnier-Robson, Garnier et al., *J. Mol. Biol.* 120: 97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible. Hopp/Woods hydrophilicity profiles can be used to determine regions that have the most antigenic potential within SEQ ID NO:3 (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. Moreover, ZcytoR14 antigenic epitopes within SEQ ID NO:3 as predicted by a Jameson-Wolf plot, e.g., using DNASTAR Protean program (DNASTAR, Inc., Madison, Wis.) serve as preferred antigenic epitopes, and can be determined by one of skill in the art. Such antigenic epitopes include (1) amino acid residue 73 to amino acid residue 82 of SEQ ID NO:3; (2) amino acid residue 95 to amino acid residue 104 of SEQ ID NO:3; (3) amino acid residue 111 to amino acid residue 119 of SEQ ID NO:3; (4) amino acid residue 179 to amino acid residue 186 of SEQ ID NO:3; (5) amino acid residue 200 to amino acid residue 205 of SEQ ID NO:3; (6) amino acid residue 229 to amino acid residue 236 of SEQ ID NO:3; (7) amino acid residue 264 to amino acid residue 268 of SEQ ID NO:3; and (8) amino acid residue 275 to amino acid residue 281 of SEQ ID NO:3. The present invention contemplates the use of any one of antigenic peptides X to Y to generate antibodies to ZcytoR14 or as a tool to screen or identify neutralizing monoclonal antibodies of the present invention. The present invention also contemplates polypeptides comprising at least one of antigenic peptides X to Y. The present invention contemplates the use of any antigenic peptides or epitopes described herein to generate antibodies to ZcytoR14, as well as to identify and screen anti-ZcytoR14 monoclonal antibodies that are neutralizing, and that may bind, block, inhibit, reduce, antagonize or neutralize the activity of IL-17F and IL-17A (individually or together).

Moreover, suitable antigens also include the ZcytoR14 polypeptides comprising a ZcytoR14 cytokine binding, or extracellular domain disclosed above in combination with another cytokine extracellular domain, such as a class I or II cytokine receptor domain, such as those that may form soluble ZcytoR14 heterodimeric or multimeric polypeptides, and the like.

Polyclonal antibodies to recombinant ZcytoR14 protein or to ZcytoR14 isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995). The immunogenicity of a ZcytoR14 polypeptide can be increased through the use of an adjuvant, such as alum (aluminum hydroxide) or Freund's complete or incomplete adjuvant. Polypeptides useful for immunization also include fusion polypeptides, such as fusions of ZcytoR14 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-ZcytoR14 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-ZcytoR14 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1-2.6.7 (John Wiley & Sons 1991) ["Coligan"], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a ZcytoR14 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-ZcytoR14 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of anti-ZcytoR14 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to ZcytoR14 polypeptide in vitro, and selecting antibody display libraries in phage or similar vectors (for instance, through use of immobilized or labeled ZcytoR14 protein or peptide). Genes encoding polypeptides having potential ZcytoR14 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the ZcytoR14 sequences disclosed herein to identify proteins which bind to ZcytoR14.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-ZcytoR14 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et al., U.S. Pat. No. 5,693,762 (1997).

Moreover, anti-ZcytoR14 antibodies or antibody fragments of the present invention can be PEGylated using methods in the art and described herein.

Polyclonal anti-idiotype antibodies can be prepared by immunizing animals with anti-ZcytoR14 antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-ZcytoR14 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

An anti-ZcytoR14 antibody can be conjugated with a detectable label to form an anti-ZcytoR14 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-ZcytoR14 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-ZcytoR14 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-ZcytoR14 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-ZcytoR14 immunoconjugates can be detectably labeled by linking an anti-ZcytoR14 antibody component to an enzyme. When the anti-ZcytoR14-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-ZcytoR14 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra.

Moreover, the convenience and versatility of immunochemical detection can be enhanced by using anti-ZcytoR14 antibodies that have been conjugated with avidin, streptavidin, and biotin (see, for example, Wilchek et al. (eds.), "Avidin-Biotin Technology," *Methods In Enzymology*, Vol. 184 (Academic Press 1990), and Bayer et al., "Immunochemical Applications of Avidin-Biotin Technology," in *Methods In Molecular Biology*, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

The present invention also contemplates kits for performing an immunological diagnostic assay for ZcytoR14 gene expression. Such kits comprise at least one container comprising an anti-ZcytoR14 antibody, or antibody fragment. A kit may also comprise a second container comprising one or more reagents capable of indicating the presence of ZcytoR14 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that ZcytoR14 antibodies or antibody fragments are used to detect ZcytoR14 protein. For example, written instructions may state that the enclosed antibody or antibody fragment can be used to detect ZcytoR14. The written material can be applied directly to a container, or the written material can be provided in the form of a packaging insert.

I) Use of Anti-ZcytoR14 Antibodies to Antagonize ZcytoR14 Binding to IL-17F or both IL-17A and IL-17F Alternative techniques for generating or selecting antibodies useful herein include in vitro exposure of lymphocytes to soluble ZcytoR14 receptor polypeptides or fragments thereof, such as antigenic epitopes, and selection of antibody display libraries in phage or similar vectors (for instance, through use of immobilized or labeled soluble ZcytoR14 receptor polypeptides or fragments thereof, such as antigenic epitopes). Genes encoding polypeptides having potential binding domains such as soluble ZcytoR14 receptor polypeptides or fragments thereof, such as antigenic epitopes can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides that interact with a known target that can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the soluble ZcytoR14 receptor polypeptides or fragments thereof, such as antigenic epitope polypeptide sequences disclosed herein to identify proteins which bind to ZcytoR14-comprising receptor polypeptides. These "binding polypeptides," which interact with soluble ZcytoR14-comprising receptor polypeptides, can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for binding, blocking, inhibiting, reducing, antagonizing or neutralizing interaction between IL-17A and IL-17F (individually or together) and ZcytoR14, or viral binding to a receptor. The binding polypeptides can also be used for diagnostic assays for determining circulating levels of soluble ZcytoR14-comprising receptor polypeptides; for detecting or quantitating soluble or non-soluble ZcytoR14-comprising receptors as marker of underlying pathology or disease. These binding polypeptides can also act as "antagonists" to block or inhibit soluble or membrane-bound ZcytoR14 monomeric receptor or ZcytoR14 homodimeric, heterodimeric or multimeric polypeptide binding (e.g. to ligand) and signal transduction in vitro and in vivo. Again, these binding polypeptides serve as anti-ZcytoR14 monomeric receptor or anti-ZcytoR14 homodimeric, heterodimeric or multimeric polypeptides and are useful for inhibiting IL-17F or both IL-17A and IL-17F activity, as well as receptor activity or protein-binding. Antibodies raised to the natural receptor complexes of the present invention, and ZcytoR14-epitope-binding antibodies, and anti-ZcytoR14 neutralizing monoclonal antibodies may be preferred embodiments, as they may act more specifically against the ZcytoR14 and can inhibit IL-17F or both IL-17A and IL-17F. Moreover, the antagonistic and binding activity of the antibodies of the present invention can be assayed in an IL-17A or IL-17F proliferation, signal trap, luciferase or binding assays in the presence of IL-17A or IL-17F respectively, and ZcytoR14-comprising soluble receptors, and other biological or biochemical assays described herein.

Antibodies to soluble ZcytoR14 receptor polypeptides (e.g., antibodies to SEQ ID NO:3) or fragments thereof, such as antigenic epitopes may be used for inhibiting the inflammatory effects of IL-17A, IL-17F, or both IL-17A and IL-17F in vivo, for therapeutic use against inflammation and inflammatory diseases such as psoriasis, psoriatic arthritis, rheumatoid arthritis, endotoxemia, inflammatory bowel disease (IBD), colitis, asthma, allograft rejection, immune mediated renal diseases, hepatobiliary diseases, multiple sclerosis, atherosclerosis, promotion of tumor growth, or degenerative joint disease and other inflammatory conditions disclosed herein; tagging cells that express ZcytoR14 receptors; for isolating soluble ZcytoR14-comprising receptor polypeptides by affinity purification; for diagnostic assays for determining circulating levels of soluble ZcytoR14-comprising receptor polypeptides; for detecting or quantitating soluble ZcytoR14-comprising receptors as marker of underlying pathology or disease; in analytical methods employing FACS; for screening expression libraries; for generating anti-idiotypic antibodies that can act as IL-17F or IL-17A agonists; and as neutralizing antibodies or as antagonists to bind, block, inhibit, reduce, or antagonize ZcytoR14 receptor function, or to bind, block, inhibit, reduce, antagonize or neutralize IL-17F and/or IL-17A activity (either individually or together) in vitro and in vivo. Suitable direct tags or labels include radionuclides, enzymes, substrates, cofactors, biotin, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to soluble ZcytoR14-comprising receptor polypeptides, or fragments thereof may be used in vitro to detect denatured or non-denatured ZcytoR14-comprising receptor polypeptides or fragments thereof in assays, for example, Western Blots or other assays known in the art.

Antibodies to soluble ZcytoR14 receptor or soluble ZcytoR14 homodimeric, heterodimeric or multimeric receptor polypeptides are useful for tagging cells that express the corresponding receptors and assaying their expression levels, for affinity purification, within diagnostic assays for determining circulating levels of receptor polypeptides, analytical methods employing fluorescence-activated cell sorting. Moreover, divalent antibodies, and anti-idiotypic antibodies may be used as agonists to mimic the effect of the ZcytoR14 ligand, IL-17F or IL-17A.

Antibodies herein can also be directly or indirectly conjugated to drugs, toxins, radionuclides and the like, and these conjugates used for in vivo diagnostic or therapeutic applications. For instance, antibodies or binding polypeptides which recognize soluble ZcytoR14 receptor or soluble ZcytoR14 homodimeric, heterodimeric or multimeric receptor polypeptides can be used to identify or treat tissues or organs that express a corresponding anti-complementary molecule (i.e., a ZcytoR14-comprising soluble or membrane-bound receptor). More specifically, antibodies to soluble ZcytoR14-comprising receptor polypeptides, or bioactive fragments or portions thereof, can be coupled to detectable or cytotoxic molecules and delivered to a mammal having cells, tissues or organs that express the ZcytoR14-comprising receptor such as ZcytoR14-expressing cancers.

Suitable detectable molecules may be directly or indirectly attached to polypeptides that bind ZcytoR14-comprising receptor polypeptides, such as "binding polypeptides," (including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, ZcytoR14 binding polypeptide-cytokine or antibody-cytokine fusion proteins can be used for enhancing in vivo killing of target tissues (for example, spleen, pancreatic, blood, lymphoid, colon, and bone marrow cancers), if the binding polypeptide-cytokine or anti-ZcytoR14 receptor antibody targets the hyperproliferative cell (See, generally, Hornick et al., *Blood* 89:4437-47, 1997). The described fusion proteins enable targeting of a cytokine to a desired site of action, thereby providing an elevated local concentration of cytokine. Suitable anti-ZcytoR14 monomer, homodimer, heterodimer or multimer antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, ZcytoR14 receptor binding polypeptides or antibody fusion proteins described herein can be used for enhancing in vivo killing of target tissues by directly stimulating a ZcytoR14 receptor-modulated apoptotic pathway, resulting in cell death of hyperproliferative cells expressing ZcytoR14-comprising receptors.

J) Therapeutic Uses of Polypeptides Having ZcytoR14 Activity or Antibodies to ZcytoR14

Amino acid sequences having soluble ZcytoR14 activity can be used to modulate the immune system by binding ZcytoR14 ligands IL-17A and IL-17F (either singly or together), and thus, preventing the binding of ZcytoR14 ligand with endogenous ZcytoR14 receptor. ZcytoR14 antagonists, such as soluble ZcytoR14 or anti-ZcytoR14 antibodies, can also be used to modulate the immune system by inhibiting the binding of ZcytoR14 ligand with the endogenous ZcytoR14 receptor. Accordingly, the present invention includes the use of proteins, polypeptides, and peptides having ZcytoR14 activity (such as soluble ZcytoR14 polypeptides, ZcytoR14 polypeptide fragments, ZcytoR14 analogs (e.g., anti-ZcytoR14 anti-idiotype antibodies), and ZcytoR14 fusion proteins) to a subject which lacks an adequate amount of this polypeptide, or which produces an excess of ZcytoR14 ligand. ZcytoR14 antagonists (e.g., anti-ZcytoR14 antibodies) can be also used to treat a subject which produces an excess of either ZcytoR14 ligand or ZcytoR14. Suitable subjects include mammals, such as humans. For example, such ZcytoR14 polypeptides and anti-ZcytoR14 antibodies are useful in binding, blocking, inhibiting, reducing, antagonizing or neutralizing IL-17A and IL-17F (either singly or together), in the treatment of inflammation and inflammatory diseases such as psoriasis, psoriatic arthritis, rheumatoid arthritis, endotoxemia, inflammatory bowel disease (IBD), colitis, asthma, allograft rejection, immune mediated renal diseases, hepatobiliary diseases, multiple sclerosis, atherosclerosis, promotion of tumor growth, or degenerative joint disease and other inflammatory conditions disclosed herein.

Within preferred embodiments, the soluble receptor form of ZcytoR14, SEQ ID NO:3) is a monomer, homodimer, heterodimer, or multimer that binds to, blocks, inhibits, reduces, antagonizes or neutralizes IL-17F and IL-17A (individually or together) in vivo. Antibodies and binding polypeptides to such ZcytoR14 monomer, homodimer, heterodimer, or multimers also serve as antagonists of ZcytoR14 activity, and as IL-17A and IL-17F antagonists (singly or together), as described herein.

In addition, we have described herein that both polyclonal and monoclonal neutralizing anti-IL-17F antibodies bind to, block, inhibit, reduce, antagonize or neutralize IL-17F and IL-17A activity in cell based neutralization assays. Analysis of the tissue distribution of the mRNA corresponding ZcytoR14 cDNA showed that mRNA the ZcytoR14 gene is strongly expressed in thyroid, adrenal gland, prostate, and liver tissues, and expressed to a lesser extent in heart, small intestine, stomach, and trachea tissues. In particular, ZcytoR14 is consistently expressed in non-T cell peripheral blood cell lines, including monocytes, B-cells, and cells of the myeloid lineage. Also, ZcytoR14 mRNA is reliably expressed in cell lines derived from skin. Other cell lines that express ZcytoR14 are all 5 of the large intestine cell lines that were present on the array. In contrast, there is little or no expression in brain, placenta, lung, skeletal muscle, kidney, pancreas, spleen, thymus, testis, ovary, colon, peripheral blood leukocytes, spinal cord, lymph node, and bone marrow. The ligand to which ZcytoR14 binds (IL-17F and/or IL-17A) is implicated in inducing inflammatory response and contributing to inflammatory diseases, primarily via its ability to enhance production of inflammatory mediators, including IL-1b, IL-6 and TNF-a, as well as those mediators that are involved in the proliferation, maturation and chemotaxis of neutrophils (reviewed in Witowski et al. Cell. Mol. Life. Sci. 61:567-579 [2004]).

Thus, particular embodiments of the present invention are directed toward use of soluble ZcytoR14 and anti-ZcytoR14 antibodies as antagonists in inflammatory and immune diseases or conditions such as psoriasis, psoriatic arthritis, atopic dermatitis, inflammatory skin conditions, rheumatoid arthritis, inflammatory bowel disease (IBD), Crohn's Disease, diverticulosis, asthma, pancreatitis, type I diabetes (IDDM), pancreatic cancer, pancreatitis, Graves Disease, colon and intestinal cancer, autoimmune disease, sepsis, organ or bone marrow transplant; inflammation due to endotoxemia, trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-17F or IL-17A cytokines is desired.

Moreover, antibodies or binding polypeptides that bind ZcytoR14 polypeptides described herein, and ZcytoR14 polypeptides themselves are useful to:

1) Block, inhibit, reduce, antagonize or neutralize signaling via IL-17A or IL-17F receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

2) Block, inhibit, reduce, antagonize or neutralize signaling via IL-17A or IL-17F receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via ZcytoR14. Alternatively antibodies, such as monoclonal antibodies (MAb) to ZcytoR14-comprising receptors, can also be used as an antagonist to deplete unwanted immune cells to treat autoimmune disease. Asthma, allergy and other atopic disease may be treated with an MAb against, for example, soluble ZcytoR14 soluble receptors to inhibit the immune response or to deplete offending cells. Blocking, inhibiting, reducing, or antagonizing signaling via ZcytoR14, using the polypeptides and antibodies of the present invention, may also benefit diseases of the pancreas, kidney, pituitary and neuronal cells. IDDM, NIDDM, pancreatitis, and pancreatic carcinoma may benefit. ZcytoR14 may serve as a target for MAb therapy of cancer where an antagonizing MAb inhibits cancer growth and targets immune-mediated killing. (Holliger P, and Hoogenboom, H: Nature Biotech. 16: 1015-1016, 1998). Mabs to soluble ZcytoR14 may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

3) Agonize, enhance, increase or initiate signaling via IL-17A or IL-17F receptors in the treatment of autoimmune diseases such as IDDM, MS, SLE, myasthenia gravis, rheumatoid arthritis, and IBD. Anti-ZcytoR14 neutralizing and monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., J. Immunol. 160:4841-4849, 1998). Similarly, agonistic anti-soluble ZcytoR14 monomers, homodimers, heterodimers and multimer monoclonal antibodies may be used to signal, deplete and deviate immune cells involved in asthma, allergy and atopoic disease. Signaling via ZcytoR14 may also benefit diseases of the pancreas, kidney, pituitary and neuronal cells. IDDM, NIDDM, pancreatitis, and pancreatic carcinoma may benefit. ZcytoR14 may serve as a target for MAb therapy of pancreatic cancer where a signaling MAb inhibits cancer growth and targets immune-mediated killing (Tutt, A L et al., J. Immunol 161: 3175-3185, 1998). Similarly renal cell carcinoma may be treated with monoclonal antibodies to ZcytoR14-comprising soluble receptors of the present invention.

Soluble ZcytoR14 polypeptides described herein can be used to bind, block, inhibit, reduce, antagonize or neutralize IL-17F or IL-17A activity, either singly or together, in the treatment of autoimmune disease, atopic disease, NIDDM, pancreatitis and kidney dysfunction as described above. A soluble form of ZcytoR14 may be used to promote an antibody response mediated by Th cells and/or to promote the production of IL-4 or other cytokines by lymphocytes or other immune cells.

The soluble ZcytoR14-comprising receptors of the present invention are useful as antagonists of IL-17A or IL-17F cytokine. Such antagonistic effects can be achieved by direct neutralization or binding of IL-17A or IL-17F. In addition to antagonistic uses, the soluble receptors of the present invention can bind IL-17F and act as carrier proteins for IL-17A or IL-17F cytokine, in order to transport the ligand to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, or tumor. For example, in acute infection or some cancers, benefit may result from induction of inflammation and local acute phase response proteins by the action of IL-17F. Thus, the soluble receptors of the present invention can be used to specifically direct the action of IL-17A or IL-17F. See, Cosman, D. *Cytokine* 5: 95-106, 1993; and Fernandez-Botran, R. *Exp. Opin. Invest. Drugs* 9:497-513, 2000.

Moreover, the soluble receptors of the present invention can be used to stabilize the IL-17F or IL-17A, to increase the bioavailability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp130 receptor. See, Cosman, D. supra., and Fernandez-Botran, R. supra. Moreover, ZcytoR14 may be combined with a cognate ligand such as IL-17F to comprise a ligand/soluble receptor complex. Such complexes may be used to stimulate responses from cells presenting a companion receptor subunit such as, for example, pDIRS1 (IL-17ARB) or CRF2-4 (IL-10RB). The cell specificity of ZcytoR14/ligand complexes may differ from that seen for the ligand administered alone. Furthermore the complexes may have distinct pharmacokinetic properties such as affecting half-life, dose/response and organ or tissue specificity. ZcytoR14/IL-17F or ZcytoR14/IL-17A complexes thus may have agonist activity to enhance an immune response or stimulate mesangial cells or to stimulate hepatic cells. Alternatively only tissues expressing a signaling subunit the heterodimerizes with the complex may be affected analogous to the response to IL6/IL6R complexes (Hirota H. et al., *Proc. Nat'l. Acad. Sci.* 92:4862-4866, 1995; Hirano, T. in Thomason, A. (Ed.) "The Cytokine Handbook", $3^{rd}$ Ed., p. 208-209). Soluble receptor/cytokine complexes for IL-12 and CNTF display similar activities.

Moreover Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, arthritis, rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory proteins, such as ZcytoR14, and anti-ZcytoR14 antibodies, could have crucial therapeutic potential for a vast number of human and animal diseases, from asthma and allergy to autoimmunity and septic shock.

1. Arthritis

Arthritis, including osteoarthritis, rheumatoid arthritis, arthritic joints as a result of injury, and the like, are common inflammatory conditions which would benefit from the therapeutic use of anti-inflammatory proteins, such as ZcytoR14 polypeptides of the present invention. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002). One of those mediators could be IL-17A or IL-17F, and as such a molecule that binds or inhibits IL-17F or IL-17A activity, such as soluble ZcytoR14, ZcytoR14 polypeptides, or anti ZcytoR14 antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol* 92:8955-959, 1995).

One group has shown that an anti-mouse IL-17 antibody reduces symptoms in a mouse CIA-model relative to control mice, thus showing conceptually that soluble Zcytor14-Fc may be beneficial in treating human disease. The administration of a single mouse-IL-17-specific rat antisera reduced the symptoms of arthritis in the animals when introduced prophylactically or after symptoms of arthritis were already present in the model (Lubberts et al, *Arthritis Rheum.* 50:650-9, 2004). Therefore, Zcytor14-Fc can be used to neutralize IL-17A and/or IL-17F in the treatment of specific human diseases such as arthritis, psoriasis, psoriatic arthritis, endotoxemia, inflammatory bowel disease (IBD), colitis, and other inflammatory conditions disclosed herein.

The administration of soluble ZcytoR14 comprising polypeptides (ZcytoR14), such as ZcytoR14-Fc4 or other ZcytoR14 soluble and fusion proteins to these CIA model mice is used to evaluate the use of soluble ZcytoR14 as an antagonist to IL-17F used to ameliorate symptoms and alter the course of disease. Moreover, results showing inhibition of IL-17F by ZcytoR14 would provide proof of concept that other IL-17F antagonists, such as soluble ZcytoR14 or neutralizing antibodies thereto, can also be used to ameliorate symptoms and alter the course of disease. Furthermore, since IL-17A and/or IL-17F induces production of IL-1b and TNF-a, both of which are implicated in the pathogenesis and progression of rheumatoid arthritis, the systemic or local administration of soluble ZcytoR14 comprising polypeptides, such as ZcytoR14-Fc4 or other IL-17F soluble receptors (e.g., ZcytoR14; SEQ ID NO:3) and anti-ZcytoR14 antibodies, and fusion proteins can potentially suppress the inflammatory response in RA. By way of example and without limitation, the injection of 10-200 ug Zcytor14-Fc per mouse (one to seven times a week for up to but not limited to 4 weeks via s.c., i.p., or i.m route of administration) can significantly reduce the disease score (paw score, incident of inflammation, or disease). Depending on the initiation of Zcytor14-Fc administration (e.g. prior to or at the time of collagen immunization, or at any time point following the second collagen immunization, including those time points at which the disease has already progressed), Zcytor14 can be efficacious in preventing rheumatoid arthritis, as well as preventing its progression. Other potential therapeutics include ZcytoR14 polypeptides, anti-ZcytoR14 antibodies, or anti IL-17F antibodies or binding partners, and the like.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory proteins, such as ZcytoR14 polypeptides and antibodies of the present invention, could aid in preventing and treating endotoxemia in humans and animals. ZcytoR14 polypeptides, or anti-ZcytoR14 antibodies or binding partners, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., Lancet 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. Cell 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., Science 229:869, 1985). It is well established that 1 ug injection of E. coli LPS into a C57Bl/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., Science 229:869, 1985). The potential immunointervention strategies for the prevention and/or treatment of septic shock include anti-TNF mAb, IL-1 receptor antagonist, LIF, IL-10, and G-CSF.

The administration of soluble ZcytoR14 comprising polypeptides, such as ZcytoR14-Fc4 or other ZcytoR14 soluble and fusion proteins to these LPS-induced model may be used to evaluate the use of ZcytoR14 to ameliorate symptoms and alter the course of LPS-induced disease. Moreover, results showing inhibition of IL-17F by ZcytoR14 provide proof of concept that other IL-17F antagonists, such as soluble ZcytoR14 or antibodies thereto, can also be used to ameliorate symptoms in the LPS-induced model and alter the course of disease. The model will show induction of IL-17F by LPS injection and the potential treatment of disease by ZcytoR14 polypeptides. Since LPS induces the production of pro-inflammatory factors possibly contributing to the pathology of endotoxemia, the neutralization of IL-17F activity or other pro-inflammatory factors by an antagonist ZcytoR14 polypeptide can be used to reduce the symptoms of endotoxemia, such as seen in endotoxic shock. Other potential therapeutics include ZcytoR14 polypeptides, anti-ZcytoR14 antibodies, or binding partners, and the like.

3. Inflammatory Bowel Disease IBD

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. ZcytoR14 polypeptides, anti-ZcytoR14 antibodies, or binding partners, could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. Intern. Rev. Immunol 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of soluble ZcytoR14 comprising polypeptides, such as ZcytoR14-Fc4 or other ZcytoR14 soluble and fusion proteins to these TNBS or DSS models can be used to evaluate the use of soluble ZcytoR14 to ameliorate symptoms and alter the course of gastrointestinal disease. Moreover, the results showing inhibition of IL-17F by ZcytoR14 provide proof of concept that other IL-17F antagonists, such as soluble ZcytoR14 or antibodies thereto, can also be used to ameliorate symptoms in the colitis/IBD models and alter the course of disease.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. ZcytoR14 polypeptides, anti-ZcytoR14 antibodies, or binding partners, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

ZcytoR14 soluble receptor polypeptides and antibodies thereto may also be used within diagnostic systems for the detection of circulating levels of IL-17F or IL-17A ligand, and in the detection of IL-17F associated with acute phase inflammatory response. Within a related embodiment, antibodies or other agents that specifically bind to ZcytoR14 soluble receptors of the present invention can be used to detect circulating receptor polypeptides; conversely, ZcytoR14 soluble receptors themselves can be used to detect circulating or locally-acting IL-17F or IL-17A polypeptides. Elevated or depressed levels of ligand or receptor polypeptides may be indicative of pathological conditions, including inflammation or cancer. IL-17F is known to induce associated acute phase inflammatory response. Moreover, detection of acute phase proteins or molecules such as IL-17A or IL-17F can be indicative of a chronic inflammatory condition in certain disease states (e.g., asthma, psoriasis, rheumatoid arthritis, colitis, IBD). Detection of such conditions serves to aid in disease diagnosis as well as help a physician in choosing proper therapy.

In utero administration of soluble ZcytoR14 can be used to show efficacy in vivo in disease models by reducing or eliminating the phenotype associated with IL-17F transgenic pups which over express IL-17F, or IL-17A transgenic pups which over express IL-17A. There are precedents in the art for in utero treatment with antagonists such as neutralizing monoclonal antibodies (mAbs). In one case, the development of the B-1 subset of B cells was dramatically affected by treating pregnant female mice with a mAb specific for the B cell-specific molecule, CD19 (e.g., Krop I. Et al., *Eur. J. Immunol.* 26(1):238-42, 1996). Krop et al. injected timed pregnant mice intraperitoneally with 500 ug of rat anti-mouse CD19 mAb (or a rat isotype-matched control Ab) in PBS beginning on day 9 of gestation, with subsequent injections every other day until birth. Pups were also injected once with 500 ug of these antibodies at 10 days of age. In another case, Tanaka et al., found that in utero treatment with monoclonal antibody to IL-2 receptor beta-chain completely abrogates development of Thy-1+ dendritic epidermal cells. The two distinct subunits of the IL-2 receptor, i.e. the alpha-chain (IL-2R alpha) and the beta-chain (IL-2R beta), are expressed in an almost mutually exclusive fashion throughout fetal thymus ontogeny. Blocking IL-2R beta, a signal transducing component of IL-2R, by administering a neutralizing mAb to IL-2R beta, resulted in the complete and selective disappearance of Thy-1+ skin dendritic epidermal cells. Development of any other T cell subsets was uncompromised. This indicated that IL-2 plays a crucial role in the development of fetal V gamma 5+ cells and their descendants (see, Tanaka, T. et al., *Int Immunol* 4(4): 487-9, 1992). In addition, Schattemann G C et al., showed that PDGF-A is required for normal murine cardiovascular development using an in utero system. Several lines of evidence suggest that platelet-derived growth factor A chain (PDGF-A) is required for normal embryonic cardiovascular development. Introduction of anti-PDGF-A neutralizing antibodies into mouse deciduas in utero resulted in the selective disruption of PDGF-A ligand-receptor interactions in vivo for a period of 18-24 hr and allowed assessment of whether PDGF-A is required for cardiovascular development and when it is required (see, Schattemann G C et al., *Dev. Biol.* 176(1):133-42, 1996). These results, as well as others described in the art, provide evidence that antagonists such as neutralizing mAbs or soluble receptors can elicit strong effects in utero. Similarly, data showing the efficacy of soluble receptors and/or neutralizing IL-17A or IL-17F with monoclonal antibodies in vivo in disease models to reduce or eliminate the skin phenotype found in IL-17A and IL-17F transgenic pups which over express IL-17A and IL-17F respectively can be shown.

In addition to other disease models described herein, the activity of soluble ZcytoR14 and/or anti-ZcytoR14 antibodies on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, *Leuk. Res.* 18:513-22, 1994 and Flavell, D J, *Hematological Oncology* 14:67-82, 1996. As an in vivo xenograft model for psoriasis, human psoriatic skin tissue is implanted into the SCID mouse model, and challenged with an appropriate antagonist. Moreover, other psoriasis animal models in the art may be used to evaluate IL-17A and IL-17F antagonists, such as human psoriatic skin grafts implanted into AGR129 mouse model, and challenged with an appropriate antagonist (e.g., see, Boyman, O. et al., *J. Exp. Med.* Online publication #20031482, 2004, incorporated herein by reference). Soluble ZcytoR14 or Anti-ZcytoR14 antibodies that bind, block, inhibit, reduce, antagonize or neutralize the activity of IL-17F or both IL-17A and IL-17F are preferred antagonists, however, anti-IL-17A and anti-IL-22 antibodies (alone or in combination), soluble ZcytoR14, as well as other IL-17A and IL-17F antagonists can be used in this model. Similarly, tissues or cells derived from human colitis, IBD, arthritis, or other inflammatory lesions can be used in the SCID model to assess the anti-inflammatory properties of the IL-17A and IL-17F antagonists described herein.

Therapies designed to abolish, retard, or reduce inflammation using soluble ZcytoR14, anti-ZcytoR14 antibodies or its derivatives, agonists, conjugates or variants can be tested by administration of anti-ZcytoR14 antibodies or soluble ZcytoR14 compounds to SCID mice bearing human inflammatory tissue (e.g., psoriatic lesions and the like), or other models described herein. Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253, 2001; Zollner, T. M. et al. *J. Clin. Invest.* 109:671, 2002; Yamanaka, N. et al. *Microbiol Immunol* 45:507, 2001; Raychaudhuri, S. P. et al. *Br. J. Dermatol.* 144:931, 2001; Boehncke, W. H et al. *Arch. Dermatol. Res.* 291:104, 1999; Boehncke, W. H et al. *J. Invest. Dermatol.* 116:596, 2001; Nickoloff, B. J. et al. *Am. J. Pathol.* 146:580, 1995; Boehncke, W. H et al. *J. Clin. Pathol.* 24:1, 1997; Sugai, J., M. et al. *J. Dermatol. Sci.* 17:85, 1998; and Villadsen L. S. et al. *J. Clin. Invest.* 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model. For example, therapeutic strategies appropriate for testing in such a model include direct treatment using soluble ZcytoR14, anti-ZcytoR14 antibodies, other IL-17A and IL-17F antagonists (singly or together), or related conjugates or antagonists based on the disrupting interaction of soluble ZcytoR14 with its ligands IL-17A and IL-17F, or for cell-based therapies utilizing soluble ZcytoR14 or anti-ZcytoR14 antibodies or its derivatives, agonists, conjugates or variants.

Moreover, Psoriasis is a chronic inflammatory skin disease that is associated with hyperplastic epidermal keratinocytes and infiltrating mononuclear cells, including CD4+ memory T cells, neutrophils and macrophages (Christophers, *Int. Arch. Allergy Immunol,* 110:199, 1996). It is currently believed that environmental antigens play a significant role in initiating and contributing to the pathology of the disease. However, it is the loss of tolerance to self-antigens that is thought to mediate the pathology of psoriasis. Dendritic cells and CD4+ T cells are thought to play an important role in antigen presentation and recognition that mediate the immune response leading to the pathology. We have recently developed a model of psoriasis based on the CD4+ CD45RB transfer model (Davenport et al., *Internat. Immunopharmacol.,* 2:653-672). Soluble ZcytoR14 or anti-ZcytoR14 antibodies of the present invention are administered to the mice Inhibition of disease scores (skin lesions, inflammatory cytokines) indicates the effectiveness of IL-17A and IL-17F antagonists in psoriasis, e.g., anti-ZcytoR14 antibodies or ZcytoR14 soluble receptors.

5. Atopic Dermatitis.

AD is a common chronic inflammatory disease that is characterized by hyperactivated cytokines of the helper T cell subset 2 (Th2). Although the exact etiology of AD is unknown, multiple factors have been implicated, including hyperactive Th2 immune responses, autoimmunity, infection, allergens, and genetic predisposition. Key features of the disease include xerosis (dryness of the skin), pruritus (itchiness of the skin), conjunctivitis, inflammatory skin lesions, *Staphylococcus aureus* infection, elevated blood eosinophilia, elevation of serum IgE and IgG1, and chronic dermatitis with T cell, mast cell, macrophage and eosinophil infiltration. Colonization or infection with *S. aureus* has been recognized to exacerbate AD and perpetuate chronicity of this skin disease.

AD is often found in patients with asthma and allergic rhinitis, and is frequently the initial manifestation of allergic disease. About 20% of the population in Western countries suffer from these allergic diseases, and the incidence of AD in developed countries is rising for unknown reasons. AD typically begins in childhood and can often persist through adolescence into adulthood. Current treatments for AD include topical corticosteroids, oral cyclosporin A, non-corticosteroid immunosuppressants such as tacrolimus (FK506 in ointment form), and interferon-gamma. Despite the variety of treatments for AD, many patients' symptoms do not improve, or they have adverse reactions to medications, requiring the search for other, more effective therapeutic agents. The soluble ZcytoR14 polypeptides and anti-ZcytoR14 antibodies of the present invention, including the neutralizing anti-human ZcytoR14 antibodies of the present invention, can be used to neutralize IL-17F and IL-17A in the treatment of specific human diseases such as atoptic dermatitis, inflammatory skin conditions, and other inflammatory conditions disclosed herein.

6. Asthma

IL-17 plays an important role in allergen-induced T cell activation and neutrophilic influx in the airways. The receptor for IL-17 is expressed in the airways (Yao, et al. Immunity 3:811 (1995)) and IL-17 mediated neutrophil recruitment in allergic asthma is largely induced by the chemoattractant IL-8, GRO-$\alpha$ and macrophage inflammatory protein-2 (MIP-2) produced by IL-17 stimulated human bronchial epithelial cells (HBECs) and human bronichial fibroblasts (Yao, et al. *J Immunol* 155:5483 (1995)); Molet, et al. *J Allergy Clin Immunol* 108:430 (2001)). IL-17 also stimulates HBECs to release IL-6, a neutrophil-activating factor (Fossiez, et al, *J Exp Med* 183:2593 (1996), and Linden, et al. *Int Arch Allergy Immunol* 126:179 (2001)) and has been shown to synergize with TNF-$\alpha$ to prolong the survival of human neutrophils in vitro (Laan, et al. *Eur Respir J* 21:387 (2003)). Moreover, IL-17 is capable of amplifying the inflammatory responses in asthma by its ability to enhance the secretion of cytokines implicated in airway remodeling such as the profibrotic cytokines, IL-6 and IL-11 and inflammatory mediators granulocyte colony-stimulating factor (G-CSF) and granulocyte macrophage colony-stimulating factor (GM-CSF) (Molet, et al. *J Allergy Clin Immunol* 108:430 (2001)).

Clinical evidence shows that acute, severe exacerbations of asthma are associated with recruitment and activation of neutrophils in the airways, thus IL-17 is likely to play a significant role in asthma. Patients with mild asthma display a detectable increase in the local concentration of free, soluble IL-17A protein (Molet, et al. J Allergy Clin Immunol 108:430 (2001)) while healthy human volunteers with induced, severe airway inflammation due to the exposure to a swine confinement, display a pronounced increase in the concentration of free, soluble IL-17A protein in the bronchoalveolar space (Fossiez, et al, J Exp Med 183:2593 (1996), and Linden, et al. Int Arch Allergy Immunol 126:179 (2001)). Furthermore, IL-17 levels in sputum have correlated with individuals who have increased airway hyper-reactivity Barczyk, et al. Respir Med 97:726 (2003).

In animal models of airway hyper-responsiveness, chronic inhalation of ovalbumin by sensitized mice resulted in bronchial eosinophilic inflammation and early induction of IL-17 mRNA expression in inflamed lung tissue, together with a bronchial neutrophilia Hellings, et al. Am J Respir Cell Mol Biol 28:42 (2003). Anti-IL-17 monoclonal antibodies strongly reduced bronchial neutrophilic influx but significantly enhanced IL-5 levels in both bronchoalveolar lavage fluid and serum, and aggravated allergen-induced bronchial eosinophilic influx, suggesting that IL-17A may be involved in determining the balance between neutrophil and eosinophil accumulation following antigen insult Id.

Among the IL-17 family members, IL-17F is most closely related to IL-17A. The biological activities mediated by IL-17F are similar to those of IL-17A, where IL-17F stimulates production of IL-6, IL-8 and G-CSF Hurst, et al. J Immunol 169:443 (2002). IL-17F also induces production of IL-2, transforming growth factor (TGF)-, and monocyte chemoattractant protein (MCP) in endothelial cells Starnes, et al. J Immunol 167:4137 (2001). Similarly, allergen challenge can increase local IL-17F in patients with allergic asthma Kawaguchi, et al. J Immunol 167:4430 (2001). Gene delivery of IL-17F in murine lung increases neutrophils in the bronchoalveolar space, while mucosal transfer of the IL-17F gene enhances the levels of Ag-induced pulmonary neutrophilia and airway responsiveness to methacholine Oda, et al. Am J Respir Crit. Care Med 171:12 (2005).

Apart from asthma, several chronic inflammatory airway diseases are characterized by neutrophil recruitment in the airways and IL-17 has been reported to play an important role in the pathogenesis of respiratory conditions such as chronic obstructive pulmonary disease (COPD), bacterial pneumonia and cystic fibrosis (Linden, et al. Eur Respir J 15:973 (2000), Ye, et al. Am J Respir Cell Mol Biol 25:335 (2001), Rahman, et al. Clin Immunol 115:268 (2005)). An anti-IL-17A and/or anti-IL-17F therapeutic molecule could be demonstrated to be efficacious for chronic inflammatory airway disease in an in vitro model of inflammation. The ability of antagonists to IL-17F and/or IL-17A activity, such as ZcytoR14 soluble receptors and antibodies thereto including the anti-human-ZcytoR14 monoclonal and neutralizing antibodies of the present invention to inhibit IL-17A or and/or IL-17F-induced cytokine and chemokine production from cultured HBECs or bronchial fibroblasts could be used as a measure of efficacy for such antagonists in the prevention of the production of inflammatory mediators directly resulting from IL-17A and/or F stimulation. If the addition of antagonists to IL-17F and/or IL-17A activity, such as ZcytoR14 soluble receptors and antibodies thereto including the anti-human-ZcytoR14 monoclonal and neutralizing antibodies of the present invention markedly reduces the production and expression of inflammatory mediators, it would be expected to be efficacious in inflammatory aspects associated with chronic airway inflammation.

For pharmaceutical use, the soluble ZcytoR14 or anti-ZcytoR14 antibodies of the present invention are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. When utilizing such a combination therapy, the cytokines may be combined in a single formulation or may be administered in separate formulations. Methods of formulation are well known in the art and are disclosed, for example, in Remington's Pharmaceutical Sciences, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of soluble ZcytoR14 or anti-ZcytoR14 antibodies of the present invention is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The soluble ZcytoR14 or anti-ZcytoR14 antibodies of the present invention can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

Generally, the dosage of administered soluble ZcytoR14 (or ZcytoR14 analog or fusion protein) or anti-ZcytoR14 antibodies will vary depending upon such factors as the patient's age, weight, height, sex, general medical condition and previous medical history. Typically, it is desirable to provide the recipient with a dosage of soluble ZcytoR14 or anti-ZcytoR14 antibodies which is in the range of from about 1 pg/kg to 10 mg/kg (amount of agent/body weight of patient), although a lower or higher dosage also may be administered as circumstances dictate.

Administration of soluble ZcytoR14 or anti-ZcytoR14 antibodies to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in Protein Delivery: Physical Systems, Sanders and Hendren (eds.), pages 255-288 (Plenum Press 1997)). The feasibility of an intranasal delivery is exemplified by such a mode of insulin administration (see, for example, Hinchcliffe and Illum, Adv. Drug Deliv. Rev. 35:199 (1999)). Dry or liquid particles comprising soluble ZcytoR14 or anti-ZcytoR14 antibodies can be prepared and inhaled with the aid of dry-powder dispersers, liquid aerosol generators, or nebulizers (e.g., Pettit and Gombotz, TIBTECH 16:343 (1998); Patton et al., Adv. Drug Deliv. Rev. 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a molecule having ZcytoR14 binding activity (Potts et al., *Pharm. Biotechnol.* 10:213 (1997)).

A pharmaceutical composition comprising a soluble ZcytoR14 or anti-ZcytoR14 antibody can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, soluble ZcytoR14 or anti-ZcytoR14 antibody molecules and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising ZcytoR14 (or ZcytoR14 analog or fusion protein) or neutralizing anti-ZcytoR14 antibody can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N. Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides and antibodies can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly(ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having binding ZcytoR14 activity such as ZcytoR14 monomeric, homodimeric, heterodimeric or multimeric soluble receptors, and ZcytoR14 antagonists, for example anti-ZcytoR14 antibodies or binding polypeptides, or neutralizing anti-ZcytoR14 antibodies, which a polypeptide is linked with a polymer, as discussed above.

Other dosage forms can be devised by those skilled in the art, as shown, for example, by Ansel and Popovich, *Pharmaceutical Dosage Forms and Drug Delivery Systems,* 5th Edition (Lea & Febiger 1990), Gennaro (ed.), *Remington's Pharmaceutical Sciences,* 19th Edition (Mack Publishing Company 1995), and by Ranade and Hollinger, *Drug Delivery Systems* (CRC Press 1996).

As an illustration, pharmaceutical compositions may be supplied as a kit comprising a container that comprises a polypeptide with a ZcytoR14 extracellular domain, e.g., ZcytoR14 monomeric, homodimeric, heterodimeric or multimeric soluble receptors, or a ZcytoR14 antagonist (e.g., an antibody or antibody fragment that binds a ZcytoR14 polypeptide, or neutralizing anti-ZcytoR14 antibody). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the ZcytoR14 composition is contraindicated in patients with known hypersensitivity to ZcytoR14.

A pharmaceutical composition comprising Anti-ZcytoR14 antibodies or binding partners (or Anti-ZcytoR14 antibody fragments, antibody fusions, humanized antibodies and the like), or ZcytoR14 soluble receptor, can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Anti-ZcytoR14 neutralizing antibodies and binding partners with IL-17F OR IL-17A binding activity, or ZcytoR14 soluble receptor, can be encapsulated within liposomes using standard techniques of protein microencapsulation (see, for example, Anderson et al., *Infect. Immun* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly(ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified Anti-ZcytoR14 antibody or binding partner, for example anti-Anti-ZcytoR14 antibodies or ZcytoR14 soluble receptor, linked with a polymer, as discussed above.

Other dosage forms can be devised by those skilled in the art, as shown, for example, by Ansel and Popovich, *Pharmaceutical Dosage Forms and Drug Delivery Systems,* 5$^{th}$ Edition (Lea & Febiger 1990), Gennaro (ed.), *Remington's Pharmaceutical Sciences,* 19$^{th}$ Edition (Mack Publishing Company 1995), and by Ranade and Hollinger, *Drug Delivery Systems* (CRC Press 1996).

The present invention contemplates compositions of anti-IL-17F antibodies, and methods and therapeutic uses comprising an antibody, peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

K) Production of Transgenic Mice

Transgenic mice can be engineered to over-express the either IL-17F, IL-17A or the Zcytor14 gene in all tissues or under the control of a tissue-specific or tissue-preferred regulatory element. These over-producers can be used to characterize the phenotype that results from over-expression, and the transgenic animals can serve as models for human disease caused by excess IL-17F, IL-17A or Zcytor14. Transgenic mice that over-express any of these also provide model bioreactors for production of Zcytor14, such as soluble Zcytor14, in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), Monastersky and Robl (eds.), *Strategies in Transgenic Animal Science* (ASM Press 1995), and Abbud and Nilson, "Recombinant Protein Expression in Transgenic Mice," in *Gene Expression Systems: Using Nature for the Art of Expression*, Fernandez and Hoeffler (eds.), pages 367-397 (Academic Press, Inc. 1999)).

For example, a method for producing a transgenic mouse that expresses a Zcytor14 gene can begin with adult, fertile males (studs) (B6C3f1, 2-8 months of age (Taconic Farms, Germantown, N.Y.)), vasectomized males (duds) (B6D2f1, 2-8 months, (Taconic Farms)), prepubescent fertile females (donors) (B6C3f1, 4-5 weeks, (Taconic Farms)) and adult fertile females (recipients) (B6D2f1, 2-4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46-47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, *Biol. Reprod.* 77:159 (1986), and Dienhart and Downs, *Zygote* 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a Zcytor14 encoding sequence is linearized, gel-purified, and resuspended in 10 mM Tris-HCl (pH 7.4), 0.25 mM EDTA (pH 8.0), at a final concentration of 5-10 nanograms per microliter for microinjection. For example, the Zcytor14 encoding sequences can encode a polypeptide comprising amino acid residues 21 to 452 of SEQ ID NO:2.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12-17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a Zcytor14 gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5-2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7-10 days after surgery. The expression level of Zcytor14 mRNA is examined for each transgenic mouse using an RNA solution hybridization assay or polymerase chain reaction.

In addition to producing transgenic mice that over-express IL-17F, IL-17A or Zcytor14, it is useful to engineer transgenic mice with either abnormally low or no expression of any of these genes. Such transgenic mice provide useful models for diseases associated with a lack of IL-17F, IL-17A or Zcytor14. As discussed above, Zcytor14 gene expression can be inhibited using anti-sense genes, ribozyme genes, or external guide sequence genes. To produce transgenic mice that under-express the Zcytor14 gene, such inhibitory sequences are targeted to Zcytor14 mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in *Methods in Gene Biotechnology*, pages 205-224 (CRC Press 1997)).

An alternative approach to producing transgenic mice that have little or no Zcytor14 gene expression is to generate mice having at least one normal Zcytor14 allele replaced by a nonfunctional Zcytor14 gene. One method of designing a nonfunctional Zcytor14 gene is to insert another gene, such as a selectable marker gene, within a nucleic acid molecule that encodes Zcytor14. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), and Wu et al., "New Strategies for Gene Knockout," in *Methods in Gene Biotechnology*, pages 339-365 (CRC Press 1997)).

The invention is further illustrated by the following non-limiting examples.

EXAMPLES

Example 1

Expression of the ZcytoR14 Gene

Northern analyses were performed using Human Multiple Tissue Blots (CLONTECH Laboratories, Inc., Palo Alto, Calif.). Two probes were generated from gel purified PCR products. The first probe was made using ZC21798 (5' CGG CGT GGT GGT CTT GCT CTT 3; SEQ ID NO:8) and ZC21808 (5' TCC CGT CCC CCG CCC CAG GTC 3; SEQ ID NO:31) as primers. The probe was a radioactively labeled using the Multiprime labeling kit from Amersham (Arlington Heights, Ill.) according to the manufacturer's protocol. The probe was purified using a NUCTRAP push column (STRATAGENE, La Jolla, Calif.). EXPRESSHYB (CLONTECH) solution was used for the prehybridization and hybridization solutions for the northern blots. Hybridization took place overnight at 65 C. Following hybridization, the blots were washed for 30 minutes each in solutions that contained 0.1% SDS and SSC as follows: twice in 2×SSC at room temperature, three times in 0.1×SSC at 50° C., once in 0.1×SSC at 55° C., and once in 0.1×SSC at 65° C. The results demonstrated the ZcytoR14 gene is strongly expressed in thyroid, adrenal gland, prostate, and liver tissues, and expressed to a lesser extent in heart, small intestine, stomach, and trachea tissues. In contrast, there is little or no expression in brain, placenta, lung, skeletal muscle, kidney, pancreas, spleen, thymus, testis, ovary, colon, peripheral blood leukocytes, spinal cord, lymph node, and bone marrow.

Example 2

Distribution of mRNA in Cell Line Panels Using PCR

Total RNA was purified from resting and stimulated cell lines grown in-house and purified using a Qiagen (Valencia, Calif.) RNeasy kit according to the manufacturer's instructions, or an acid-phenol purification protocol (Chomczynski and Sacchi, Analytical Biochemistry, 162:156-9, 1987). The quality of the RNA was assessed by running an aliquot on an Agilent Bioanalyzer. If the RNA was significantly degraded, it was not used for subsequent creation of first strand cDNA. Presence of contaminating genomic DNA was assessed by a PCR assay on an aliquot of the RNA with zc41011 (5'CTCTCCATCCTTATCTTTCATCAAC 3'; SEQ ID NO:32) and zc41012 (5'CTCTCTGCTGGCTAAACAAAACAC 3'; SEQ ID NO:33), primers that amplify a single site of intergenic genomic DNA. The PCR conditions for the contaminating genomic DNA assay were as follows: 2.5 µl 10× buffer and 0.5 µl Advantage 2 cDNA polymerase mix (BD Biosciences Clontech, Palo Alto, Calif.), 2 ul 2.5 mM dNTP mix (Applied Biosystems, Foster City, Calif.), 2.5 µl 10× Rediload (Invitrogen, Carlsbad, Calif.), and 0.5 µl 20 uM zc41011 and zc41012, in a final volume of 25 ul. Cycling parameters were 94° C. 20", 40 cycles of 94° C. 20" 60° C. 1'20" and one cycle of 72° C. 7'. 10 ul of each reaction was subjected to agarose gel electrophoresis and gels were examined for presence of a PCR product from contaminating genomic DNA. If contaminating genomic DNA was observed, the total RNA was DNAsed using DNA-free reagents (Ambion, Inc, Austin, Tex.) according to the manufacturer's instructions, then retested as described above. Only RNAs which appeared to be free of contaminating genomic DNA were used for subsequent creation of first strand cDNA.

20 µg total RNA from 82 human cell lines were each brought to 98 µl with $H_2O$, then split into two 49 ul aliquots, each containing 10 µg total RNA, and placed in two 96-well PCR plates. To each aliquot was added reagents for first strand cDNA synthesis (Invitrogen First Strand cDNA Synthesis System, Carlsbad, Calif.): 20 µl 25 mM $MgCl_2$, 10 ul 10×RT buffer, 10 ul 0.1 M DTT, 2 µl oligo dT, 2 ul RNAseOut. Then, to one aliquot from each cell line 2 µl Superscript II Reverse Transcriptase was added, and to the corresponding cell line aliquot 2 µl $H_2O$ was added to make a minus Reverse Transcriptase negative control. All samples were incubated as follows: 25° C. 10', 42° C. 50', 70° C. 15'. Samples were arranged in deep well plates and diluted to 1.7 ml with $H_2O$. A Multipette (Saigan) robot was used to aliquot 16.5 µl into each well of a 96-well PCR plate multiple times, generating numerous one-use PCR panels of the cell lines, which were then sealed and stored at −20° C. Each well in these panels represents first strand cDNA from approximately 100 ng total RNA. The 82 cell lines are spread across two panels, array #118A and #118B. Quality of first strand cDNA on the panels was assessed by a multiplex PCR assay on one set of the panels using primers to two widely expressed, but only moderately abundant genes, CLTC (clathrin) and TFRC (transferrin receptor C). 0.5 ul each of Clathrin primers zc42901 (5'CTCATATTGCTCAACTGTGTGAAAAG 3'; SEQ ID NO:34), zc42902 (5'TAGAAGCCACCTGAACACAAATCTG3'; SEQ ID NO:35), and TFRC primers zc42599 (5'ATCTTGCGTTGTATGTTGAAAATCAATT3'; SEQ ID NO:36), zc42600 (5'TTCTCCACCAGGTAAACAAGTCTAC3'; SEQ ID NO:37), were mixed with 2.5 µl 10× buffer and 0.5 µl Advantage 2 cDNA polymerase mix (BD Biosciences Clontech, Palo Alto, Calif.), 2 µl 2.5 mM dNTP mix (Applied Biosystems, Foster City, Calif.), 2.5 µl 10× Rediload (Invitrogen, Carlsbad, Calif.), and added to each well of a panel of array#118A and array #118B. Cycling parameters were as follows: 94° C. 20", 35 cycles of 94° C. 20", 67° C. 80", and one cycle of 72° C. 7'. 10 µl of each reaction was subjected to agarose gel electrophoresis and gels were scored for the presence of a robust PCR product for each gene specific to the +RT wells for each cell line.

Expression of mRNA in the human first strand cDNA panels for ZcytoR14 was assayed by PCR with sense oligo ZC42756 (5' ctctccaggcccaagtcgtgctct3'; SEQ ID NO:38) and antisense oligo ZC42757 (5' ttgtcctgggggcctcgtgtctcc3'; SEQ ID NO:39) under these PCR conditions per sample: 2.5 µl 10× buffer and 0.5 µl advantage 2 cDNA polymerase mix (BD Biosciences Clontech, Palo Alto, Calif.), 2 µl 2.5 mM dNTP mix (Applied Biosystems), 2.5 ul 10× Rediload (Invitrogen, Carlsbad, Calif.), and 0.5 µl 20 uM each sense and antisense primer. Cycling conditions were 94° C. 2', 35 cycles of 94° C. 1', 66° C. 30", 72° C. 1.5°, and one cycle of 72° C. 7'. 10 µl of each reaction was subjected to agarose gel electrophoresis and gels were scored for positive or negative expression of ZcytoR14.

ZcytoR14 mRNA is widely expressed in many cell lines representing a broad spectrum of tissue and cell types. In particular, ZcytoR14 is consistently expressed in non-T cell peripheral blood cell lines, including monocytes, B-cells, and cells of the myeloid lineage. Also, ZcytoR14 mRNA is reliably expressed in cell lines derived from skin. Other cell lines that express ZcytoR14 are all 5 of the large intestine cell lines that were present on the array.

Example 3

Distribution of mRNA in Mouse Cell Line Panels Using RT PCR

Total RNA was purified from 60 resting and stimulated cell lines grown in-house and purified using a Qiagen (Valencia, Calif.) RNeasy kit according to the manufacturer's instructions, an acid-phenol purification protocol (Chomczynski and Sacchi, Analytical Biochemistry, 162:156-9, 1987), or a Trizol reagent protocol (Invitrogen, Carlsbad, Calif.).

5 µg of total RNA from each cell line was arranged in a deep well 96-well plate, 125 µl 3M NaOAc and 100 µl Pellet Paint (Novagen, Madison, Wis.)) were added to each well, then the final volume was adjusted to 1.25 ml with $H_2O$. A Multipette (Saigan) robot was used to aliquot 25 µl of the RNA mixture followed by 75 ul EtOH into each well of a 96-well PCR plate multiple times, generating numerous one-use RT PCR panels of the cell lines, which were then sealed and stored at −20° C. RT PCR screening was performed by first centrifuging a panel in a Qiagen (Valencia, Calif.) 96-well centrifuge for 10' at 6000 RPM. Supernatant was removed by inverting the plate onto absorbent paper. RNA pellets were washed with 100 µl 70% EtOH, followed by a 5' centrifugation at 6000 RPM. Supernatant was again removed and plates allowed to air-dry until the remaining EtOH was evaporated. RNA pellets were resuspended in 15 µl $H_2O$.

Expression of ZcytoR14 mRNA in the mouse cell line RNA panels was assayed by RT PCR with zc38910 (5' acgaagcccaggtaccagaaagag3'; SEQ ID NO:40) and zc38679 (5' aaaagcgccgcagccaagagtagg3'; SEQ ID NO:41) under these RT PCR conditions per sample: SuperScript One-Step PCR with Platinum Taq kit, Invitrogen, Carlsbad, Calif. Cycling conditions were: 1 cycle of 48° C. for 30 minutes, 94° C. for 2 minutes, followed by 35 cycles of 94° C. for 15 seconds, 55° C. for 30 seconds, 72° C. for 1.5 minutes, followed by 1 cycle of 72° C. for 7 minutes. 10 µl of each reaction was subjected to agarose gel electrophoresis and gels were scored for positive or negative expression of ZcytoR14.

Murine ZcytoR14mRNA is expressed in several mouse cell lines, notably in cell lines derived from bone marrow, including osteoblast, adipocyte, and preadipocyte cell lines. Also, mouse ZcytoR14 is mRNA is represented in several samples from the endocrine system, such as pancreas stromal cell lines, pancreas islet cell lines, and hypothalamus, salivary gland, and testis cell lines.

Example 4

Refolding and Purification pIL-17F Produced in *E. coli*

A) Inclusion Body Isolation and Extraction of pIL-17F

Following induction of protein expression in either batch ferment or shaker flask culture, the *E. coli* broth is centrifuged in 1 liter bottles @ 3000 RPM in a Sorvall swinging bucket rotor. Washing of the cell paste to remove any broth contaminants is performed with 50 mM Tris pH 8.0 containing 200 mM NaCl and 5 mM EDTA until the supernate is clear.

The cell pellets are then suspended in ice-cold lysis buffer (50 mM Tris pH 8.0; 5 mM EDTA; 200 mM NaCl, 10% sucrose (w/v); 5 mM DTT; 5 mM Benzamidine) to 10-20 Optical Density units at 600 nm. This slurry is then subjected to 3 passes at 8500-9000 psi in a chilled APV 2000 Lab Homogenizer producing a disrupted cell lysate. The insoluble fraction (inclusion bodies) is recovered by centrifugation of the cell lysate at 20,000×G for 1 hour at 4° C.

The inclusion body pellet resulting from the 20,000×G spin is weighed and then re-suspended in wash buffer (50 mM Tris pH 8 containing 200 mM NaCl, 5 mM EDTA, 5 mM DTT, 5 mM Benzamidine) at 10 ml wash buffer per gram inclusion bodies. Complete dispersion is achieved by homogenizing with an OMNI international rotor stator generator. This suspension is centrifuged at 20,000×G for 30 minutes at 4° C. The wash cycle is repeated 3-5 times until the supernatant is clear.

The final washed pellet is solubilized in 7M Guanidine HCl in 40 mM Tris buffer at pH 8 containing 0.1M Sodium Sulfite and 0.02 M Sodium Tetrathionate. The extraction and sulfitolysis reaction is allowed to proceed with gentle stirring at 4° C. overnight. The resulting pinkish colored solution is centrifuged at 35,000×g for 1 hour at 4° C. and the clarified supernate, containing the soluble pIL-17F, is 0.45 um filtered.

B) pIL-17F Refolding Procedure

The solubilized, sulfitolyzed pIL-17F is refolded by drop wise dilution into ice cold refolding buffer containing 55 mM MES, 10.56 mM NaCl, 0.44 mM KCl, 0.055% PEG (3400 K), 1.1 mM EDTA, 20% Glycerol, 0.5M Guanidine HCl, 0.75 M Arginine and the Glutathione redox pair at a 1:1 ratio (1 mM GSH:1 mM GSSG). The pH of the refolding buffer is adjusted to 6.5 with HCl and the pIL-17F is added to a final concentration of 100 ug/ml. Once diluted, the mixture is allowed to stir slowly in the cold room for 72 hours.

C) Product Recovery & Purification

The refolded pIL-17F is concentrated 10× vs. a 10 kDa cutoff membrane on a lab scale TFF system. Next it is filtered using a 0.45 micron membrane and the pH is adjusted to 5.1 with the addition of Acetic acid. The pH-adjusted material is captured by cation exchange chromatography on a Pharmacia SP Fast Flow column equilibrated in 50 mM Acetate buffer, pH 5.1. The pIL-17F is loaded by inline proportioning at 1:5 with equilibration buffer at a flow rate of 190 cm/hr. This dilution lowers the ionic strength enabling efficient binding of the target to the matrix. After sample loading is complete, the column is washed to baseline absorbance with equilibration buffer. The column is washed with 0.4 M NaCl in 50 mM Acetate buffer at pH 5.1 and then the bound protein is eluted with a 5 CV gradient from 0.4 M to 1.5 M NaCl in 50 mM Acetate buffer at pH 5.1. The protein elutes at ~1M NaCl and is approximately 85% dimeric by SDS PAGE analysis of eluate fractions. The fractions containing pIL-17F are pooled and concentrated against a 10 kDa cutoff ultrafiltration membrane using an Amicon stirred cell in preparation for the final purification and buffer exchange by size exclusion chromatography.

D) Size Exclusion Buffer Exchange and Formulation

The concentrated cation pool (at a volume of 3-4% of CV) is injected at a flow rate of 30 cm/hr onto a Pharmacia Superdex 75 size exclusion column equilibrated in 50 mM Sodium Phosphate buffer containing 109 mM NaCl, pH 7.2. The symmetric eluate peak containing the product is diluted to a concentration of 1 mg/ml in 50 mM Sodium Phosphate buffer containing 109 mM NaCl, pH 7.2. Finally the pIL-17F is 0.2 micron sterile filtered, aliquoted and stored at −80° C. The final process yield is 20%.

Example 5

Construction of Mammalian Soluble ZcytoR14 Expression Construct

An expression construct containing human ZcytoR14 [L21-K451]-mFc1 (mouse BALB/c µ2a Fc) is constructed via overlap PCR and homologous recombination using a DNA fragment (SEQ ID NO:42) encoding a ZcytoR14 polypeptide (SEQ ID NO:43), a DNA fragment encoding mFc1 (SEQ ID NO:44), and the expression vector pZMP20. The fragments are generated by PCR amplification.

The PCR fragment encoding ZcytoR14 [L21-K451] contains a 5' overlap with the pZMP20 vector sequence in the optimized tissue plasminogen activator pre-pro secretion leader sequence coding region, the ZcytoR14 extracellular domain coding [L21-K451], and a 3' overlap with the mFc1 coding region. The PCR amplification reaction uses the 5' oligonucleotide [GTTTCGCTCAGCCAGGAAATCCATGCCGAGTTGAGACGCTTCCGTAGACTGGAGAGGCTTGTGGGGCCT; SEQ ID NO:46], the 3' oligonucleotide [TGTGGGCCCTCTGGGCTCCTTGTGGATGTATTTGTC; SEQ ID NO:47], and a previously generated DNA clone of ZcytoR14 as the template.

The PCR fragment encoding mFc1 contains a 5' overlap with the ZcytoR14 sequence, the mFc1 coding region, and a 3' overlap with the pZMP20 vector in the poliovirus internal ribosome entry site region. The PCR amplification reaction uses the 5 oligonucleotide [GACAAATACATCCACAAGGAGCCCAGAGGGCCCACA; SEQ ID NO:48], the 3' oligonucleotide [CAACCCCAGAGCTGTTTTAAGGCGCGCCTCTAGATTATTTACCCGGAGTCCGGGA; SEQ ID NO:49], and a previously generated DNA clone of mFc1 as the template.

The PCR amplification reaction conditions are as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixtures are run on a 1% agarose gel and the DNA fragments corresponding to the expected sizes are extracted from the gel using a QIAquick™ Gel Extraction Kit (Qiagen, Cat. No. 28704).

The two PCR fragments are joined by overlap PCR. Approximately 1 µl each of the two gel extracted fragments are combined in a PCR amplification reaction using the 5' oligonucleotide [GTTTCGCTCAGCCAGGAAATCCATGCCGAGTTGAGACGCTTCCGTAGACTGGAGAGGCTTGTGGGGCCT; SEQ ID NO: 46] and the 3' oligonucleotide [CAACCCCAGAGCTGTTTTAAGGCGCGCCTCTAGATTATTTACCCGGAGTCCGGGA; SEQ ID NO:49]. PCR conditions used are as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixture is run on a 1% agarose gel and the DNA fragment corresponding to the size of the insert is extracted from the gel using a QIAquick™ Gel Extraction Kit (Qiagen, Cat. No. 28704).

Plasmid pZMP20 is a mammalian expression vector containing an expression cassette having the MPSV promoter, a BglII site for linearization prior to yeast recombination, an otPA signal peptide sequence, an internal ribosome entry element from poliovirus, the extracellular domain of CD8 truncated at the C-terminal end of the transmembrane domain; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae.

The plasmid pZMP20 is digested with BglII prior to recombination in yeast with the gel extracted ZcytoR14[L21-K451]-mFc1 PCR fragment. 100 ul of competent yeast (S. cerevisiae) cells are combined with 10 µl of the ZcytoR14 [L21-K451]-mFc1 insert DNA and 100 ng of BglII digested pZMP20 vector, and the mix is transferred to a 0.2 cm electroporation cuvette. The yeast/DNA mixture is electropulsed using power supply (BioRad Laboratories, Hercules, Calif.) settings of 0.75 kV (5 kV/cm), ∞ ohms, and 25 µF. Six hundred µl of 1.2 M sorbitol is added to the cuvette, and the yeast is plated in 100 µl and 300 µl aliquots onto two URA-D plates and incubated at 30° C. After about 72 hours, the Ura+ yeast transformants from a single plate are resuspended in 1 ml H$_2$O and spun briefly to pellet the yeast cells. The cell pellet is resuspended in 0.5 ml of lysis buffer (2% Triton X-100, 1% SDS, 100 mM NaCl, 10 mM Tris, pH 8.0, 1 mM EDTA). The five hundred µl of the lysis mixture is added to an Eppendorf tube containing 250 µl acid-washed glass beads and 300 µl phenol-chloroform, is vortexed for 3 minutes, and spun for 5 minutes in an Eppendorf centrifuge at maximum speed. Three hundred µl of the aqueous phase is transferred to a fresh tube, and the DNA is precipitated with 600 µl ethanol, followed by centrifugation for 30 minutes at maximum speed. The tube is decanted and the pellet is washed with 1 mL of 70% ethanol. The tube is decanted and the DNA pellet is resuspended in 30 µl 10 mM Tris, pH 8.0, 1 mM EDTA.

Transformation of electrocompetent E. coli host cells (DH12S) is done using 5 µl of the yeast DNA preparation and 50 µl of E. coli cells. The cells are electropulsed at 2.0 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) is added and then the cells are plated in 50 µL1 and 200 µl aliquots on two LB AMP plates (LB broth (Lennox), 1.8% Bacto™ Agar (Difco), 100 mg/L Ampicillin).

The inserts of three DNA clones for the construct is subjected to sequence analysis and one clone containing the correct sequence is selected. Large scale plasmid DNA is isolated using a commercially available kit (QIAGEN Plasmid Mega Kit, Qiagen, Valencia, Calif.) according to manufacturer's instructions.

Example 6

Construction of Mammalian Soluble ZcytoR14 Expression Constructs that Express ZcytoR14-CEE, ZcytoR14-CHIS, and ZcytoR14-CFLAG An expression construct containing human ZcytoR14 [L21-K451] with a C-terminal tag, either Glu-Glu (CEE), six His (CHIS), or FLAG (CFLAG), is constructed via PCR and homologous recombination using a DNA fragment encoding ZcytoR14 [L21-K451] (SEQ ID NO:42) and the expression vector pZMP20.

The PCR fragment encoding ZcytoR14CEE contains a 5' overlap with the pZMP20 vector sequence in the optimized tissue plasminogen activator pre-pro secretion leader sequence coding region, the ZcytoR14 extracellular domain coding [L21-K451], the sequence of the Glu-Glu tag (Glu Glu Tyr Met Pro Met Glu; SEQ ID NO:53), and a 3' overlap with the pZMP20 vector in the poliovirus internal ribosome entry site region. The PCR amplification reaction uses the 5' oligonucleotide [GTTTCGCTCAGCCAGGAAATCCATGCCGAGTTGAGACGCTTCCGTAGACTGGAGA GGCTTGTGGGGCCT; SEQ ID NO:46], the 3' oligonucleotide [CAACCCCAGAGCTGTTTTAAGGCGCGCCTCTAGATTATTCCATGGGCATGTATTCT TCCTTGTGGATGTATTTGTC; SEQ ID NO:50], and a previously generated DNA clone of ZcytoR14 as the template.

The PCR amplification reaction condition is as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixture is run on a 1% agarose gel and the DNA fragment corresponding to the expected size is extracted from the gel using a QIAquick™ Gel Extraction Kit (Qiagen, Cat. No. 28704).

The plasmid pZMP20 is digested with BglII prior to recombination in yeast with the gel extracted ZcytoR14CEE PCR fragment. One hundred µl of competent yeast (*S. cerevisiae*) cells are combined with 10 µl of the ZcytoR14CEE insert DNA and 100 ng of BglII digested pZMP20 vector, and the mix is transferred to a 0.2 cm electroporation cuvette. The yeast/DNA mixture is electropulsed using power supply (BioRad Laboratories, Hercules, Calif.) settings of 0.75 kV (5 kV/cm), ∞ ohms, and 25 µF. Six hundred µl of 1.2 M sorbitol is added to the cuvette, and the yeast is plated in 100 µl and 300 µl aliquots onto two URA-D plates and incubated at 30° C. After about 72 hours, the Ura$^+$ yeast transformants from a single plate are resuspended in 1 ml $H_2O$ and spun briefly to pellet the yeast cells. The cell pellet is resuspended in 0.5 ml of lysis buffer (2% Triton X-100, 1% SDS, 100 mM NaCl, 10 mM Tris, pH 8.0, 1 mM EDTA). The five hundred µl of the lysis mixture is added to an Eppendorf tube containing 250 µl acid-washed glass beads and 300 µl phenol-chloroform, is vortexed for 3 minutes, and spun for 5 minutes in an Eppendorf centrifuge at maximum speed. Three hundred µl of the aqueous phase is transferred to a fresh tube, and the DNA is precipitated with 600 µl ethanol, followed by centrifugation for 30 minutes at maximum speed. The tube is decanted and the pellet is washed with 1 mL of 70% ethanol. The tube is decanted and the DNA pellet is resuspended in 30 µl 10 mM Tris, pH 8.0, 1 mM EDTA.

Transformation of electrocompetent *E. coli* host cells (DH12S) is done using 5 µl of the yeast DNA preparation and 50 µl of *E. coli* cells. The cells are electropulsed at 2.0 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is added and then the cells are plated in 50 µL1 and 200 µl aliquots on two LB AMP plates (LB broth (Lennox), 1.8% Bacto™ Agar (Difco), 100 mg/L Ampicillin).

The inserts of three DNA clones for the construct is subjected to sequence analysis and one clone containing the correct sequence is selected. Large scale plasmid DNA is isolated using a commercially available kit (QIAGEN Plasmid Mega Kit, Qiagen, Valencia, Calif.) according to manufacturer's instructions.

The same process is used to prepare the ZcytoR14 with a C-terminal his tag, composed of Gly Ser Gly Gly His His His His His His (ZcytoR14-CHIS; SEQ ID NO:51) or the C-terminal FLAG tag, composed of Gly Ser Asp Tyr Lys Asp Asp Asp Asp Lys (ZcytoR14CFLAG; SEQ ID NO:52). To prepare these constructs, instead of the 3' oligonucleotide of SEQ ID NO:50; the 3' oligonucleotide [CAACCCCAGAGCTGTTT-TAAGGCGCGCCTCTAGATTAGTGATGGT-GATGGTGATGT CCACCAGATCCCTTGTGGATG-TATTTGTC; SEQ ID NO:54] is used to generate ZcytoR14CHIS or the 3' oligonucleotide [CAACCCCA-GAGCTGTTTTAAGGCGCGCCTCTAGAT-TACTTATCATCATCATCCTTA TAATCGGATCCCT-TGTGGATGTATTTGTC; SEQ ID NO:55] is used to generate ZcytoR14CFLAG.

Example 7

Transfection and Expression of Soluble ZcytoR14 Receptor Expression Constructs that Express the ZcytoR14-mFc1 Fusion Protein, and the ZcytoR14-CEE, ZcytoR14-CHIS, and ZcytoR14-CFLAG C-Terminal Tagged Proteins Three sets of 200 µg of each of the soluble ZcytoR14 fusion or tagged expression constructs are separately digested with 200 units of PvuI at 37° C. for three hours, precipitated with isopropyl alcohol, and centrifuged in a 1.5 mL microfuge tube. The supernatant is decanted off the pellet, and the pellet is washed with 1 mL of 70% ethanol and allowed to incubate for 5 minutes at room temperature. The tube is spun in a microfuge for 10 minutes at 14,000 RPM and the supernatant is decanted off the pellet. The pellet is then resuspended in 750 µl of CHO cell tissue culture medium in a sterile environment, allowed to incubate at 60° C. for 30 minutes, and is allowed to cool to room temperature. Approximately $5 \times 10^6$ CHO cells are pelleted in each of three tubes and are resuspended using the DNA-medium solution. The DNA/cell mixtures are placed in a 0.4 cm gap cuvette and electroporated using the following parameters; 950 µF, high capacitance, at 300 V. The contents of the cuvettes are then removed, pooled, and diluted to 25 mLs with CHO cell tissue culture medium and placed in a 125 mL shake flask. The flask is placed in an incubator on a shaker at 37° C., 6% $CO_2$ with shaking at 120 RPM.

The CHO cells are subjected to nutrient selection followed by step amplification to 200 nM methotrexate (MTX), and then to 1 µM MTX. Fusion or tagged protein expression is confirmed by Western blot, and the CHO cell pool is scaled-up for harvests for protein purification.

Example 8

Expression of Soluble ZcytoR14

An expression plasmid containing ZcytoR14-Tbx-C(Fc9) (SEQ ID NO:64) was constructed via homologous recombination using a DNA fragment of ZcytoR14_Tbx and the expression vector pZMP40. The fragment was generated by PCR amplification using primers zc44531 and zc44545.

The PCR fragment ZcytoR14_Tbx contains a partial ZcytoR14 extracellular domain coding region, which was made using a previously generated clone of ZcytoR14 as the template. The fragment includes a 5' overlap with the pZMP40 vector sequence in the otPA coding region, the ZcytoR14 segment (amino acid residue 21 to 451 of SEQ ID NO:2), a linker sequence, a thrombin cleavage site, and a 3' overlap with the pZMP40 vector in the Fc9 coding region. PCR conditions used were as follows: 1 cycle, 94° C., 5 minutes; 35 cycles, 94° C., 1 minute, followed by 55° C., 2 minutes, followed by 72° C., 3 minutes; 1 cycle, 72° C., 10 minutes.

The PCR reaction mixtures were run on a 1% agarose gel and a band corresponding to the sizes of the inserts were gel-extracted using a QIAquick™ Gel Extraction Kit (Qiagen, Cat. No. 28704).

Plasmid pZMP40 is a mammalian expression vector containing an expression cassette having the MPSV promoter, multiple restriction sites for insertion of coding sequences, an otPA signal peptide sequence, and the sequence for Fc9; an internal ribosome entry site (IRES) element from poliovirus, and the extracellular domain of CD8 truncated at the C-terminal end of the transmembrane domain; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It was constructed from pZMP21 (Patent Pub. No. US 2003/0232414 A1; deposited at the American Type Culture Collection and designated as ATCC#PTA-5266).

The plasmid pZMP40 was cut with BglII prior to recombination in yeast with the PCR fragment. One hundred microliters of competent yeast (*S. cerevisiae*) cells were independently combined with 10 µl of the insert DNA (SEQ ID NO:66) and 100 ng of cut pZMP40 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 µF. Six hundred µl of 1.2 M sorbitol was added to the cuvette, and the yeast was plated in a 100-µl and 300 µl aliquot onto two URA-D plates and incubated at 30° C. After about 72 hours, the Ura+ yeast transformants from a single plate were resuspended in 1 ml $H_2O$ and spun briefly to pellet the yeast cells. The cell pellet was resuspended in 0.5 ml of lysis buffer (2% Triton X-100, 1% SDS, 100 mM NaCl, 10 mM Tris, pH 8.0, 1 mM EDTA). The five hundred microliters of the lysis mixture was added to an Eppendorf tube containing 250 µl acid-washed glass beads and 300 µl phenol-chloroform, was vortexed for 3 minutes, and spun for 5 minutes in an Eppendorf centrifuge at maximum speed. Three hundred microliters of the aqueous phase was transferred to a fresh tube, and the DNA was precipitated with 600 µl ethanol (EtOH), followed by centrifugation for 30 minutes at maximum speed. The tube was decanted and the pellet was washed with 1 mL of 70% ethanol. The tube was decanted and the DNA pellet was resuspended in 30 µl TE.

Transformation of electrocompetent *E. coli* host cells (DH12S) was done using 5 µl of the yeast DNA prep and 50 µl of cells. The cells were electropulsed at 2.0 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 µl and a 200 µl aliquot on two LB AMP plates (LB broth (Lennox), 1.8% Bacto™ Agar (Difco), 100 mg/L Ampicillin).

The inserts of three clones for the construct was subjected to sequence analysis and one clone for each construct, containing the correct sequence, was selected. Larger scale plasmid DNA was isolated using a commercially available kit (QIAGEN Plasmid Mega Kit, Qiagen, Valencia, Calif.) according to manufacturer's instructions.

Three sets of 200 µg of the ZcytoR14[L21-K451]_Tbx_C (Fc9) construct were then each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 µl of PF-CHO media in a sterile environment, allowed to incubate at 60° C. for 30 minutes, and was allowed to cool to room temperature. 5E6 APFDXB11 cells were spun down in each of three tubes and were resuspended using the DNA-media solution. The DNA/cell mixtures were placed in a 0.4 cm gap cuvette and electroporated using the following parameters: 950 µF, high capacitance, and 300 V. The contents of the cuvettes were then removed, pooled, and diluted to 25 mLs with PF-CHO media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX), and then to 1 µM MTX. Expression was confirmed by western blot, and the cell line was scaled-up and protein purification followed.

Example 9

Purification of Soluble ZcytoR14 from CHO Cells

Conditioned media from CHO cells expressing ZcytoR14-TbX-Fc9 (SEQ ID NO:64) was concentrated approximately 10-fold with a Pellicon-II tangential flow system against two Biomax 0.1 $m^2$ 30 kD molecular weight cutoff membrane cassettes (Millipore, Bedford, Mass.). The concentrated media was pH adjusted to 5.5 with glacial acetic acid, 0.2 m sterile filtered then loaded onto a Protein G sepharose fast flow resin (Pharmacia, Piscataway, N.J.) via batch chromatography overnight at 4 C. Prior to loading the pH adjusted conditioned media, the Protein G resin was pre-equilibrated with, 5 column volumes (approximately 150 ml) of 25 mM sodium acetate, 150 mM NaCl, pH5.5. The ratio of filtered, pH adjusted conditioned media to resin was 33:1 (v/v).

The batched chromatography process was performed at ambient room temperature (approximately 21 C). The batched, pH adjusted, 0.22 µm filtered, conditioned media was poured into an empty 5.5×20.5 cm glass column (Bio-Rad, Hercules, Calif.) and packed via gravity. The column was washed with 10 column volumes (approximately 300 ml) of 25 mM sodium acetate, 150 mM NaCl, pH5.5. Bound protein was then pH eluted with 100 mM glycine, pH 2.7. 9.0 ml fractions were collected and immediately neutralized with 1.0 ml 2.0M Tris, pH 8.0. The collected fractions were analyzed via SDS-PAGE Coomassie staining Fractions containing ZcytoR14-Tbx-Fc9 were pooled and concentrated approximately 6-fold using a 5 kD molecular weight cutoff Biomax membrane spin concentrator (Millipore, Bedford, Mass.) according to the manufacturer's instructions.

The pooled, concentrated fractions were then dialyzed, at 4 C, extensively against 1× phosphate buffered saline, pH 7.3 (Sigma, St. Louis, Mo.) using a 7 kD molecular weight cutoff membrane Slide-A-Lyzer (Pierce, Rockford, Ill.). ZcytoR14-TbX-Fc9 as formulated in 1× phosphate buffered saline, pH 7.3 was 0.22 µm sterile filtered prior to aliquoting and storage at −80 C.

Example 10

Binding of IL-17A and IL-17F to Human ZcytoR14

A) Binding of Biotinylated Cytokines to Transfected Cells

Baby Hamster Kidney (BHK) cells that had been transfected with expression vectors encoding human IL-17 receptor (SEQ ID NO:21), human ZcytoR14 (SEQ ID NO:2), or both of these receptors are assessed for their ability to bind biotinylated human IL-17A and human IL-17F. Cells are harvested with versene, counted and diluted to $10^7$ cells per ml in staining media (SM), which is HBSS plus 1 mg/ml bovine serum albumin (BSA), 10 mM Hepes, and 0.1% sodium azide (w/v). Biotinylated human IL-17A (SEQ ID NO:14) and human IL-17F (SEQ ID NO:16) are incubated with the cells on ice for 30 minutes at various concentrations. After 30 minutes, excess cytokine is washed away with SM and the cells are incubated with a 1:100 dilution of streptavidin conjugated to phycoerythrin (SA-PE) for 30 minutes on ice. Excess SA-PE is washed away and cells are analyzed by flow cytometry. The amount of cytokine binding was quantitated from the mean fluorescence intensity of the cytokine staining. From this analysis, we find that human IL-17A binds both the human IL-17R and ZcytoR14 to a similar extent. Also, human IL-17F binds ZcytoR14 to a similar level, but binds IL-17R detectably, but to a much lower level than was seen with IL-17A.

B) Binding of Biotinylated Cytokines to Human Peripheral Blood Mononuclear Cells Human peripheral blood mononuclear cells (PBMC) were prepared from whole blood by ficoll density gradient centrifugation. PBMC at $10^7$ cells per ml were simultaneously incubated with biotinylated IL-17A or IL-17F at 1 μg/ml and fluorochrome conjugated antibodies to specific cell surface proteins that were designed to distinguish various white blood cell lineages. These markers include CD4, CD8, CD19, CD11b, CD56 and CD16. Excess antibody and cytokine are washed away, and specific cytokine binding is detected by incubating with SA-PE as described above. Samples were analyzed by flow cytometry and from this analysis, we find that human IL-17A binds to virtually all PBMC populations examined, but that human IL-17F does not detectably bind to any population.

C) Inhibition of Specific Binding of Biotinlyated Human IL-17A and IL-17F with Unlabeled Cytokine Binding studies are performed as discussed above, but excess unlabeled human IL-17A and IL-17F are included in the binding reaction. In studies with BHK cells, the amount of unlabeled cytokine was varied over a range of concentrations and we find that addition of unlabeled IL-17A competed for binding of both IL-17A and IL-17F to both ZcytoR14 and IL-17R. However, unlabeled IL-17F competed for binding of both IL-17A and IL-17F to ZcytoR14, but it did not compete effectively for binding to IL-17R. This indicates that both IL-17A and IL-17F specifically bind to ZcytoR14, and that they bind at a site that is either identical or overlaps significantly since they cross-compete for binding. Also, IL-17A competes for the relatively weak binding of IL-17F for IL-17R, indicating these two cytokines also bind to a similar region in the IL-17R, but IL-17F binds IL-17R with much reduced affinity relative to ZcytoR14.

D) Inhibition of Specific Binding of Biotinylated Human IL-17A and IL-17F with Soluble ZcytoR14 and IL-17R Binding studies are performed as discussed above, except that a soluble form of ZcytoR14 or IL-17R are included in the binding reactions. These soluble receptors are fusion proteins derived from the extracellular domain of each receptor fused to the human IgG1 constant (Fc) region. We find that soluble ZcytoR14 inhibits binding of both human IL-17A and IL-17F to both IL-17R and ZcytoR14 transfected BHK cells. However, soluble IL-17R inhibits binding of IL-17A to either receptor, but does not effectively block binding of IL-17F to ZcytoR14, consistent with the poor binding of IL-17F for the IL-17R.

Example 11

IL-17A and IL-17F Bind to ZcytoR14

A) Binding Inhibition with Cold Ligand

BHK cells transfected with hZcytoR14 (SEQ ID NO:2) and IL-17R (SEQ ID NO:21) were plated at 40,000 cells/well in a 24-well dish (Costar 3527) two days prior to assay. IL-17A (SEQ ID NO:14) and IL-17F (SEQ ID NO:16) that had been radiolabeled by the iodobead method were added independently to wells in triplicate at 10 ng/ml with a total of 250 ul/well in binding buffer (RPMI 1640 media (JRH 51502-500M) with 10 mg/ml bovine serum albumin (Gibco15260-037)). Cold competitors were added in 100 fold molar excess. Competitors tested included IL-17A, IL-17B, IL-17C, IL-17D, IL-17E, IL-17F and IL-21. Wells were incubated on ice for 1-hour followed by two washes with PBS (Invitrogen 20012-027) and one wash with a high salt solution (1.5M NaCL, 50 mM HEPES pH 7.4). Wells were extracted with 500 ul of 0.8M NaOH for 30 min. at room temperature and counts per minute were measured in a gamma counter (Packard Cobra II A5005).

The results indicated that 100× molar cold IL-17A and IL-17F were able to reduce binding of $^{125}$I IL-17A to BHK hZcytoR14 by approximately 7 fold while IL-17B,C,D,E and IL-21 had no effect on binding. 100× molar cold IL-17A reduced the binding of $^{125}$I IL-17A to BHK IL-17R by approximately 4 fold while IL-17B,C,D,E,F and IL-21 had no effect on binding. 100× molar cold IL-17A and IL-17F reduced the binding of $^{125}$IL-17F to BHK hZcytoR14 by approximately 4 fold and 5 fold, respectively, while IL-17B, C,D,E and IL-21 had no effect on binding.

B) Binding Inhibition with Soluble Receptor:

Binding to hzytor14 (SEQ ID NO:2) and IL-17R (SEQ ID NO:21) transfected BHK cells was performed as in one, but 100 fold molar excess soluble hZcytoR14x1/Fc9 (Example 8) and soluble IL-17R/Fc (obtained from R&D; Ref. 177-IR) were used in place of cold ligand in the competition. Cells were washed, extracted and counted as in part one.

Soluble hZcytoR14/Fc inhibited binding of $^{125}$IL-17F to BHK hZcytoR14 with an $IC_{50}$ of 10× molar excess average from three experiments. Soluble hZcytoR14/Fc inhibition of $^{125}$I IL-17A on the same cell line gave an average $IC_{50}$ of 20× molar excess and soluble IL-17R/Fc inhibition of $^{125}$I IL-17A gave an average $IC_{50}$ of 20× molar excess.

C) Binding Saturation

Transfected BHK cells were plated into 24-well dishes as in one. Radiolabeled IL-17A and IL-17F were added starting at a concentration of 4 nM in eight 1:3 dilutions (to a concentration of 1.83 pM) in triplicate with a total of 250 μl/well in binding buffer. Separately, 100 fold molar excess of cold ligand was added at each dilution point. Cells were washed, extracted and counted as in one. Specific counts per minute were plotted against concentration of radiolabeled ligand added by subtracting the 100 fold excess counts from the uncompeted counts at each dilution point. These normalized data were plotted to generate saturation binding curves for each combination of radiolabeled ligand and transfected BHK cells. Table 4 shows the affinity values calculated from all three experiments.

TABLE 4

| 125I IL-17A + BHK hZcytoR14 | 125I IL-17A + BHK IL-17R |
|---|---|
| 1. 180 pM | 1. 2.5 +/− 0.2 nM |
| 2. 200 pM | 2. 4.5 +/− 0.3 nM |
| 3. 370 pM | 3. 5.9 +/− 0.1 nM |

| 125I IL-17F + BHK hZcytoR14 | 125I IL-17F + BHK IL-17R |
|---|---|
| 1. 50 pM | 1. Very low affinity |
| 2. 60 pM | 2. Very low affinity |
| 3. 80 pM | 3. Very low affinity |

One-site binding curve fits agreed most closely with IL-17A & IL-17F binding to IL-17R. Two-site binding curve fits agreed most closely with IL-17A and IL-17F binding to hZcytoR14. The high affinity binding site is the value shown above. The low affinity binding site had very low affinity and varied widely between the three experiments.

Example 12

Murine Nih3t3 Cells Respond to Human IL-17A and IL-17F

A) Cell Plating and kz142 Adenovirus Reporter Infection.

Nih3t3 cells, derived from mouse fibroblasts (described in ATCC) Nih3t3 were plated at 5000 cells/well in solid white, cell culture coated 96 well plates, (Cat. #3917. Costar) using DMEM/10% FBS, containing glutamine and amended with pyruvate and cultured overnight at 37° C. and 5% C02. On this second day, the plating media was removed and Kz142 adenovirus particles at a multiplicity of infection of 5000 particles/cell were prepared in DMEM/1% FBS, containing glutamine and amended with pyruvate and cultured overnight at 37° C. and 5% C02.

B) Luciferase Assay Measuring IL-17A and F Activation of kz142 Adenovirus Reporter Infected nih3t3 Cells.

Following the overnight incubation with the adenovirus particle reporter, human IL-17A and IL-17F Ligand treatments were prepared in serum free media ( )mended to 0.28% BSA. The adenovirus particles and media were removed and the appropriate ligand doses were given in triplicates. Incubation at 37° C. and 5% C02 was continued for 4 hours, after which the media was removed, cells lysed for 15 minutes and mean fluorescence intensity (MFI) measured using the luciferase assay system and reagents. (Cat.#e1531 Promega. Madison, Wis.) and a Microplate luminometer. Activity was detected at concentrations ranging from 0.1-1000 ng/ml human IL-17A and IL-17F, generating EC50 values of about 50 ng/ml for both ligands. These data suggest that nih3t3 cells carry receptors to these ligands and that IL-17A and IL-17F activate the NfKb/Ap-1 transcription factor.

Example 13

Murine Nih3t3 Cells Express Both IL-17 Receptor and ZcytoR14 Receptor

RTPCR analysis of nih3t3 RNA demonstrated that these cells are positive for both IL-17 Receptor and ZcytoR14 receptor, consistent with their nfkb/ap1 response to human IL-17A and IL-17F mediation being mediated through one or both of these receptors. RTPCR DETAILS:

A) Mouse cytor14 PCR

First strand cDNA was prepared from total RNA isolated from nih3t3 cells using standard methods. PCR was applied using hot star polymerase and the manufacturer's recommendations (Qiagen, Valencia, Calif.) using sense primer, zc38910, 5' ACGAAGCCCAGGTACCAGAAAGAG 3' (SEQ ID NO:56) and antisense primer, zc 38679, 5' AAAAGCGCCGCAGCCAAGAGTAGG 3' (SEQ ID NO:57) and 35 cycles of amplification. Agarose gel electrophoresis revealed a single, robust amplicon of the expected, 850 by size.

B) Mouse IL-17R PCR

First strand cDNA was prepared from total RNA isolated from nih3t3 cells using standard methods. PCR was applied using hot star polymerase and the manufacturer's recommendations (Qiagen, Valencia, Calif.) using sense primer, zc38520, 5' CGTAAGCGGTGGCGGTTTTC 3'(SEQ ID NO:58) and antisense primer, zc 38521, 5' TGGGCAGGGCACAGTCACAG 3' (SEQ ID NO:59) and 35 cycles of amplification. Agarose gel electrophoresis revealed a single, robust amplicon of the expected, 498 by size.

Example 14

Creation of a Stable Nih3t3 Assay Clone Expressing the ap1/nfkb Transcription Factor The murine nih3t3 cell line described above was stably transfected with the kz142 ap1/nfkb reporter construct, containing a neomycin-selectable marker. The Neo resistant transfection pool was plated at clonal density. Clones were isolated using cloning rings and screened by luciferase assay using the human IL-17A ligand as an inducer. Clones with the highest mean fluorescence intensity (MFI) (via ap1/NfkB luciferase) and the lowest background were selected. A stable transfectant cell line was selected and called nih3t3/kz142.8.

Example 15

Inhibition of Activation by Human IL-17A and IL-17F in Murine Nih3t3 Cells Using Soluble ZcytoR14 and IL-17 Receptor/FC Chimeras Soluble forms of ZcytoR14 or IL-17R were used as antagonists of human IL-17A and IL-17F activation of ap1/nfkb elements in a luciferase assay. These soluble receptors are fusion proteins derived from the extracellular domain of each receptor fused to the human IgG1 constant (Fc) region. The soluble human IL-17R FC fusion protein was purchased. (recombinant human IL-17R/FC chimera, catalog number 177-IR-100, R&D Systems, Inc., Minneapolis, Mn.) The soluble human ZcytoR14FC chimera (ZcytoR14sR/FC9) was constructed as described above. We find that an excess ZcytoR14sR/FC9 and human IL17RsR/FC chimera inhibit EC50 levels of both human IL-17A and IL-17F mediation of ap1/nfkb activation of the murine nih3t3/kz142.8 assay cell line.

The ZcytoR14sR/FC9 protein showed the greatest potency in antagonizing IL-17F activation and IL17RsR/FC chimera showed the greatest potency in antagonizing IL-17A activation.

Example 16

IL-17F mRNA is Upregulated in a Murine Model of Asthma

IL-17F mRNA levels were measured in a sensitization and airway challenge model in mice. Groups of mice, 8 to 10 wks of age, were sensitized by intraperitoneal injection of 10 ug of recombinant *Dermatophagoides pteronyssinus* allergen 1 (DerP1) (Indoor biotechnologies, Cardiff, UK) in 50% Imject Alum (Pierce) on days 0 and 7. Seven days later, mice were challenged on 3 consecutive days (days 14, 15 and 16) with 20 ug of DerP1 in 50 ul PBS. There were 4 mice representing this group. Negative controls included 5 mice given phosphate buffered saline (PBS) sensitization, followed by PBS challenge. In addition to 3 mice given DerP1 sensitization, followed by PBS challenge. Forty-eight hours following allergen, or control challenge whole lung tissue was harvested and total RNA was isolated.

First strand cDNA was prepared using identical amounts of total RNA from each subject. IL-17F PCR was applied using Qiagen hotstar polymerase (Qiagen, Valencia, Calif.) and the manufacturer's recommendations. The IL-17F PCR utilized 35 cycles of amplification with sense primer, zc46098, 5' ACTTGCCATTCTGAGGGAGGTAGC 3' (SEQ ID NO:60) and antisense primer, 46099, 5' CACAGGTGCAGC-CAACTTTTAGGA 3' (SEQ ID NO:61). In order to establish that the template quality was uniform amongst all subjects, Beta Actin PCR was applied to the same amount of each template used in the IL-17F amplification. B actin PCR included 25 cycles of PCR with sense primer, zc44779, 5' GTGGGCCGCTCTAGGCACCA 3' (SEQ ID NO:62) and antisense primer, zcc44776, 5' CGGTTGGCCTTAGGGT-TCAGGGGGG 3' (SEQ ID NO:63).

All 4 mice from the DerP1 sensitized, DerP1 challenged treatment group (the asthma simulation) showed robust IL-17F amplification. In contrast, weak IL-17F amplification was seen from the negative controls, including 3 of 3 subjects representing the DerP1 sensitized/PBS challenged treatment group and 5 of 5 subjects from the PBS sensitized/PBS challenged treatment group. B actin amplification was at least as robust for the negative controls as for the asthma-simulated subjects, demonstrating that the weak negative control IL-17F amplification was not due to template problems.

Example 17

COS Cell Transfection and Secretion Trap

A) Cos Cell Transfection and Secretion Trap Assays Show that ZcytoR14sR/Fc9 and IL-17F is a Receptor/Ligand Pair A secretion trap assay was used to match the human ZcytoR14 (SEQ ID NO:2) to the human IL-17F (SEQ ID NO:16). The soluble ZcytoR14sR/Fc9 fusion protein (Example 8) was used as a binding reagent in a secretion assay. SV40 ori containing expression vectors containing cDNA of human IL-17B,C,D,E, and F was transiently transfected into COS cells. The binding of ZcytoR14sR/Fc9 to transfected COS cells was carried out using the secretion trap assay described below. Positive binding of ZcytoR14sR/Fc9 was only seen to human IL-17F. These results demonstrate the novel finding that human ZcytoR14 and IL-17F is a receptor/ligand pair.
B) COS Cell Transfections The COS cell transfection was performed as follows: Mix 3 ul pooled DNA and 5 ul Lipofectamine™ in 92 ul serum free DMEM media (55 mg sodium pyruvate, 146 mg L-glutamine, 5 mg transferrin, 2.5 mg insulin, 1 µg selenium and 5 mg fetuin in 500 ml DMEM), incubate at room temperature for 30 minutes and then add 400 ul serum free DMEM media. Add this 500 ul mixture onto $1.5 \times 10^5$ COS cells/well plated on 12-well tissue culture plate and incubate for 5 hours at 37° C. Add 500 ul 20% FBS DMEM media (100 ml FBS, 55 mg sodium pyruvate and 146 mg L-glutamine in 500 ml DMEM) and incubate overnight.
C) Secretion Trap Assay The secretion trap was performed as follows: Media was rinsed off cells with PBS and then fixed for 15 minutes with 1.8% Formaldehyde in PBS. Cells were then washed with TNT (0.1M Tris-HCL, 0.15M NaCl, and 0.05% Tween-20 in $H_2O$), and permeated with 0.1% Triton-X in PBS for 15 minutes, and again washed with TNT. Cells were blocked for 1 hour with TNB (0.1M Tris-HCL, 0.15M NaCl and 0.5% Blocking Reagent (NEN Renaissance TSA-Direct Kit) in $H_2O$), and washed again with TNT. The cells were incubated for 1 hour with 1 µg/ml human ZcytoR14x1sR/FC9 soluble receptor fusion protein Cells were then washed with TNT. Cells were incubated for another hour with 1:200 diluted goat-anti-human Ig-HRP (Fc specific). Again cells were washed with TNT.

Positive binding was detected with fluorescein tyramide reagent diluted 1:50 in dilution buffer (NEN kit) and incubated for 4-6 minutes, and washed with TNT. Cells were preserved with Vectashield Mounting Media (Vector Labs Burlingame, Calif.) diluted 1:5 in TNT. Cells were visualized using a FITC filter on fluorescent microscope.

Example 18

Generation of Murine Anti-Human ZcytoR14 Monoclonal Antibodies

A. Immunization for Generation of anti-ZcytoR14 Antibodies
 1. Soluble ZcytoR14-muFc Six to twelve week old intact or ZcytoR14 knockout mice are immunized by intraperitoneal injection with 25-50 ug of soluble human ZcytoR14-muFc protein (Example 23) mixed 1:1 (v:v) with Ribi adjuvant (Sigma) on a biweekly schedule. Seven to ten days following the third immunization, blood samples were taken via retroorbital bleed, the serum harvested and evaluated for its ability to inhibit the binding of IL-17 or IL-17F to ZcytoR14 in neutralization assays (e.g., described herein) and to stain ZcytoR14 transfected versus untransfected 293 cells in a FACS staining assay. Mice continued to be immunized and blood samples taken and evaluated as described above until neutralization titers reached a plateau. At that time, mice with the highest neutralization titers were injected intravascularly with 25-50 ug of soluble ZcytoR14-Fc protein in PBS. Three days later, the spleen and lymph nodes from these mice were harvested and used for hybridoma generation, for example using mouse myeloma (P3-X63-Ag8.653.3.12.11) cells or other appropriate cell lines in the art, using standard methods known in the art (e.g., see Kearney, J. F. et al., *J. Immunol.* 123:1548-50, 1979; and Lane, R. D. *J Immunol Methods* 81:223-8, 1985).

2. Soluble ZcytoR14, ZcytoR14-CEE, ZcytoR14-CHIS, ZcytoR14-CFLAG

Six to twelve week old intact or ZcytoR14 knockout mice are immunized by intraperitoneal injection with 25-50 ug of soluble human ZcytoR14-CEE, ZcytoR14-CHIS, or ZcytoR14-CFLAG mixed 1:1 (v:v) with Ribi adjuvant (Sigma) on a biweekly schedule. Seven to ten days following the third immunization, blood samples are taken via retroorbital bleed, the serum harvested and evaluated for its ability to inhibit the binding of IL-17 or IL-17F to ZcytoR14 in neutralization assays (e.g., described herein) and to stain ZcytoR14 transfected versus untransfected 293 cells in a FACS staining assay. Mice are continued to be immunized and blood samples taken and evaluated as described above until neutralization titers reached a plateau. At that time, mice with the highest neutralization titers are injected intravascularly with 25-50 ug of soluble ZcytoR14, ZcytoR14-CEE, zcytor-CHIS, or ZcytoR14-CFLAG antigen protein in PBS. Three days later, the spleen and lymph nodes from these mice are harvested and used for hybridoma generation, for example using mouse myeloma (P3-X63-Ag8.653.3.12.11) cells or other appropriate cell lines in the art, using standard methods known in the art (e.g., see Kearney, J. F. et al., *J. Immunol.* 123:1548-50, 1979; and Lane, R. D. *J Immunol Methods* 81:223-8, 1985).

3. P815 Transfectants That Express the ZcytoR14

Six to ten week old female DBA/2 mice are immunized by intraperitoneal injection of $1 \times 10^5$ live, transfected P815 cells, for example P815/ZcytoR14 cells (e.g., 0.5 ml at a cell density of $2 \times 10^5$ cells/ml). Prior to injection, the cells are maintained in the exponential growth phase. For injection the cells are harvested, washed three times with PBS and then resuspended in PBS to a density of $2 \times 10^5$ cells/ml. In this model, the mice develop an ascites tumor within 2-3 weeks and progress to death by 4-6 weeks unless an immune response to the transfected target antigen has been mounted. At three weeks mice with no apparent abdominal swelling (indicative of ascites) are re-immunized as above at 2-3 week intervals. Seven to ten days following the second immunization, blood samples are taken via retroorbital bleed, the serum harvested and evaluated for its ability to inhibit the binding of IL-17 or IL-17F to IL-17 or ZcytoR14 in neutralization assays (e.g., described herein) and to stain ZcytoR14 transfected versus untransfected 293 cells in a FACS staining assay. Mice continue to be immunized and blood samples taken and evaluated as described above until neutralization titers reach a plateau. At that time, the mice with the highest neutralization titers are injected intraperitonealy with $1 \times 10^5$ live, transfected P815 cells. Four days later, the spleen and lymph nodes from these mice are harvested and used for hybridoma generation, for example using mouse myeloma (P3-X63-Ag8.653.3.12.11) cells or other appropriate cell lines in the art, using standard methods known in the art (e.g., see Kearney, J. F. et al., supra.; and Lane, R. D. supra.).

An alternative to the above immunization scheme with live, transfected P815 cells involves intraperitoneal injection of $1-5 \times 10^6$ irradiated, transfected cells every 2-3 weeks. In this approach, no animals develop and die of ascites. Instead, animals are monitored for a neutralizing immune response to ZcytoR14 in their serum as outlined above, starting with a bleed after the second immunization. Once neutralization titers have reached a maximal level, the mice with highest titers are given a pre-fusion, intraperitoneal injection of $5 \times 10^6$ irradiated cells and four days later, the spleen and lymph nodes from these mice are harvested and used for hybridoma generation, for example using mouse myeloma (P3-X63-Ag8.653.3.12.11) cells or other appropriate cell lines in the art, using standard methods known in the art (e.g., see Kearney, J. F. et al., supra.; and Lane, R. D. supra.).

B. Screening the Hybridoma Fusions for Antibodies that Bind ZcytoR14 and Inhibit the Binding of IL-17 or IL-17F to ZcytoR14

Three different primary screens are performed on the hybridoma supernatants at 8-10 days post-fusion. For the first assay, antibodies in supernatants were tested for their ability to bind to plate bound soluble human ZcytoR14, ZcytoR14-muFc, ZcytoR14-CEE, ZcytoR14-CHIS, or ZcytoR14-CFLAG protein by ELISA using HRP-conjugated goat anti-mouse kappa and anti-lambda light chain second step reagents to identify bound mouse antibodies. To demonstrate specificity for the ZcytoR14 portion of the ZcytoR14 fusion proteins, positive supernatants in the initial assay were evaluated on an irrelevant protein fused to the same murine Fc region (mG2a), EE sequence, HIS sequence, or FLAG sequence. Antibody in those supernatants that bound to ZcytoR14-fusion protein and not the irrelevant muFc or other proteins containing fusion protein sequence were deemed to be specific for ZcytoR14. For the second assay, antibodies in all hybridoma supernatants were evaluated by ELISA for their ability to inhibit the binding of biotinylated human IL-17 or biotinylated human IL-17F to plate bound ZcytoR14-muFc or ZcytoR14-fusion proteins.

All supernatants containing antibodies that bound specifically to ZcytoR14, whether they inhibited the binding of IL-17 or IL-17F to ZcytoR14 or not in the ELISA assay, were subsequently tested for their ability to inhibit the binding of IL-17 or IL-17F to ZcytoR14 transfected Baf3 or BHK cells or normal human bronchial epithelial cells. All supernatants that were neutralization positive in either the IL-17 or IL-17F inhibition assays or both the IL-17 and IL-17F inhibition assays were subsequently evaluated for their ability to stain ZcytoR14 transfected versus non-transfected Baf3 or BHK cells by FACS analysis. This analysis was designed to confirm that inhibition of IL-17 or IL-17F binding to ZcytoR14, was indeed due to an antibody that specifically binds the ZcytoR14 receptor. Additionally, since the FACS analysis was performed with an anti-IgG second step reagent, specific FACS positive results indicate that the neutralizing antibody was likely to be of the IgG class. By these means, a master well was identified that bound ZcytoR14 in the plate bound ELISA, inhibited the binding of IL-17 or IL-17F to ZcytoR14 in the ELISA based inhibition assay, blocked the interaction of IL-17 and IL-17F with ZcytoR14 transfected Baf3 or BHK cells, respectively, and was strongly positive for the staining of ZcytoR14 transfected Baf3 or BHK cells with an anti-mouse IgG second step reagent.

The third assay consists of primary human bronchial epithelial cells which express ZcytoR14 and can be induced to secrete IL-8 or IL-6 in response to IL-17F treatment. The specific monoclonal antibody is assayed by its ability to inhibit the IL-17 or IL-17F stimulated IL-8 or IL-6 production by these cells. IL-8 and IL-6 production is assayed in response to IL-17 or IL-17F as described herein.

Alternatively, the monoclonal antibody; anti-ZcytoR14, mediated inhibition of IL-17 or IL-17F induced luciferase production in NIH 3T3 or other ZcytoR14 containing cells can be used with or in place of one of the bioactivity neutralization assays noted above. The NFkB mediated luciferase assay in NIH 3T3 cells is described herein.

C) Cloning Anti-ZcytoR14 Specific Antibody Producing Hybridomas

Hybridoma cell lines producing a specific anti-ZcytoR14 mAb that cross-neutralized the binding of IL-17 and IL-17F to appropriately transfected BaF3 or BHK cells are cloned by a standard low-density dilution (less than 1 cell per well) approach. Approximately 5-7 days after plating, the clones are screened by ELISA on, for example, plate bound human ZcytoR14-muFc followed by a retest of positive wells by ELISA on irrelevant muFc containing fusion protein as described above. Selected clones, whose supernatants bind to ZcytoR14-muFc and not the irrelevant muFc containing fusion protein, are further confirmed for specific antibody activity by repeating both neutralization assays as well as the FACS analysis. All selected ZcytoR14 antibody positive clones are cloned a minimum of two times to help insure clonality and to assess stability of antibody production. Further rounds of cloning are performed and screened as described until, preferably, at least 95% of the resulting clones were positive for neutralizing anti-ZcytoR14 antibody production.

D) Biochemical Characterization of the Molecule Recognized by Anti-ZcytoR14 mAbs Biochemical confirmation that the target molecule, ZcytoR14, recognized by the putative anti-ZcytoR14 mAbs is indeed ZcytoR14 are performed by standard immunoprecipitation followed by SDS-PAGE analysis or western blotting procedures, both employing soluble membrane preparations from ZcytoR14 transfected versus untransfected Baf3 or BHK cells. Moreover, soluble membrane preparations of non-transfected cell lines that express ZcytoR14 are used show that the mAbs recognize the native receptor chain as well as the transfected one. Alternatively, the mAbs are tested for their ability to specifically immunoprecipitate or western blot the soluble ZcytoR14-muFc protein.

Example 19

Neutralization of Human ZcytoR14 by Sera from Mice Injected with P815 Cells Transfected with Human ZcytoR14

Using a cell based neutralization assay, serum from mice injected with live human ZcytoR14 transfected P815 cells (Example 17) is added as a serial dilution at 1%, 0.5%, 0.25%, 0.13%, 0.06%, 0.03%, 0.02%, and 0%. The assay plates are incubated at 37 C, 5% $CO_2$ for 4 days at which time Alamar Blue (Accumed, Chicago, Ill.) is added at 20 μl/well. Plates are again incubated at 37 C, 5% $CO_2$ for 16 hours. Results showed that serum from four of the animals could neutralize signaling of both huIL-17 and huIL-17F through human ZcytoR14.

Results such as these provide additional evidence that effectively blocking ZcytoR14 by binding, blocking, inhibiting, reducing, antagonizing or neutralizing IL-17 or IL-17F activity (individually or together), for example via a neutralizing monoclonal antibody to ZcytoR14 of the present invention, could be advantageous in reducing the effects of IL-17 and IL-17F (alone or together) in vivo and may reduce IL-17 and/or IL-17F-induced inflammation, such as that seen in, for example in psoriasis, IBD, colitis, chronic obstructive pulmonary disease, cystic fibrosis or other inflammatory diseases induced by IL-17, and or IL-17F including IBD, arthritis, asthma, psoriatic arthritis, colitis, inflammatory skin conditions, and atopic dermatitis.

Example 20

Pharmacokinetics of an Anti-human ZcytoR14 Monoclonal Antibody

The test monoclonal antibody, anti-human ZcytoR14 mAb, is provided in, for example, 3×3 mL aliquots at a concentration of approximately 1 mg/mL (determined by UV Absorbance at 280 nM) and was stored at −80° C. until use. The vehicle is 1×PBS (50 mM NaPO4, 109 mM NaCl), pH 7.3. The mAb is thawed at room temperature before use and aliquots 1 and 2 are used as provided for the 100 μg IV and SC dosing groups, respectively. Half of aliquot 3 is diluted 1:2 in 1×PBS for the 50 μg SC dose group and the second half of aliquot 3 is diluted 1:10 in 1×PBS for the 10 μg SC dose group. Female SCID mice (n=96) are obtained from Charles River Labs. Animals are checked for health on arrival and group-housed (3 animals per cage). The mice are 12 weeks old with an average body weight of approximately 22 g at the beginning of the study.

A) Dosing Protocol

Female SCID mice (n=24/dose group) are randomly placed into four dosing groups (Table 5). Group 1 was administered the anti-human ZcytoR14 mAb via IV injection of approximately 93 μL in a tail vein and Groups 2, 3, and 4 are administered the mAb via SC injection of approximately 93 μL in the scruff of the neck.

B) Sample Collection

Prior to blood collection, mice were fully anesthetized with halothane or isofluorane. Blood samples were collected via cardiac stick for all time points except the 168 hr timepoint (collected via eye bleed and the same animals were bled again at the 504 hr timepoint via cardiac stick). Blood was collected into serum separator tubes and allowed to clot for 15 minutes. Samples were subsequently centrifuged for 3 minutes at 14,000 rpm. Following centrifugation, aliquots of 125-150 uL were dispensed into labeled eppendorf tubes and immediately stored at −80° C. until analysis.

TABLE 5

| Group # | Dose (ROA) | Animals | PK Timepoints |
| --- | --- | --- | --- |
| 1 | 100 μg (IV) | 3 mice/timepoint* | 0.25, 1, 4, 8, 24, 72, 168, 336 and 504 hr |
| 2 | 100 μg (SC) | 3 mice/timepoint* | 0.25, 1, 4, 8, 24, 72, 168, 336 and 504 hr |
| 3 | 50 μg (SC) | 3 mice/timepoint* | 0.25, 1, 4, 8, 24, 72, 168, 336 and 504 hr |
| 4 | 10 μg (SC) | 3 mice/timepoint* | 0.25, 1, 4, 8, 24, 72, 168, 336 and 504 hr |

*The same animals were used for the 168 and 504 hr timepoints.

C) Quantification of Serum Anti-human ZcytoR14 mAb Concentrations by ELISA

An Enzyme Linked Immunosorbant Assay (ELISA) is developed and qualified to analyze mouse serum samples from animals dosed with anti-ZcytoR14 mAb during pharmacokinetic studies. This assay is designed to take advantage of a commercially available secondary antibody and colorimetric detection using TMB. The dilutions used for the standard curve were modified to improve the definition of the linear portion of the standard curve. A standard curve in the range of 100 ng/mL to 0.231 ng/mL with 2-fold dilutions allows for quantitation of the mouse serum samples. QC samples are diluted to 1:100, 1:1000 and 1:10000 in 10% SCID mouse serum and back calculated from the standard curve.

D) Pharmacokinetic Analysis

Serum concentration versus time data are downloaded into WinNonlin Professional 4.0 software (Pharsight, Inc.; Cary, N.C.) for pharmacokinetic analysis. Noncompartmental analysis is used to determine pharmacokinetic parameters based on the mean data at each time point.

Example 21

Neutralization of IL-17 and IL-17F Activity by a Anti-Human ZcytoR14 Monoclonal Antibody Using a cell-based neutralization assay, a purified mouse anti-human ZcytoR14 monoclonal antibody is added as a serial dilution, for example, at 10 m/ml, 5 m/ml, 2.5 m/ml, 1.25 m/ml, 625 ng/ml, 313 ng/ml, 156 ng/ml and 78 ng/ml. The assay plates are incubated at 37° C., 5% $CO_2$ for 4 days at which time Alamar Blue (Accumed, Chicago, Ill.) is added at 20 μl/well. Plates are again incubated at 37 C, 5% $CO_2$ for 16 hours. This assay is able to demonstrate that the purified anti-human ZcytoR14 monoclonal antibody is able neutralize signaling of both huIL-17 and huIL-17F through human ZcytoR14. For highly effective antibodies, when used at approx. 10 m/ml concentration, the antibody completely neutralizes proliferation induced by huIL-17 or huIL-17F, with the inhibition of proliferation decreasing in a dose dependent fashion at the lower concentrations. An isotype-matched negative control mouse mAb, tested at the concentrations described above, is expected to provide no inhibition of proliferation of either cytokine. These results are able to further demonstrate that monoclonal antibodies to ZcytoR14 could indeed antagonize the activity of the pro-inflammatory ligands, IL-17 and IL-17F at low concentrations.

Example 22

IL-17A Induces Elevated Levels of IFN-gamma and TNF-alpha in Human Peripheral Blood Mononuclear Cells Human peripheral blood mononuclear cells (PBMC) are purified by ficoll density gradient centrifugation and then incubated overnight at 37° C. in media alone, 50 ng/ml anti-human CD3 antibody, or the combination of 50 ng/ml anti-human CD3 antibody plus 1 g/ml anti-human CD28 antibody. Replicate cultures for each of these conditions are set up and are given no cytokine, 25 ng/ml human IL-17A, or 25 ng/ml human IL-17F. After 24-hour incubations, supernatants from each culture are harvested and assayed for cytokine content using B-D Bioscience's human Th1/Th2 Cytometric Bead Array (CBA). We found that cultures that had been stimulated with either anti-CD3 or anti-CD3 plus anti-CD28 and had been supplemented with IL-17A contained significantly elevated levels of IFN-gamma and TNF-alpha (3-5-fold elevation of each) over cultures with no cytokine added or those that received IL-17F. Cultures in which no anti-CD3 stimulation was added did not show significant changes in cytokine levels. In addition, IL-17A addition induced no significant changes in other cytokines assayed for with the CBA including IL-2, IL-4, IL-5, and IL-10. This data indicates that IL-17A, but not IL-17F, can augment the production of IFN-gamma and TNF-alpha in PBMC cultures stimulated with anti-CD3 or anti-CD3 plus anti-CD28.

Example 23

ZcytoR14-Fc Decreases Disease Incidence and Progression in Mouse Collagen Induced Arthritis (CIA) Model A) Mouse Collagen Induced Arthritis (CIA) Model Ten week old male DBA/1J mice (Jackson Labs) are divided into 3 groups of 13 mice/group. On day-21, animals are given an intradermal tail injection of 50-100 µl of 1 mg/ml chick Type II collagen formulated in Complete Freund's Adjuvant (prepared by Chondrex, Redmond, Wash.), and three weeks later on Day 0 they are given the same injection except prepared in Incomplete Freund's Adjuvant. ZcytoR14-Fc is administered as an intraperitoneal injection 3 times a week for 4 weeks, at different time points ranging from Day 0, to a day in which the majority of mice exhibit moderate symptoms of disease. Groups receive either 10 or 100 µg of ZcytoR14-Fc per animal per dose, and control groups receive the vehicle control, PBS (Life Technologies, Rockville, Md.) Animals begin to show symptoms of arthritis following the second collagen injection, with most animals developing inflammation within 1.5-3 weeks. The extent of disease is evaluated in each paw by using a caliper to measure paw thickness, and by assigning a clinical score (0-3) to each paw: 0=Normal, 0.5=Toe(s) inflamed, 1=Mild paw inflammation, 2=Moderate paw inflammation, and 3=Severe paw inflammation as detailed below.

B) Monitoring Disease

Animals can begin to show signs of paw inflammation soon after the second collagen injection, and some animals may even begin to have signs of toe inflammation prior to the second collagen injection. Most animals develop arthritis within 1.5-3 weeks of the boost injection, but some may require a longer period of time. Incidence of disease in this model is typically 95-100%, and 0-2 non-responders (determined after 6 weeks of observation) are typically seen in a study using 40 animals. Note that as inflammation begins, a common transient occurrence of variable low-grade paw or toe inflammation can occur. For this reason, an animal is not considered to have established disease until marked, persistent paw swelling has developed.

All animals are observed daily to assess the status of the disease in their paws, which is done by assigning a qualitative clinical score to each of the paws. Every day, each animal has its 4 paws scored according to its state of clinical disease. To determine the clinical score, the paw can be thought of as having 3 zones, the toes, the paw itself (manus or pes), and the wrist or ankle joint. The extent and severity of the inflammation relative to these zones is noted including: observation of each toe for swelling; torn nails or redness of toes; notation of any evidence of edema or redness in any of the paws; notation of any loss of fine anatomic demarcation of tendons or bones; evaluation of the wrist or ankle for any edema or redness; and notation if the inflammation extends proximally up the leg. A paw score of 1, 2, or 3 is based first on the overall impression of severity, and second on how many zones are involved. The scale used for clinical scoring is shown below.

C) Clinical Score

0=Normal 0.5=One or more toes involved, but only the toes are inflamed

1=mild inflammation involving the paw (1 zone), and may include a toe or toes

2=moderate inflammation in the paw and may include some of the toes and/or the wrist/ankle (2 zones)

3=severe inflammation in the paw, wrist/ankle, and some or all of the toes (3 zones)

Established disease is defined as a qualitative score of paw inflammation ranking 2 or more, that persists for two days in a row. Once established disease is present, the date is recorded and designated as that animal's first day with "established disease".

Blood is collected throughout the experiment to monitor serum levels of anti-collagen antibodies, as well as serum immunoglobulin and cytokine levels. Serum anti-collagen antibodies correlate well with severity of disease Animals are euthanized on Day 21, and blood collected for serum and CBC's. From each animal, one affected paw is collected in 10% NBF for histology and one is frozen in liquid nitrogen and stored at −80° C. for mRNA analysis. Also, ½ spleen, ½ thymus, ½ mesenteric lymph node, one liver lobe and the left kidney are collected in RNAlater for RNA analysis, and ½ spleen, ½ thymus, ½ mesenteric lymph node, the remaining liver, and the right kidney are collected in 10% NBF for histology. Serum is collected and frozen at −80° C. for immunoglobulin and cytokine assays.

Groups of mice receiving ZcytoR14-Fc at all time points are characterized by a delay in the onset and/or progression of paw inflammation. These results indicate that ZcytoR14 can reduce inflammation, as well as disease incidence and progression associated with this model. These results are further supported by the observation that ZcytoR14-Fc resulted in decreased levels of serum TNFα, IL-1b, and anti-collagen antibodies.

Example 24

Stable Over-Expression of ZcytoR14 in the Murine Assay Cell Line, Nih3t3/kz142.8 Expressing the ap1/nfkb Transcription Factor The murine nih3t3/kz142.8 assay cell line was transfected with a human zcytor14x1 (SEQ ID NO:2) in an expression vector with a methotrexate resistance gene (dihydrofolate reductase, DHFR) This transfection was performed using a commercially available kit and the manufacturer's recommendations. (Mirus, Madison, Wis. Cat. #MIR218) Cells were placed in 1 µM mtx amended growth medium to select for the expression vector containing the human zcytor14X1 transgene. After selection a human zcytor14x1 transfection pool was generated, and called nih3t3/kz142.8/hcytor14x1.

A) Luciferase Assay Using the nih3t3/kz142.8 Assay Cell Line

Since nih3t3/kz142.8 has a stable kz142 reporter, there is no need for adenovirus infection to add this reporter. Thus the luciferase assay protocol was shorted and done the following way:

1. Cell Plating nih3t3/kz142.8 cells were plated at 5000 cells/well in solid white, cell culture coated 96 well plates, (Cat. #3917. Costar) using DMEM/10% FBS, containing glutamine and amended with pyruvate and cultured overnight at 37° C. and 5% C02. On this second day, the plating media was removed and exchanged for DMEM/1% FBS, containing glutamine and amended with pyruvate and cultured overnight at 37° C. and 5% C02.

2. Luciferase Assay Measuring IL-17A and F Activation of the Stable kz142 Reporter Following the overnight incubation in the 1% fbs, DMEM media, human IL-17A, and IL-17F ligand dilutions were made in serum free media, amended with BSA to a 0.28% level. After adding the ligand dilutions, cells were incubated at 37° C. and 5% C02 for 4 hours, after which the media was removed, cells lysed for 15 minutes and mean fluorescence intensity (MFI) measured using the luciferase assay system and reagents, (Cat.#e1531 Promega. Madison, Wis.) and a Microplate luminometer. Activity was detected for both ligands at concentrations ranging from 0.1-1000 ng/ml. The nih3t3/kz142.8/hcytor14x1 transfection pool showed similar activity for the murine IL-17A ligand as did the parental cell line. (example 14) However, the cytor14x1 transfectant pool showed an elevated responsiveness to human IL-17A and F treatments, even when these ligand concentrations were as low as 20 femptograms. The fact that the mIL-17A signaling is comparable to that in the parental cell line (example 14) suggests that there isn't a general, non-specific problem with human ZcytoR14-expressing cells and that the murine IL-17A is probably signaling through the endogenous murine nih3t3 cell IL-17R or ZcytoR14 receptor. Thus, the fact that human IL-17A and IL-17F cause an elevation of MFI at such low ligand concentrations may indicate a specific hyper-responsiveness of the cells to those ligands, which is mediated through the over-expressed human ZcytoR14 receptor.

This result has significant clinical and biological ramifications and utility. For example, physiological situations could cause local up-regulation of the ZcytoR14 receptors which could then make these areas hyper-responsive to IL-17A and IL-17F, resulting in biological activation at much lower ligand concentrations than those suggested without ZcytoR14 over-expression. Thus, far lower soluble receptor levels may be sufficient to antagonize these hypothetically lower ligand concentrations, than previously thought or recognized by those in the field.

Example 25

Antagonists to IL-17F and IL-17A activity Decrease Disease Incidence and Progression in an Inflammatory Bowel Disease (IBD) Model This model is designed to show that cultured intestinal tissue from patients with IBD produce higher levels of inflammatory mediators compared to tissue from healthy controls. This enhanced production of inflammatory mediators (including but not limited to IL-1b, IL-4, IL-5, IL-6, IL-8, IL-12, IL-13, IL-15, IL-17 A and F, IL-18, IL-23, TNF-a, IFN-g, MIP family members, MCP-1, G- and GM-CSF, etc.) contributes to the symptoms and pathology associated with IBDs such as Crohn's disease (CD) and ulcerative colitis (UC) by way of their effect(s) on activating inflammatory pathways and downstream effector cells. These pathways and components then lead to tissue and cell damage/destruction observed in vivo. Therefore, this model can simulate this enhanced inflammatory mediator aspect of IBD. Furthermore, when intestinal tissue from healthy controls or from human intestinal epithelial cell (IEC) lines is cultured in the presence of these inflammatory components, inflammatory pathway signaling can be observed, as well as evidence of tissue and cell damage.

Therapeutics that would be efficacious in human IBD in vivo would work in the above ex vivo or IEC models by inhibiting and/or neutralizing the production and/or presence of inflammatory mediators.

In this model, human intestinal tissue is collected from patients with IBD or from healthy controls undergoing intestinal biopsy, re-sectioning or from post-mortem tissue collection, and processed using a modification of Alexakis et al (Gut 53:85-90; 2004). Under aseptic conditions, samples are gently cleaned with copious amounts of PBS, followed by culturing of minced sections of tissue, in the presence of complete tissue culture media (plus antibiotics to prevent bacterial overgrowth). Samples from the same pool of minced tissue are treated with one of the following: vehicle (PBS); recombinant human (rh) IL-17A; rhIL-17F; or rhIL-17A+rhIL-17F. In addition, these are treated with or without an antagonist of either IL-17A or IL-17F, alone or in combination (such as a soluble ZcytoR14). This experimental protocol is followed for studies with human IEC lines, with the exception that cells are passaged from existing stocks. After varying times in culture (from 1 h to several days), supernatants are collected and analyzed for levels of inflammatory mediators, including those listed above. In samples from patients with IBD or in samples treated with rhIL-17A and/or F, levels of inflammatory cytokines and chemokines are elevated compared to untreated healthy control tissue samples. The addition of antagonists to IL-17F and/or IL-17A activity, such as ZcytoR14 soluble receptors and antibodies thereto including the anti-human-ZcytoR14 monoclonal and neutralizing antibodies of the present invention markedly reduces the production of inflammatory mediators, and thus, would expect to be efficacious in human IBD.

Example 26

Antagonists to IL-17F and IL-17A Activity Decrease Disease Incidence and Progression in a Multiple Sclerosis (MS) Model Multiple sclerosis (MS) is a complex disease that is thought to be mediated by a number of factors, including the presence of lymphocytic and mononuclear cell inflammatory infiltrates and demyelination throughout the CNS. Microglia are macrophage-like cells that populate the central nervous system (CNS) and become activated upon injury or infection. Microglia have been implicated as playing critical roles in various CNS diseases including MS, and may be used to study mechanism(s) of initiation, progression, and therapy of the disease (Nagai et al. Neurobiol Dis 8:1057-1068; 2001; Olson et al. J Neurosci Methods 128:33-43; 2003) Immortalized human microglial cell lines and/or established human astroglia cell lines can, therefore, be used to study some of the effects of inflammatory mediators on these cell types and their potential for neutralization. Inflammatory mediators (including but not limited to IL-1b, IL-6, IL-8, IL-12, IL-13, IL-15, IL-17 A and F, IL-18, IL-23, TNF-a, IFN-g, MIP family members, RANTES, IP-10, MCP-1, G- and GM-CSF, etc.) can contribute to the symptoms and pathology associated with MS by way of their effect(s) on activating inflammatory pathways and downstream effector cells.

In order to evaluate the pro-inflammatory actions of IL-17A and IL-17F, and the ability of an antagonist to IL-17F and/or IL-17A activity, such as ZcytoR14 soluble receptors and antibodies thereto including the anti-human-ZcytoR14 monoclonal and neutralizing antibodies of the present invention to neutralize or decrease these effects, cultured glial cells are treated with one of the following: vehicle; rhIL-17A; rhIL-17F; rhIL-17A+IL-17F. In addition, these are treated with or without an antagonist of either IL-17A or IL-17F, alone or in combination (such as a soluble ZcytoR14). After varying times in culture (from 1 h to several days), supernatants and cells are collected and analyzed for levels and/or expression of inflammatory mediators, including those listed above. Levels of inflammatory cytokines and chemokines are elevated in the presence of rhIL-17A and/or IL-17F compared to cultures treated with vehicle alone. The addition of antagonists to IL-17F and/or IL-17A activity, such as ZcytoR14 soluble receptors and antibodies thereto including the anti-human-ZcytoR14 monoclonal and neutralizing antibodies of the present invention markedly reduces the production and expression of inflammatory mediators, and thus, would expect to be efficacious in inflammatory aspects associated with human MS.

Example 27

Antagonists to IL-17F and IL-17A Activity Decrease Disease Incidence and Progression in a Rheumatoid Arthritis (RA) and Osteoarthritis (OA) Model This model is designed to show that human synovial cultures (including synovial macrophages, synovial fibroblasts, and articular chondrocytes) and explants from patients with RA and OA produce higher levels of inflammatory mediators compared to cultures/explants from healthy controls. This enhanced production of inflammatory mediators (including but not limited to oncostatin M, IL-1b, IL-6, IL-8, IL-12, IL-15, IL-17 A and F, IL-18, IL-23, TNF-a, IFN-g, IP-10, RANTES, RANKL, MIP family members, MCP-1, G- and GM-CSF, nitric oxide, etc.) contributes to the symptoms and pathology associated with RA and OA by way of their effect(s) on activating inflammatory pathways and downstream effector cells. These pathways and components then lead to inflammatory infiltrates, cartilage and matrix loss/destruction, bone loss, and upregulation of prostaglandins and cyclooxygenases. Therefore, this model can simulate the destructive inflammatory aspects of RA and OA in in vitro and ex vivo experiments. Furthermore, when explants and synovial cultures from healthy controls are cultured in the presence of several of these inflammatory components (e.g. oncostatin M, TNF-a, IL-1b, IL-6, IL-17A and F, IL-15, etc.), inflammatory pathway signaling can be observed. Therapeutics that would be efficacious in human RA in vivo would work in the above in vitro and ex vivo models by inhibiting and/or neutralizing the production and/or presence of inflammatory mediators.

In this model, human synovial explants are collected from patients with RA, OA, or from healthy controls undergoing joint replacement or from post-mortem tissue collection, and processed using a modification of Wooley and Tetlow (Arthritis Res 2: 65-70; 2000) and van't H of et al (Rheumatology 39:1004-1008; 2000). Cultures of synovial fibroblasts, synovial macrophages and articular chondrocytes are also studied. Replicate samples are treated with one of the following: vehicle (PBS); recombinant human (rh) IL-17A; rhIL-17F; or rhIL-17A+rhIL-17F, and some samples contain various combinations of oncostatin M, TNF-a, IL-1b, IL-6, IL-17A, IL-17F, and IL-15. In addition, these are treated with or without an antagonist to IL-17F and/or IL-17A activity, such as ZcytoR14 soluble receptors and antibodies thereto including the anti-human-ZcytoR14 monoclonal and neutralizing antibodies of the present invention. After varying time of culture (from 1 h to several days), supernatants are collected and analyzed for levels of inflammatory mediators, including those listed above. In samples from patients with RA or OA, or in samples treated with rhIL-17A and/or F (either alone or in combination with other inflammatory cytokines), levels of inflammatory cytokines and chemokines are elevated compared to untreated healthy control explants or in untreated cell cultures. The addition of antagonists to IL-17F and/or IL-17A activity, such as ZcytoR14 soluble receptors and antibodies thereto including the anti-human-ZcytoR14 monoclonal and neutralizing antibodies of the present invention markedly reduces the production of inflammatory mediators, and thus, would expect to be efficacious in human RA and OA.

Example 28

IL-17A and IL-17F Functional Responses

NIH-3T3/KZ142 cells were stably transfected with human zcytoR14x1 (SEQ ID NO:1) and mouse zcytoR14x1 (SEQ ID NO:25). As described above, each line was treated for 7 and 15 minutes with a dose response of IL-17A, IL-17F, murine IL-17F, and appropriate controls. Both IL-17A and IL-17F gave a dose dependent response in phosphorylated IκB-α and p38 MAPK transcription factors when ZcytoR14x1 (SEQ ID NO:1) was transfected, approximately 30% greater then the inherent signaling from the control line. IL-17A and IL-17F gave no increase in signaling when the murine ZcytoR14x1 (SEQ ID NO:25) was transfected. Murine IL-17F gave no increase in signaling for either human or murine ZcytoR14x1.

Example 29

IL-17A, IL-17F, IL-17R and ZcytoR14 Expression in Murine Disease Models

Four murine models of disease (asthma, DSS colitis, atopic dermatitis and experimental allergic encephalomyelitis) were analyzed using know techniques for the expression of IL-17A, IL-17F, IL-17R and ZcytoR14.

In the asthma model, IL-17A and IL-17F are expressed at very low to undetectable levels in lung, spleen, lung draining lymph nodes and lung infiltrating cells in diseased and non-diseased mice. Zcytor14 message was found to be more highly expressed in lung compared to spleen and lymph node but was not regulated with disease. IL-17R was more highly expressed in spleen and lung draining lymph node compared to lung but was also not regulated with disease.

Contrary to the asthma model, IL-17A and IL-17F were highly up-regulated in diseased but not normal mice in the DSS-colitis model in both proximal and distal colon. Neither cytokine was significantly up-regulated in the mesenteric lymph node. Further, it was found that up-regulation of both cytokines in the context of acute DSS-induced colitis and not in chronic DSS-induced colitis. IL-17R was found to be prominently expressed in mesenteric lymph nodes as compared to proximal and distal colon, but was not regulated with disease. In contrast, ZcytoR14 was more highly expressed in proximal distal colon tissue compared to mesenteric lymph nodes. ZcytoR14 expression was also not regulated with disease.

In atopic dermatitis, IL-17A mRNA was not detectable. IL-17F was found to be expressed in both skin and skin-draining lymph nodes but did not appear to be significantly regulated with disease. IL-17R mRNA was more highly expressed in skin-draining lymph nodes as compared to skin but was not regulated with disease. Zcytor14 was more highly expressed in skin compared to skin-draining lymph nodes but was also not regulated with disease.

In experimental allergic encephalomyelitis, both IL-17A and IL-17F appeared to up-regulated in spinal chord in diseased but not healthy mice. IL-17F may have been more highly expressed in lymph nodes compared to spinal cord but expression in the lymph nodes was not regulated with disease. However, overall levels of expression in these tissues was quite low. IL-17R was more highly expressed in lymph node tissue compared to brain and spinal cord. Zcytor14 was not tested.

In short, IL-17A and IL-17F expression appears to be regulated with disease in the context of the DSS-induced colitis and experimental allergic encephalomyelitis models but apparently not for asthma or atopic dermatitis. IL-17R and zcytor14 expression does not appear to be regulated with disease but IL-17R expression appears to be enriched in lymphoid tissues while zcytor14 expression appears to be enriched in non-lymphoid tissues.

Example 30

ZcytoR14 is a Mediator of Activation to Both IL-17A and IL-17F

The murine nih3t3/kz142.8 assay cell line was transfected with a human ZcytoR14X1 (SEQ ID NO:2) in an expression vector with a methotrexate resistance gene. (dihydrofolate reductase, DHFR) Human IL-17RA (SEQ ID NO:21) was similarly transfected into this cell line. Transfections were performed using a commercially available kit and the manufacturer's recommendations. (Mirus, Madison, Wis. Cat. #MIR218) Cells were placed in 1 μM mtx amended growth medium to select for the expression vector containing the expression constructs. After selection transfection pools were generated, and called nih3t3/kz142.8/hcytor14X1 and nih3t3/kz142.8/IL-17R.
A) Luciferase Assay Using the nih3t3/kz142.8-Based Cell Lines.

Since nih3t3/kz142.8 based cell lines have stable ap1/nfkb reporters (kz142), there is no need for adenovirus infection to add this reporter. Thus the luciferase assay protocol was shorted and done the following way:
1. Cell Plating Cells were plated at 5000 cells/well in solid white, cell culture coated 96 well plates, (Cat. #3917. Costar) using DMEM/10% FBS, containing glutamine and amended with pyruvate and cultured overnight at 37° C. and 5% C02. On this second day, the plating media was removed and exchanged for DMEM/1% FBS, containing glutamine and amended with pyruvate and cultured overnight at 37° C. and 5% C02.
2. Luciferase Assay Measuring IL-17A and F Activation of the Stable kz142 Reporter Following the overnight incubation in the 1% fbs, DMEM media, human IL-17A, and IL-17F ligand dilutions were made in serum free media, amended with BSA to a 0.28% level. After adding the ligand dilutions, cells were incubated at 37° C. and 5% C02 for 4 hours, after which the media was removed, cells lysed for 15 minutes and mean fluorescence intensity (MFI) measured using the luciferase assay system and reagents, (Cat.#e1531 Promega. Madison, Wis.) and a Microplate luminometer. Activity was detected for both ligands at concentrations ranging from 0.1-100 ng/ml.

The $EC_{50s}$ discussed below are averages of at least 4 experiments. The nih3t3/kz142.8/hcytor14x1 transfection pool showed similar activity for the murine IL-17A ligand as did the parental cell line, with an $EC_{50}$ of about 4 ng/ml. (example 14) The fact that the mIL-17A signaling in the hcytor14x1 recombinant line is comparable to that in the parental cell line (example 14) suggests that murine IL-17A is probably signaling through the endogenous murine nih3t3 cell IL-17RA or zcytor14 receptors and does not activate the cells through hcytor14X1. However, the hzcytor14X1 transfectant pool showed an elevated responsiveness to human IL-17A treatment, with an $EC_{50}$ of 0.41 ng/ml Vs 2.8 ng/ml (averages of 4 experiments) in the parental line (a 6.8 fold more potent $EC_{50}$ in the recombinant line) In addition, the hIL-17RCX1 recombinant line had an enhanced responsiveness to hIL-17F, with an $EC_{50}$ of 0.61 ng/ml in the recombinant line Vs 10 ng/ml in the parental line. (a 17 fold more potent $EC_{50}$ in the recombinant line). The increased potency to hIL-17A and F in the hIL-17RCX1 line is consistent with human zcytor14X1 being a high affinity receptor for both human IL-17A and IL-17F. In contrast, the hIL-17RA recombinant line had enhanced sensitivity only to hIL-17A, with an $EC_{50}$ of 0.6 ng/ml vs 2.8 ng/ml for the parental line. There was not an enhancement of the hIL-17F $EC_{50}$ in the hIL-17RA recombinant line, with an IL-17F $EC_{50}$ of 12.4 ng/ml vs 8.9 ng/ml in the parental line.

This result is significant because it specifically implicates hzcytor14X1 as a mediator of activation to both hIL-17A and hIL-17F and suggests that hIL-17RA mediates signaling only to hIL-17A activation and not hIL-17F.

Example 31

Intravenous Administration of IL-17A and IL-17F

To determine the effect of i.v. delivery of murine or human IL-17A or IL-17F on complete blood counts (CBC) and serum cytokines/chemokines in BALB/c mice at various time points.

I.V. administration of 1 ug mIL-17A resulted in an approximate 2-fold increase in circulating neutrophils (by CBC) and approximate 10-fold increase in serum KC and MCP-1 (by Luminex) 1-2 h following administration; similar results in these chemokines were observed with 5 ug hIL-17A. Blood monocyte levels were also significantly increased in mice treated with 1 ug mIL-17A (showed the greatest increase), 5 ug hIL-17A or 5 ug hIL-17F at the 2 h timepoint. I.V. administration of m and hIL-17F resulted in marked increases in serum IL-15 (by Luminex) at the 1 and 2 h time points, and small increases in serum KC and MCP-1 at these same timepoints.

Example 32

Neutralization of i.v. Administered IL-17A and IL-17F

To neutralize the i.v. IL-17A and IL-17F-mediated increases in cytokines and chemokines with i.p. soluble receptors (mIL-17RA:Fc for murine ligands; soluble human ZcytoR14 for human ligands). Female BALB/c mice were administered by i.p. injection either PBS, 100 ug mIL-17RA: Fc, or 100 ug soluble human ZcytoR14 three hours prior to receiving by i.v. tail injection: PBS; 2 ug of either mIL-17A, mIL-17F, or 2 ug of both mIL-17A and F (for mice that received mIL-17RA:Fc); or 2 ug of either hIL-17A, hIL-17F, or 2 ug of both hIL-17A and F (for mice that received soluble human ZcytoR14). Serum was collected 1 h following ligand administration and analyzed for a small number of serum cytokines and chemokines.

Mice pretreated with i.p. soluble receptor had marked reductions in IL-17A-mediated increases in serum concentrations of IL-17A and KC compared to mice treated with PBS+IL-17A.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating a human afflicted with multiple sclerosis (MS), the method comprising:
administering to the human afflicted with MS an effective amount of an antagonist of both IL-17A and IL-17F, wherein the antagonist is selected from
(i) an antibody or antibody fragment that binds to a polypeptide consisting of the amino acid sequence as shown in SEQ ID NO:3, wherein the antibody or antibody fragment is capable of inhibiting the interaction of either IL-17A or IL-17F with a polypeptide having the amino acid sequence of SEQ ID NO:2; and
(ii) a soluble receptor protein comprising a polypeptide having the amino acid sequence as set forth in SEQ ID NO:3 or a fragment thereof that is capable of binding IL-17A or IL-17F;
wherein the inflammatory activity of both IL-17A and IL-17F in the human is reduced.

2. The method of claim 1, wherein the antagonist of both IL-17A and IL-17F is the soluble receptor protein of (ii).

3. The method of claim 2, wherein the soluble receptor protein is a soluble fusion protein.

4. The method of claim 3, wherein the soluble fusion protein comprises a immunoglobulin heavy chain constant region.

5. The method of claim 4, wherein the immunoglobulin heavy chain constant region is an Fc fragment.

6. The method of claim 1, wherein the antagonist of both IL-17A and IL-17F is PEGylated.

* * * * *

SEQUENCE LISTING

```
<160> NUMBER OF SEQ ID NOS: 66

<210> SEQ ID NO 1
<211> LENGTH: 2255
<212> TYPE: DNA
<213> ORGANISM: Homo sapiens
<220> FEATURE:
<221> NAME/KEY: CDS
<222> LOCATION: (154)...(2229)

<400> SEQUENCE: 1
aactacccag cacagccccc tccgcccct  ctggaggctg aagagggatt ccagcccctg       60
ccacccacag acacgggctg actggggtgt ctgcccccct tgggggggggg cagcacaggg     120 cctcaggcct gggtgccacc tggcacctag aag atg cct gtg ccc tgg ttc ttg      174
                                     Met Pro Val Pro Trp Phe Leu
                                      1               5 ctg tcc ttg gca ctg ggc cga agc cca gtg gtc ctt tct ctg gag agg       222
Leu Ser Leu Ala Leu Gly Arg Ser Pro Val Val Leu Ser Leu Glu Arg
           10                  15                  20 ctt gtg ggg cct cag gac gct acc cac tgc tct ccg ggc ctc tcc tgc       270
Leu Val Gly Pro Gln Asp Ala Thr His Cys Ser Pro Gly Leu Ser Cys
     25                  30                  35 cgc ctc tgg gac agt gac ata ctc tgc ctg cct ggg gac atc gtg cct       318
Arg Leu Trp Asp Ser Asp Ile Leu Cys Leu Pro Gly Asp Ile Val Pro
 40                  45                  50                  55 gct ccg ggc ccc gtg ctg gcg cct acg cac ctg cag aca gag ctg gtg       366
Ala Pro Gly Pro Val Leu Ala Pro Thr His Leu Gln Thr Glu Leu Val
                 60                  65                  70 ctg agg tgc cag aag gag acc gac tgt gac ctc tgt ctg cgt gtg gct       414
Leu Arg Cys Gln Lys Glu Thr Asp Cys Asp Leu Cys Leu Arg Val Ala
             75                  80                  85 gtc cac ttg gcc gtg cat ggg cac tgg gaa gag cct gaa gat gag gaa       462
Val His Leu Ala Val His Gly His Trp Glu Glu Pro Glu Asp Glu Glu
         90                  95                 100 aag ttt gga gga gca gct gac tca ggg gtg gag gag cct agg aat gcc       510
Lys Phe Gly Gly Ala Ala Asp Ser Gly Val Glu Glu Pro Arg Asn Ala
    105                 110                 115 tct ctc cag gcc caa gtc gtg ctc tcc ttc cag gcc tac cct act gcc       558
Ser Leu Gln Ala Gln Val Val Leu Ser Phe Gln Ala Tyr Pro Thr Ala
120                 125                 130                 135 cgc tgc gtc ctg ctg gag gtg caa gtg cct gct gcc ctt gtg cag ttt       606
Arg Cys Val Leu Leu Glu Val Gln Val Pro Ala Ala Leu Val Gln Phe
                140                 145                 150 ggt cag tct gtg ggc tct gtg gta tat gac tgc ttc gag gct gcc cta      654
Gly Gln Ser Val Gly Ser Val Val Tyr Asp Cys Phe Glu Ala Ala Leu
            155                 160                 165 ggg agt gag gta cga atc tgg tcc tat act cag ccc agg tac gag aag      702
Gly Ser Glu Val Arg Ile Trp Ser Tyr Thr Gln Pro Arg Tyr Glu Lys
        170                 175                 180 gaa ctc aac cac aca cag cag ctg cct gcc ctg ccc tgg ctc aac gtg      750
Glu Leu Asn His Thr Gln Gln Leu Pro Ala Leu Pro Trp Leu Asn Val
```

-continued

```
            185                 190                 195
tca gca gat ggt gac aac gtg cat ctg gtt ctg aat gtc tct gag gag     798
Ser Ala Asp Gly Asp Asn Val His Leu Val Leu Asn Val Ser Glu Glu
200                 205                 210                 215 cag cac ttc ggc ctc tcc ctg tac tgg aat cag gtc cag ggc ccc cca     846
Gln His Phe Gly Leu Ser Leu Tyr Trp Asn Gln Val Gln Gly Pro Pro
            220                 225                 230 aaa ccc cgg tgg cac aaa aac ctg act gga ccg cag atc att acc ttg     894
Lys Pro Arg Trp His Lys Asn Leu Thr Gly Pro Gln Ile Ile Thr Leu
                235                 240                 245 aac cac aca gac ctg gtt ccc tgc ctc tgt att cag gtg tgg cct ctg     942
Asn His Thr Asp Leu Val Pro Cys Leu Cys Ile Gln Val Trp Pro Leu
            250                 255                 260 gaa cct gac tcc gtt agg acg aac atc tgc ccc ttc agg gag gac ccc     990
Glu Pro Asp Ser Val Arg Thr Asn Ile Cys Pro Phe Arg Glu Asp Pro
265                 270                 275 cgc gca cac cag aac ctc tgg caa gcc gcc cga ctg cga ctg ctg acc    1038
Arg Ala His Gln Asn Leu Trp Gln Ala Ala Arg Leu Arg Leu Leu Thr
280                 285                 290                 295 ctg cag agc tgg ctg ctg gac gca ccg tgc tcg ctg ccc gca gaa gcg    1086
Leu Gln Ser Trp Leu Leu Asp Ala Pro Cys Ser Leu Pro Ala Glu Ala
                300                 305                 310 gca ctg tgc tgg cgg gct ccg ggt ggg gac ccc tgc cag cca ctg gtc    1134
Ala Leu Cys Trp Arg Ala Pro Gly Gly Asp Pro Cys Gln Pro Leu Val
            315                 320                 325 ccg ccg ctt tcc tgg gag aac gtc act gtg gac aag gtt ctc gag ttc    1182
Pro Pro Leu Ser Trp Glu Asn Val Thr Val Asp Lys Val Leu Glu Phe
                330                 335                 340 cca ttg ctg aaa ggc cac cct aac ctc tgt gtt cag gtg aac agc tcg    1230
Pro Leu Leu Lys Gly His Pro Asn Leu Cys Val Gln Val Asn Ser Ser
345                 350                 355 gag aag ctg cag ctg cag gag tgc ttg tgg gct gac tcc ctg ggg cct    1278
Glu Lys Leu Gln Leu Gln Glu Cys Leu Trp Ala Asp Ser Leu Gly Pro
360                 365                 370                 375 ctc aaa gac gat gtg cta ctg ttg gag aca cga ggc ccc cag gac aac    1326
Leu Lys Asp Asp Val Leu Leu Leu Glu Thr Arg Gly Pro Gln Asp Asn
                380                 385                 390 aga tcc ctc tgt gcc ttg gaa ccc agt ggc tgt act tca cta ccc agc    1374
Arg Ser Leu Cys Ala Leu Glu Pro Ser Gly Cys Thr Ser Leu Pro Ser
            395                 400                 405 aaa gcc tcc acg agg gca gct cgc ctt gga gag tac tta cta caa gac    1422
Lys Ala Ser Thr Arg Ala Ala Arg Leu Gly Glu Tyr Leu Leu Gln Asp
                410                 415                 420 ctg cag tca ggc cag tgt ctg cag cta tgg gac gat gac ttg gga gcg    1470
Leu Gln Ser Gly Gln Cys Leu Gln Leu Trp Asp Asp Asp Leu Gly Ala
425                 430                 435 cta tgg gcc tgc ccc atg gac aaa tac atc cac aag cgc tgg gcc ctc    1518
Leu Trp Ala Cys Pro Met Asp Lys Tyr Ile His Lys Arg Trp Ala Leu
440                 445                 450                 455 gtg tgg ctg gcc tgc cta ctc ttt gcc gct gcg ctt tcc ctc atc ctc    1566
Val Trp Leu Ala Cys Leu Leu Phe Ala Ala Ala Leu Ser Leu Ile Leu
                460                 465                 470 ctt ctc aaa aag gat cac gcg aaa gcg gcc gcc agg ggc cgc gcg gct    1614
Leu Leu Lys Lys Asp His Ala Lys Ala Ala Ala Arg Gly Arg Ala Ala
            475                 480                 485 ctg ctc ctc tac tca gcc gat gac tcg ggt ttc gag cgc ctg gtg ggc    1662
Leu Leu Leu Tyr Ser Ala Asp Asp Ser Gly Phe Glu Arg Leu Val Gly
                490                 495                 500 gcc ctg gcg tcg gcc ctg tgc cag ctg ccg ctg cgc gtg gcc gta gac    1710
Ala Leu Ala Ser Ala Leu Cys Gln Leu Pro Leu Arg Val Ala Val Asp
```

```
                505                 510                 515
ctg tgg agc cgt cgt gaa ctg agc gcg cag ggg ccc gtg gct tgg ttt       1758
Leu Trp Ser Arg Arg Glu Leu Ser Ala Gln Gly Pro Val Ala Trp Phe
520                 525                 530                 535 cac gcg cag cgg cgc cag acc ctg cag gag ggc ggc gtg gtg gtc ttg       1806
His Ala Gln Arg Arg Gln Thr Leu Gln Glu Gly Gly Val Val Val Leu
                540                 545                 550 ctc ttc tct ccc ggt gcg gtg gcg ctg tgc agc gag tgg cta cag gat       1854
Leu Phe Ser Pro Gly Ala Val Ala Leu Cys Ser Glu Trp Leu Gln Asp
            555                 560                 565 ggg gtg tcc ggg ccc ggg gcg cac ggc ccg cac gac gcc ttc cgc gcc       1902
Gly Val Ser Gly Pro Gly Ala His Gly Pro His Asp Ala Phe Arg Ala
570                 575                 580 tcg ctc agc tgc gtg ctg ccc gac ttc ttg cag ggc cgg gcg ccc ggc       1950
Ser Leu Ser Cys Val Leu Pro Asp Phe Leu Gln Gly Arg Ala Pro Gly
585                 590                 595 agc tac gtg ggg gcc tgc ttc gac agg ctg ctc cac ccg gac gcc gta       1998
Ser Tyr Val Gly Ala Cys Phe Asp Arg Leu Leu His Pro Asp Ala Val
600                 605                 610                 615 ccc gcc ctt ttc cgc acc gtg ccc gtc ttc aca ctg ccc tcc caa ctg       2046
Pro Ala Leu Phe Arg Thr Val Pro Val Phe Thr Leu Pro Ser Gln Leu
                620                 625                 630 cca gac ttc ctg ggg gcc ctg cag cag cct cgc gcc ccg cgt tcc ggg       2094
Pro Asp Phe Leu Gly Ala Leu Gln Gln Pro Arg Ala Pro Arg Ser Gly
            635                 640                 645 cgg ctc caa gag aga gcg gag caa gtg tcc cgg gcc ctt cag cca gcc       2142
Arg Leu Gln Glu Arg Ala Glu Gln Val Ser Arg Ala Leu Gln Pro Ala
650                 655                 660 ctg gat agc tac ttc cat ccc ccg ggg act ccc gcg ccg gga cgc ggg       2190
Leu Asp Ser Tyr Phe His Pro Pro Gly Thr Pro Ala Pro Gly Arg Gly
665                 670                 675 gtg gga cca ggg gcg gga cct ggg gcg ggg gac ggg act taaataaagg       2239
Val Gly Pro Gly Ala Gly Pro Gly Ala Gly Asp Gly Thr
680                 685                 690 cagacgctgt tttct                                                      2255

<210> SEQ ID NO 2
<211> LENGTH: 692
<212> TYPE: PRT
<213> ORGANISM: Homo sapiens

<400> SEQUENCE: 2

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125
```

```
Phe Gln Ala Tyr Pro Thr Ala Arg Cys Val Leu Leu Glu Val Gln Val
            130                 135                 140
Pro Ala Ala Leu Val Gln Phe Gly Gln Ser Val Gly Ser Val Val Tyr
145                 150                 155                 160
Asp Cys Phe Glu Ala Ala Leu Gly Ser Glu Val Arg Ile Trp Ser Tyr
                165                 170                 175
Thr Gln Pro Arg Tyr Glu Lys Glu Leu Asn His Thr Gln Gln Leu Pro
            180                 185                 190
Ala Leu Pro Trp Leu Asn Val Ser Ala Asp Gly Asp Asn Val His Leu
        195                 200                 205
Val Leu Asn Val Ser Glu Glu Gln His Phe Gly Leu Ser Leu Tyr Trp
    210                 215                 220
Asn Gln Val Gln Gly Pro Pro Lys Pro Arg Trp His Lys Asn Leu Thr
225                 230                 235                 240
Gly Pro Gln Ile Ile Thr Leu Asn His Thr Asp Leu Val Pro Cys Leu
                245                 250                 255
Cys Ile Gln Val Trp Pro Leu Glu Pro Asp Ser Val Arg Thr Asn Ile
            260                 265                 270
Cys Pro Phe Arg Glu Asp Pro Arg Ala His Gln Asn Leu Trp Gln Ala
        275                 280                 285
Ala Arg Leu Arg Leu Leu Thr Leu Gln Ser Trp Leu Leu Asp Ala Pro
    290                 295                 300
Cys Ser Leu Pro Ala Glu Ala Ala Leu Cys Trp Arg Ala Pro Gly Gly
305                 310                 315                 320
Asp Pro Cys Gln Pro Leu Val Pro Pro Leu Ser Trp Glu Asn Val Thr
                325                 330                 335
Val Asp Lys Val Leu Glu Phe Pro Leu Leu Lys Gly His Pro Asn Leu
            340                 345                 350
Cys Val Gln Val Asn Ser Ser Glu Lys Leu Gln Leu Gln Glu Cys Leu
        355                 360                 365
Trp Ala Asp Ser Leu Gly Pro Leu Lys Asp Asp Val Leu Leu Leu Glu
    370                 375                 380
Thr Arg Gly Pro Gln Asp Asn Arg Ser Leu Cys Ala Leu Glu Pro Ser
385                 390                 395                 400
Gly Cys Thr Ser Leu Pro Ser Lys Ala Ser Thr Arg Ala Ala Arg Leu
                405                 410                 415
Gly Glu Tyr Leu Leu Gln Asp Leu Gln Ser Gly Gln Cys Leu Gln Leu
            420                 425                 430
Trp Asp Asp Asp Leu Gly Ala Leu Trp Ala Cys Pro Met Asp Lys Tyr
        435                 440                 445
Ile His Lys Arg Trp Ala Leu Val Trp Leu Ala Cys Leu Leu Phe Ala
    450                 455                 460
Ala Ala Leu Ser Leu Ile Leu Leu Leu Lys Lys Asp His Ala Lys Ala
465                 470                 475                 480
Ala Ala Arg Gly Arg Ala Ala Leu Leu Leu Tyr Ser Ala Asp Asp Ser
                485                 490                 495
Gly Phe Glu Arg Leu Val Gly Ala Leu Ala Ser Ala Leu Cys Gln Leu
            500                 505                 510
Pro Leu Arg Val Ala Val Asp Leu Trp Ser Arg Arg Glu Leu Ser Ala
        515                 520                 525
Gln Gly Pro Val Ala Trp Phe His Ala Gln Arg Arg Gln Thr Leu Gln
    530                 535                 540
Glu Gly Gly Val Val Val Leu Leu Phe Ser Pro Gly Ala Val Ala Leu
545                 550                 555                 560
```

Cys Ser Glu Trp Leu Gln Asp Gly Val Ser Gly Pro Gly Ala His Gly
            565                 570                 575

Pro His Asp Ala Phe Arg Ala Ser Leu Ser Cys Val Leu Pro Asp Phe
            580                 585                 590

Leu Gln Gly Arg Ala Pro Gly Ser Tyr Val Gly Ala Cys Phe Asp Arg
            595                 600                 605

Leu Leu His Pro Asp Ala Val Pro Ala Leu Phe Arg Thr Val Pro Val
            610                 615                 620

Phe Thr Leu Pro Ser Gln Leu Pro Asp Phe Leu Gly Ala Leu Gln Gln
625                 630                 635                 640

Pro Arg Ala Pro Arg Ser Gly Arg Leu Gln Glu Arg Ala Glu Gln Val
            645                 650                 655

Ser Arg Ala Leu Gln Pro Ala Leu Asp Ser Tyr Phe His Pro Pro Gly
            660                 665                 670

Thr Pro Ala Pro Gly Arg Gly Val Gly Pro Gly Ala Gly Pro Gly Ala
            675                 680                 685

Gly Asp Gly Thr
            690

<210> SEQ ID NO 3
<211> LENGTH: 432
<212> TYPE: PRT
<213> ORGANISM: Homo sapiens

<400> SEQUENCE: 3

Leu Glu Arg Leu Val Gly Pro Gln Asp Ala Thr His Cys Ser Pro Gly
1               5                   10                  15

Leu Ser Cys Arg Leu Trp Asp Ser Asp Ile Leu Cys Leu Pro Gly Asp
            20                  25                  30

Ile Val Pro Ala Pro Gly Pro Val Leu Ala Pro Thr His Leu Gln Thr
            35                  40                  45

Glu Leu Val Leu Arg Cys Gln Lys Glu Thr Asp Cys Asp Leu Cys Leu
50                  55                  60

Arg Val Ala Val His Leu Ala Val His Gly His Trp Glu Glu Pro Glu
65                  70                  75                  80

Asp Glu Glu Lys Phe Gly Gly Ala Ala Asp Ser Gly Val Glu Glu Pro
            85                  90                  95

Arg Asn Ala Ser Leu Gln Ala Gln Val Val Leu Ser Phe Gln Ala Tyr
            100                 105                 110

Pro Thr Ala Arg Cys Val Leu Leu Glu Val Gln Val Pro Ala Ala Leu
            115                 120                 125

Val Gln Phe Gly Gln Ser Val Gly Ser Val Val Tyr Asp Cys Phe Glu
            130                 135                 140

Ala Ala Leu Gly Ser Glu Val Arg Ile Trp Ser Tyr Thr Gln Pro Arg
145                 150                 155                 160

Tyr Glu Lys Glu Leu Asn His Thr Gln Gln Leu Pro Ala Leu Pro Trp
            165                 170                 175

Leu Asn Val Ser Ala Asp Gly Asp Asn Val His Leu Val Leu Asn Val
            180                 185                 190

Ser Glu Glu Gln His Phe Gly Leu Ser Leu Tyr Trp Asn Gln Val Gln
            195                 200                 205

Gly Pro Pro Lys Pro Arg Trp His Lys Asn Leu Thr Gly Pro Gln Ile
            210                 215                 220

Ile Thr Leu Asn His Thr Asp Leu Val Pro Cys Leu Cys Ile Gln Val
225                 230                 235                 240

```
Trp Pro Leu Glu Pro Asp Ser Val Arg Thr Asn Ile Cys Pro Phe Arg
            245                 250                 255

Glu Asp Pro Arg Ala His Gln Asn Leu Trp Gln Ala Ala Arg Leu Arg
        260                 265                 270

Leu Leu Thr Leu Gln Ser Trp Leu Leu Asp Ala Pro Cys Ser Leu Pro
            275                 280                 285

Ala Glu Ala Ala Leu Cys Trp Arg Ala Pro Gly Gly Asp Pro Cys Gln
290                 295                 300

Pro Leu Val Pro Pro Leu Ser Trp Glu Asn Val Thr Val Asp Lys Val
305                 310                 315                 320

Leu Glu Phe Pro Leu Leu Lys Gly His Pro Asn Leu Cys Val Gln Val
            325                 330                 335

Asn Ser Ser Glu Lys Leu Gln Leu Gln Glu Cys Leu Trp Ala Asp Ser
        340                 345                 350

Leu Gly Pro Leu Lys Asp Asp Val Leu Leu Leu Glu Thr Arg Gly Pro
    355                 360                 365

Gln Asp Asn Arg Ser Leu Cys Ala Leu Glu Pro Ser Gly Cys Thr Ser
370                 375                 380

Leu Pro Ser Lys Ala Ser Thr Arg Ala Ala Arg Leu Gly Glu Tyr Leu
385                 390                 395                 400

Leu Gln Asp Leu Gln Ser Gly Gln Cys Leu Gln Leu Trp Asp Asp Asp
            405                 410                 415

Leu Gly Ala Leu Trp Ala Cys Pro Met Asp Lys Tyr Ile His Lys Arg
        420                 425                 430

<210> SEQ ID NO 4
<211> LENGTH: 1753
<212> TYPE: DNA
<213> ORGANISM: Homo sapiens
<220> FEATURE:
<221> NAME/KEY: CDS
<222> LOCATION: (2)...(1726)

<400> SEQUENCE: 4 g gag gag cct agg aat gcc tct ctc cag gcc caa gtc gtg ctc tcc ttc      49
  Glu Glu Pro Arg Asn Ala Ser Leu Gln Ala Gln Val Val Leu Ser Phe
  1               5                   10                  15 cag gcc tac cct act gcc cgc tgc gtc ctg ctg gag gtg caa gtg cct       97
Gln Ala Tyr Pro Thr Ala Arg Cys Val Leu Leu Glu Val Gln Val Pro
                20                  25                  30 gct gcc ctt gtg cag ttt ggt cag tct gtg ggc tct gtg gta tat gac      145
Ala Ala Leu Val Gln Phe Gly Gln Ser Val Gly Ser Val Val Tyr Asp
            35                  40                  45 tgc ttc gag gct gcc cta ggg agt gag gta cga atc tgg tcc tat act      193
Cys Phe Glu Ala Ala Leu Gly Ser Glu Val Arg Ile Trp Ser Tyr Thr
    50                  55                  60 cag ccc agg tac gag aag gaa ctc aac cac aca cag cag ctg cct gcc      241
Gln Pro Arg Tyr Glu Lys Glu Leu Asn His Thr Gln Gln Leu Pro Ala
65                  70                  75                  80 ctg ccc tgg ctc aac gtg tca gca gat ggt gac aac gtg cat ctg gtt      289
Leu Pro Trp Leu Asn Val Ser Ala Asp Gly Asp Asn Val His Leu Val
                85                  90                  95 ctg aat gtc tct gag gag cag cac ttc ggc ctc tcc ctg tac tgg aat      337
Leu Asn Val Ser Glu Glu Gln His Phe Gly Leu Ser Leu Tyr Trp Asn
                100                 105                 110 cag gtc cag ggc ccc cca aaa ccc cgg tgg cac aaa aac ctg act gga      385
Gln Val Gln Gly Pro Pro Lys Pro Arg Trp His Lys Asn Leu Thr Gly
            115                 120                 125
```

-continued

```
ccg cag atc att acc ttg aac cac aca gac ctg gtt ccc tgc ctc tgt     433
Pro Gln Ile Ile Thr Leu Asn His Thr Asp Leu Val Pro Cys Leu Cys
    130             135             140 att cag gtg tgg cct ctg gaa cct gac tcc gtt agg acg aac atc tgc     481
Ile Gln Val Trp Pro Leu Glu Pro Asp Ser Val Arg Thr Asn Ile Cys
145             150             155             160 ccc ttc agg gag gac ccc cgc gca cac cag aac ctc tgg caa gcc gcc     529
Pro Phe Arg Glu Asp Pro Arg Ala His Gln Asn Leu Trp Gln Ala Ala
                165             170             175 cga ctg cga ctg ctg acc ctg cag agc tgg ctg ctg gac gca ccg tgc     577
Arg Leu Arg Leu Leu Thr Leu Gln Ser Trp Leu Leu Asp Ala Pro Cys
        180             185             190 tcg ctg ccc gca gaa gcg gca ctg tgc tgg cgg gct ccg ggt ggg gac     625
Ser Leu Pro Ala Glu Ala Ala Leu Cys Trp Arg Ala Pro Gly Gly Asp
            195             200             205 ccc tgc cag cca ctg gtc cca ccg ctt tcc tgg gag aac gtc act gtg     673
Pro Cys Gln Pro Leu Val Pro Pro Leu Ser Trp Glu Asn Val Thr Val
    210             215             220 gac gtg aac agc tcg gag aag ctg cag ctg cag gag tgc ttg tgg gct     721
Asp Val Asn Ser Ser Glu Lys Leu Gln Leu Gln Glu Cys Leu Trp Ala
225             230             235             240 gac tcc ctg ggg cct ctc aaa gac gat gtg cta ctg ttg gag aca cga     769
Asp Ser Leu Gly Pro Leu Lys Asp Asp Val Leu Leu Leu Glu Thr Arg
                245             250             255 ggc ccc cag gac aac aga tcc ctc tgt gcc ttg gaa ccc agt ggc tgt     817
Gly Pro Gln Asp Asn Arg Ser Leu Cys Ala Leu Glu Pro Ser Gly Cys
        260             265             270 act tca cta ccc agc aaa gcc tcc acg agg gca gct cgc ctt gga gag     865
Thr Ser Leu Pro Ser Lys Ala Ser Thr Arg Ala Ala Arg Leu Gly Glu
            275             280             285 tac tta cta caa gac ctg cag tca ggc cag tgt ctg cag cta tgg gac     913
Tyr Leu Leu Gln Asp Leu Gln Ser Gly Gln Cys Leu Gln Leu Trp Asp
    290             295             300 gat gac ttg gga gcg cta tgg gcc tgc ccc atg gac aaa tac atc cac     961
Asp Asp Leu Gly Ala Leu Trp Ala Cys Pro Met Asp Lys Tyr Ile His
305             310             315             320 aag cgc tgg gcc ctc gtg tgg ctg gcc tgc cta atc ttt gcc gct gcg    1009
Lys Arg Trp Ala Leu Val Trp Leu Ala Cys Leu Ile Phe Ala Ala Ala
                325             330             335 ctt tcc ctc atc ctc ctt ctc aaa aag gat cac gcg aaa ggg tgg ctg    1057
Leu Ser Leu Ile Leu Leu Leu Lys Lys Asp His Ala Lys Gly Trp Leu
        340             345             350 agg ctc ttg aaa cag gac gtc cgc tcg ggg gcg gcc gcc agg ggc cgc    1105
Arg Leu Leu Lys Gln Asp Val Arg Ser Gly Ala Ala Ala Arg Gly Arg
            355             360             365 gcg gct ctg ctc ctc tac tca gcc gat gac tcg ggt ttc gag cgc ctg    1153
Ala Ala Leu Leu Leu Tyr Ser Ala Asp Asp Ser Gly Phe Glu Arg Leu
    370             375             380 gtg ggc gcc ctg gcg tcg gcc ctg tgc cag ctg ccg ctg cgc gtg gcc    1201
Val Gly Ala Leu Ala Ser Ala Leu Cys Gln Leu Pro Leu Arg Val Ala
385             390             395             400 gta gac ctg tgg agc cgt cgt gaa ctg agc gcg cag ggg ccc gtg gct    1249
Val Asp Leu Trp Ser Arg Arg Glu Leu Ser Ala Gln Gly Pro Val Ala
                405             410             415 tgg ttt cac gcg cag cgg cgc cag acc ctg cag gag ggc ggc gtg gtg    1297
Trp Phe His Ala Gln Arg Arg Gln Thr Leu Gln Glu Gly Gly Val Val
        420             425             430 gtc ttg ctc ttc tct ccc ggt gcg gtg gcg ctg tgc agc gag tgg cta    1345
Val Leu Leu Phe Ser Pro Gly Ala Val Ala Leu Cys Ser Glu Trp Leu
            435             440             445
```

```
cag gat ggg gtg tcc ggg ccc ggg gcg cac ggc ccg cac gac gcc ttc      1393
Gln Asp Gly Val Ser Gly Pro Gly Ala His Gly Pro His Asp Ala Phe
450                 455                 460 cgc gcc tcg ctc agc tgc gtg ctg ccc gac ttc ttg cag ggc cgg gcg      1441
Arg Ala Ser Leu Ser Cys Val Leu Pro Asp Phe Leu Gln Gly Arg Ala
465                 470                 475                 480 ccc ggc agc tac gtg ggg gcc tgc ttc gac agg ctg ctc cac ccg gac      1489
Pro Gly Ser Tyr Val Gly Ala Cys Phe Asp Arg Leu Leu His Pro Asp
            485                 490                 495 gcc gta ccc gcc ctt ttc cgc acc gtg ccc gtc ttc aca ctg ccc tcc      1537
Ala Val Pro Ala Leu Phe Arg Thr Val Pro Val Phe Thr Leu Pro Ser
500                 505                 510 caa ctg cca gac ttc ctg ggg gcc ctg cag cag cct cgc gcc ccg cgt      1585
Gln Leu Pro Asp Phe Leu Gly Ala Leu Gln Gln Pro Arg Ala Pro Arg
515                 520                 525 tcc ggg cgg ctc caa gag aga gcg gag caa gtg tcc cgg gcc ctt cag      1633
Ser Gly Arg Leu Gln Glu Arg Ala Glu Gln Val Ser Arg Ala Leu Gln
530                 535                 540 cca gcc ctg gat agc tac ttc cat ccc ccg ggg act ccc gcg ccg gga      1681
Pro Ala Leu Asp Ser Tyr Phe His Pro Pro Gly Thr Pro Ala Pro Gly
545                 550                 555                 560 cgc ggg gtg gga cca ggg gcg gga cct ggg gcg ggg gac ggg act          1726
Arg Gly Val Gly Pro Gly Ala Gly Pro Gly Ala Gly Asp Gly Thr
            565                 570                 575 taaataaagg cagacgctgt ttttcta                                         1753

<210> SEQ ID NO 5
<211> LENGTH: 575
<212> TYPE: PRT
<213> ORGANISM: Homo sapiens

<400> SEQUENCE: 5

Glu Glu Pro Arg Asn Ala Ser Leu Gln Ala Gln Val Val Leu Ser Phe
 1               5                  10                  15

Gln Ala Tyr Pro Thr Ala Arg Cys Val Leu Glu Val Gln Val Pro
            20                  25                  30

Ala Ala Leu Val Gln Phe Gly Gln Ser Val Gly Ser Val Val Tyr Asp
        35                  40                  45

Cys Phe Glu Ala Ala Leu Gly Ser Glu Val Arg Ile Trp Ser Tyr Thr
    50                  55                  60

Gln Pro Arg Tyr Glu Lys Glu Leu Asn His Thr Gln Gln Leu Pro Ala
65                  70                  75                  80

Leu Pro Trp Leu Asn Val Ser Ala Asp Gly Asp Asn Val His Leu Val
                85                  90                  95

Leu Asn Val Ser Glu Glu Gln His Phe Gly Leu Ser Leu Tyr Trp Asn
            100                 105                 110

Gln Val Gln Gly Pro Pro Lys Pro Arg Trp His Lys Asn Leu Thr Gly
        115                 120                 125

Pro Gln Ile Ile Thr Leu Asn His Thr Asp Leu Val Pro Cys Leu Cys
    130                 135                 140

Ile Gln Val Trp Pro Leu Glu Pro Asp Ser Val Arg Thr Asn Ile Cys
145                 150                 155                 160

Pro Phe Arg Glu Asp Pro Arg Ala His Gln Asn Leu Trp Gln Ala Ala
                165                 170                 175

Arg Leu Arg Leu Leu Thr Leu Gln Ser Trp Leu Leu Asp Ala Pro Cys
            180                 185                 190

Ser Leu Pro Ala Glu Ala Ala Leu Cys Trp Arg Ala Pro Gly Gly Asp
        195                 200                 205
```

Pro Cys Gln Pro Leu Val Pro Pro Leu Ser Trp Glu Asn Val Thr Val
                210                 215                 220

Asp Val Asn Ser Ser Glu Lys Leu Gln Leu Gln Glu Cys Leu Trp Ala
225                 230                 235                 240

Asp Ser Leu Gly Pro Leu Lys Asp Val Leu Leu Leu Glu Thr Arg
                245                 250                 255

Gly Pro Gln Asp Asn Arg Ser Leu Cys Ala Leu Glu Pro Ser Gly Cys
                260                 265                 270

Thr Ser Leu Pro Ser Lys Ala Ser Thr Arg Ala Ala Arg Leu Gly Glu
                275                 280                 285

Tyr Leu Leu Gln Asp Leu Gln Ser Gly Gln Cys Leu Gln Leu Trp Asp
                290                 295                 300

Asp Asp Leu Gly Ala Leu Trp Ala Cys Pro Met Asp Lys Tyr Ile His
305                 310                 315                 320

Lys Arg Trp Ala Leu Val Trp Leu Ala Cys Leu Leu Phe Ala Ala Ala
                325                 330                 335

Leu Ser Leu Ile Leu Leu Leu Lys Lys Asp His Ala Lys Gly Trp Leu
                340                 345                 350

Arg Leu Leu Lys Gln Asp Val Arg Ser Gly Ala Ala Ala Arg Gly Arg
                355                 360                 365

Ala Ala Leu Leu Leu Tyr Ser Ala Asp Asp Ser Gly Phe Glu Arg Leu
370                 375                 380

Val Gly Ala Leu Ala Ser Ala Leu Cys Gln Leu Pro Leu Arg Val Ala
385                 390                 395                 400

Val Asp Leu Trp Ser Arg Arg Glu Leu Ser Ala Gln Gly Pro Val Ala
                405                 410                 415

Trp Phe His Ala Gln Arg Arg Gln Thr Leu Gln Glu Gly Gly Val Val
                420                 425                 430

Val Leu Leu Phe Ser Pro Gly Ala Val Ala Leu Cys Ser Glu Trp Leu
                435                 440                 445

Gln Asp Gly Val Ser Gly Pro Gly Ala His Gly Pro His Asp Ala Phe
450                 455                 460

Arg Ala Ser Leu Ser Cys Val Leu Pro Asp Phe Leu Gln Gly Arg Ala
465                 470                 475                 480

Pro Gly Ser Tyr Val Gly Ala Cys Phe Asp Arg Leu Leu His Pro Asp
                485                 490                 495

Ala Val Pro Ala Leu Phe Arg Thr Val Pro Val Phe Thr Leu Pro Ser
                500                 505                 510

Gln Leu Pro Asp Phe Leu Gly Ala Leu Gln Gln Pro Arg Ala Pro Arg
                515                 520                 525

Ser Gly Arg Leu Gln Glu Arg Ala Glu Gln Val Ser Arg Ala Leu Gln
                530                 535                 540

Pro Ala Leu Asp Ser Tyr Phe His Pro Pro Gly Thr Pro Ala Pro Gly
545                 550                 555                 560

Arg Gly Val Gly Pro Gly Ala Gly Pro Gly Ala Gly Asp Gly Thr
                565                 570                 575

<210> SEQ ID NO 6
<211> LENGTH: 1725
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(1725)

<223> OTHER INFORMATION: n = A,T,C or G

<400> SEQUENCE: 6
gargarccnm gnaaygcnws nytncargcn cargtngtny tnwsnttyca rgcntayccn 60
acngcnmgnt gygtnytnyt ngargtncar gtnccngcng cnytngtnca rttyggncar 120
wsngtnggnw sngtngtnta ygaytgytty gargcngcny tnggnwsnga rgtnmgnath 180
tggwsntaya cncarccnmg ntaygaraar garytnaayc ayacncarca rytnccngcn 240
ytnccntggy tnaaygtnws ngcngayggn gayaaygtnc ayytngtnyt naaygtnwsn 300
gargarcarc ayttyggnyt nwsnytntay tggaaycarg tncarggncc nccnaarccn 360
mgntggcaya araayytnac nggnccncar athathacny tnaaycayac ngayytngtn 420
ccntgyytnt gyathcargt ntggccnytn garccngayw sngtnmgnac naayathtgy 480
ccnttymgng argayccnmg ngcncaycar aayytntggc argcngcnmg nytnmgnytn 540
ytnacnytnc arwsntggyt nytngaygcn ccntgywsny tnccngcnga rgcngcnytn 600
tgytggmgng cnccnggngg ngayccntgy carccnytng tnccnccnyt nwsntgggar 660
aaygtnacng tngaygtnaa ywsnwsngar aarytncary tncargartg yytntgggcn 720
gaywsnytng gnccnytnaa rgaygaygtn ytnytnytng aracnmgngg nccncargay 780
aaymgnwsny tntgygcnyt ngarccnwsn ggntgyacnw snytnccnws naargcnwsn 840
acnmgngcng cnmgnytngg ngartayytn ytncargayy tncarwsngg ncartgyytn 900
carytntggg aygaygayyt nggngcnytn tgggcntgyc cnatggayaa rtayathcay 960
aarmgntggg cnytngtntg gytngcntgy ytnytnttyg cngcngcnyt nwsnytnath 1020
ytnytnytna araargayca ygcnaarggn tggytnmgny tnytnaarca rgaygtnmgn 1080
wsnggngcng cngcnmgngg nmgngcngcn ytnytnytnt aywsngcnga ygaywsnggn 1140
ttygarmgny tngtnggngc nytngcnwsn gcnytntgyc arytnccnyt nmgngtngcn 1200
gtngayytnt ggwsnmgnmg ngarytnwsn gcncarggnc cngtngcntg gttycaygcn 1260
carmgnmgnc aracnytnca rgarggnggn gtngtngtny tnytnttyws nccnggngcn 1320
gtngcnytnt gywsngartg gytncargay ggngtnwsng gnccnggngc ncayggnccn 1380
caygaygcnt tymgngcnws nytnwsntgy gtnytnccng ayttyytnca rggnmgngcn 1440
ccnggnwsnt aygtnggngc ntgyttygay mgnytnytnc ayccngaygc ngtnccngcn 1500
ytnttymgna cngtnccngt nttyacnytn ccnwsncary tnccngaytt yytnggngcn 1560
ytncarcarc cnmgngcncc nmgnwsnggn mgnytncarg armgngcnga rcargtnwsn 1620
mgngcnytnc arccngcnyt ngaywsntay ttycayccnc cnggnacncc ngcnccnggn 1680
mgnggngtng gnccnggngc nggnccnggn gcnggngayg gnacn 1725

<210> SEQ ID NO 7
<211> LENGTH: 2076
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(2076)
<223> OTHER INFORMATION: n = A,T,C or G

<400> SEQUENCE: 7
atgccngtnc cntggttyyt nytnwsnytn gcnytnggnm gnwsnccngt ngtnytnwsn 60
ytngarmgny tngtnggncc ncargaygcn acncaytgyw snccnggnyt nwsntgymgn 120

-continued

```
ytntgggayw sngayathyt ntgyytnccn ggngayathg tnccngcncc nggnccngtn    180
ytngcnccna cncayytnca racngarytn gtnytnmgnt gycaraarga racngaytgy    240
gayytntgyy tnmgngtngc ngtncayytn gcngtncayg gncaytggga rgarccngar    300
gaygargara arttyggngg ngcngcngay wsnggngtng argarccnmg naaygcnwsn    360
ytncargcnc argtngtnyt nwsnttycar gcntayccna cngcnmgntg ygtnytnytn    420
gargtncarg tnccngcngc nytngtncar ttyggncarw sngtnggnws ngtngtntay    480
gaytgyttyg argcngcnyt nggnwsngar gtnmgnatht ggwsntayac ncarccnmgn    540
taygaraarg arytnaayca yacncarcar ytnccngcny tnccntggyt naaygtnwsn    600
gcngayggng ayaaygtnca yytngtnytn aaygtnwsng argarcarca yttyggnytn    660
wsnytntayt ggaaycargt ncarggnccn ccnaarccnm gntggcayaa raayytnacn    720
ggnccncara thathacnyt naaycayacn gayytngtnc cntgyytntg yathcargtn    780
tggccnytng arccngayws ngtnmgnacn aayathtgyc cnttymgnga rgayccnmgn    840
gcncaycara ayytntggca rgcngcnmgn ytnmgnytny tnacnytnca rwsntggytn    900
ytngaygcnc cntgywsnyt nccngcngar gcngcnytnt gytggmgngc nccnggnggn    960
gayccntgyc arccnytngt nccnccnytn wsntgggara aygtnacngt ngayaargtn   1020
ytngarttyc cnytnytnaa rggncayccn aayytntgyg tncargtnaa ywsnwsngar   1080
aarytncary tncargartg yytntgggcn gaywsnytng gnccnytnaa rgaygaygtn   1140
ytnytnytng aracnmgngg nccncargay aaymgnwsny tntgygcnyt ngarccnwsn   1200
ggntgyacnw snytnccnws naargcnwsn acnmgngcng cnmgnytngg ngartayytn   1260
ytncargayy tncarwsngg ncartgyytn carytntggg aygaygayyt nggngcnytn   1320
tgggcntgyc cnatggayaa rtayathcay aarmgntggg cnytngtntg gytngcntgy   1380
ytnytnttyg cngcngcnyt nwsnytnath ytnytnytna araargayca ygcnaargcn   1440
gcngcnmgng gnmgngcngc nytnytnytn taywsngcng aygaywsngg nttygarmgn   1500
ytngtnggng cnytngcnws ngcnytntgy carytnccny tnmgngtngc ngtngayytn   1560
tggwsnmgnm gngarytnws ngcncarggn ccngtngcnt ggttycaygc ncarmgnmgn   1620
caracnytnc argarggngg ngtngtngtn ytnytnttyw snccnggngc ngtngcnytn   1680
tgywsngart ggytncarga yggngtnwsn ggnccnggng cncayggncc ncaygaygcn   1740
ttymgngcnw snytnwsntg ygtnytnccn gayttyytnc arggnmgngc nccnggnwsn   1800
taygtnggng cntgyttyga ymgnytnytn cayccngayg cngtnccngc nytnttymgn   1860
acngtnccng tnttyacnyt nccnwsncar ytnccngayt tyytnggngc nytncarcar   1920
ccnmgngcnc cnmgnwsngg nmgnytncar garmgngcng arcargtnws nmgngcnytn   1980
carccngcny tngaywsnta yttycayccn ccnggnacnc cngcnccngg nmgnggngtn   2040
ggnccnggng cnggnccngg ngcnggngay ggnacn                              2076
```

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8

```
cggcgtggtg gtcttgctct t                                               21
```

<210> SEQ ID NO 9

-continued

```
<211> LENGTH: 16
<212> TYPE: PRT
<213> ORGANISM: Artificial Sequence
<220> FEATURE:
<223> OTHER INFORMATION: peptide linker

<400> SEQUENCE: 9

Gly Gly Ser Gly Gly Ser Gly Gly Gly Ser Gly Gly Gly Gly Ser
 1               5                  10                  15

<210> SEQ ID NO 10
<211> LENGTH: 688
<212> TYPE: PRT
<213> ORGANISM: Artificial Sequence
<220> FEATURE:
<223> OTHER INFORMATION: Chimeric Zcytor14 protein

<400> SEQUENCE: 10

Met Pro Val Pro Trp Phe Leu Ser Leu Ala Leu Gly Arg Ser Pro
 1               5                  10                  15

Val Val Leu Ser Leu Glu Arg Leu Val Gly Pro Gln Asp Ala Thr His
                20                  25                  30

Cys Ser Pro Gly Leu Ser Cys Arg Leu Trp Asp Ser Asp Ile Leu Cys
            35                  40                  45

Leu Pro Gly Asp Ile Val Pro Ala Pro Gly Pro Val Leu Ala Pro Thr
        50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
        195                 200                 205

Val Leu Asn Val Ser Glu Glu Gln His Phe Gly Leu Ser Leu Tyr Trp
    210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
        275                 280                 285

Ala Arg Leu Arg Leu Leu Thr Leu Gln Ser Trp Leu Leu Asp Ala Pro
    290                 295                 300

Cys Ser Leu Pro Ala Glu Ala Ala Leu Cys Trp Arg Ala Pro Gly Gly
305                 310                 315                 320
```

```
Asp Pro Cys Gln Pro Leu Val Pro Pro Leu Ser Trp Glu Asn Val Thr
            325                 330                 335

Val Asp Val Asn Ser Ser Glu Lys Leu Gln Leu Gln Glu Cys Leu Trp
            340                 345                 350

Ala Asp Ser Leu Gly Pro Leu Lys Asp Val Leu Leu Leu Glu Thr
            355                 360                 365

Arg Gly Pro Gln Asp Asn Arg Ser Leu Cys Ala Leu Glu Pro Ser Gly
            370                 375                 380

Cys Thr Ser Leu Pro Ser Lys Ala Ser Thr Arg Ala Ala Arg Leu Gly
385                 390                 395                 400

Glu Tyr Leu Leu Gln Asp Leu Gln Ser Gly Gln Cys Leu Gln Leu Trp
                405                 410                 415

Asp Asp Asp Leu Gly Ala Leu Trp Ala Cys Pro Met Asp Lys Tyr Ile
            420                 425                 430

His Lys Arg Trp Ala Leu Val Trp Leu Ala Cys Leu Leu Phe Ala Ala
            435                 440                 445

Ala Leu Ser Leu Ile Leu Leu Lys Lys Asp His Ala Lys Gly Trp
            450                 455                 460

Leu Arg Leu Leu Lys Gln Asp Val Arg Ser Gly Ala Ala Ala Arg Gly
465                 470                 475                 480

Arg Ala Ala Leu Leu Tyr Ser Ala Asp Asp Ser Gly Phe Glu Arg
                485                 490                 495

Leu Val Gly Ala Leu Ala Ser Ala Leu Cys Gln Leu Pro Leu Arg Val
            500                 505                 510

Ala Val Asp Leu Trp Ser Arg Arg Glu Leu Ser Ala Gln Gly Pro Val
            515                 520                 525

Ala Trp Phe His Ala Gln Arg Arg Gln Thr Leu Gln Glu Gly Gly Val
            530                 535                 540

Val Val Leu Leu Phe Ser Pro Gly Ala Val Ala Leu Cys Ser Glu Trp
545                 550                 555                 560

Leu Gln Asp Gly Val Ser Gly Pro Gly Ala His Gly Pro His Asp Ala
                565                 570                 575

Phe Arg Ala Ser Leu Ser Cys Val Leu Pro Asp Phe Leu Gln Gly Arg
            580                 585                 590

Ala Pro Gly Ser Tyr Val Gly Ala Cys Phe Asp Arg Leu Leu His Pro
            595                 600                 605

Asp Ala Val Pro Ala Leu Phe Arg Thr Val Pro Val Phe Thr Leu Pro
610                 615                 620

Ser Gln Leu Pro Asp Phe Leu Gly Ala Leu Gln Gln Pro Arg Ala Pro
625                 630                 635                 640

Arg Ser Gly Arg Leu Gln Glu Arg Ala Glu Gln Val Ser Arg Ala Leu
                645                 650                 655

Gln Pro Ala Leu Asp Ser Tyr Phe His Pro Pro Gly Thr Pro Ala Pro
            660                 665                 670

Gly Arg Gly Val Gly Pro Gly Ala Gly Pro Gly Ala Gly Asp Gly Thr
            675                 680                 685

<210> SEQ ID NO 11
<211> LENGTH: 705
<212> TYPE: PRT
<213> ORGANISM: Artificial Sequence
<220> FEATURE:
<223> OTHER INFORMATION: Chimeric Zcytor14 protein

<400> SEQUENCE: 11
```

-continued

```
Met Pro Val Pro Trp Phe Leu Leu Ser Leu Ala Leu Gly Arg Ser Pro
 1               5                  10                 15
Val Val Leu Ser Leu Glu Arg Leu Val Gly Pro Gln Asp Ala Thr His
             20                 25                 30
Cys Ser Pro Gly Leu Ser Cys Arg Leu Trp Asp Ser Asp Ile Leu Cys
             35                 40                 45
Leu Pro Gly Asp Ile Val Pro Ala Pro Gly Pro Val Leu Ala Pro Thr
 50                 55                 60
His Leu Gln Thr Glu Leu Val Leu Arg Cys Gln Lys Glu Thr Asp Cys
 65              70                 75                 80
Asp Leu Cys Leu Arg Val Ala Val His Leu Ala Val His Gly His Trp
             85                 90                 95
Glu Glu Pro Glu Asp Glu Glu Lys Phe Gly Ala Ala Asp Ser Gly
                100                105                110
Val Glu Glu Pro Arg Asn Ala Ser Leu Gln Ala Gln Val Val Leu Ser
             115                120                125
Phe Gln Ala Tyr Pro Thr Ala Arg Cys Val Leu Glu Val Gln Val
        130                135                140
Pro Ala Ala Leu Val Gln Phe Gly Gln Ser Val Gly Ser Val Val Tyr
145                150                155                160
Asp Cys Phe Glu Ala Ala Leu Gly Ser Glu Val Arg Ile Trp Ser Tyr
                165                170                175
Thr Gln Pro Arg Tyr Glu Lys Glu Leu Asn His Thr Gln Gln Leu Pro
             180                185                190
Ala Leu Pro Trp Leu Asn Val Ser Ala Asp Gly Asp Asn Val His Leu
             195                200                205
Val Leu Asn Val Ser Glu Glu Gln His Phe Gly Leu Ser Leu Tyr Trp
210                215                220
Asn Gln Val Gln Gly Pro Pro Lys Pro Arg Trp His Lys Asn Leu Thr
225                230                235                240
Gly Pro Gln Ile Ile Thr Leu Asn His Thr Asp Leu Val Pro Cys Leu
                245                250                255
Cys Ile Gln Val Trp Pro Leu Glu Pro Asp Ser Val Arg Thr Asn Ile
                260                265                270
Cys Pro Phe Arg Glu Asp Pro Arg Ala His Gln Asn Leu Trp Gln Ala
             275                280                285
Ala Arg Leu Arg Leu Leu Thr Leu Gln Ser Trp Leu Leu Asp Ala Pro
             290                295                300
Cys Ser Leu Pro Ala Glu Ala Ala Leu Cys Trp Arg Ala Pro Gly Gly
305                310                315                320
Asp Pro Cys Gln Pro Leu Val Pro Pro Leu Ser Trp Glu Asn Val Thr
             325                330                335
Val Asp Lys Val Leu Glu Phe Pro Leu Leu Lys Gly His Pro Asn Leu
             340                345                350
Cys Val Gln Val Asn Ser Ser Glu Lys Leu Gln Leu Gln Glu Cys Leu
             355                360                365
Trp Ala Asp Ser Leu Gly Pro Leu Lys Asp Val Leu Leu Leu Glu
370                375                380
Thr Arg Gly Pro Gln Asp Asn Arg Ser Leu Cys Ala Leu Glu Pro Ser
385                390                395                400
Gly Cys Thr Ser Leu Pro Ser Lys Ala Ser Thr Arg Ala Ala Arg Leu
                405                410                415
Gly Glu Tyr Leu Leu Gln Asp Leu Gln Ser Gly Gln Cys Leu Gln Leu
             420                425                430
```

```
Trp Asp Asp Asp Leu Gly Ala Leu Trp Ala Cys Pro Met Asp Lys Tyr
            435                 440                 445
Ile His Lys Arg Trp Ala Leu Val Trp Leu Ala Cys Leu Leu Phe Ala
        450                 455                 460
Ala Ala Leu Ser Leu Ile Leu Leu Lys Asp His Ala Lys Gly
465                 470                 475                 480
Trp Leu Arg Leu Leu Lys Gln Asp Val Arg Ser Gly Ala Ala Arg
                485                 490                 495
Gly Arg Ala Ala Leu Leu Leu Tyr Ser Ala Asp Asp Ser Gly Phe Glu
                500                 505                 510
Arg Leu Val Gly Ala Leu Ala Ser Ala Leu Cys Gln Leu Pro Leu Arg
            515                 520                 525
Val Ala Val Asp Leu Trp Ser Arg Arg Glu Leu Ser Ala Gln Gly Pro
            530                 535                 540
Val Ala Trp Phe His Ala Gln Arg Arg Gln Thr Leu Gln Glu Gly Gly
545                 550                 555                 560
Val Val Val Leu Leu Phe Ser Pro Gly Ala Val Ala Leu Cys Ser Glu
                565                 570                 575
Trp Leu Gln Asp Gly Val Ser Gly Pro Gly Ala His Gly Pro His Asp
                580                 585                 590
Ala Phe Arg Ala Ser Leu Ser Cys Val Leu Pro Asp Phe Leu Gln Gly
            595                 600                 605
Arg Ala Pro Gly Ser Tyr Val Gly Ala Cys Phe Asp Arg Leu Leu His
            610                 615                 620
Pro Asp Ala Val Pro Ala Leu Phe Arg Thr Val Pro Val Phe Thr Leu
625                 630                 635                 640
Pro Ser Gln Leu Pro Asp Phe Leu Gly Ala Leu Gln Gln Pro Arg Ala
                645                 650                 655
Pro Arg Ser Gly Arg Leu Gln Glu Arg Ala Glu Gln Val Ser Arg Ala
                660                 665                 670
Leu Gln Pro Ala Leu Asp Ser Tyr Phe His Pro Pro Gly Thr Pro Ala
            675                 680                 685
Pro Gly Arg Gly Val Gly Pro Gly Ala Gly Pro Ala Gly Asp Gly
            690                 695                 700
Thr
705

<210> SEQ ID NO 12
<211> LENGTH: 675
<212> TYPE: PRT
<213> ORGANISM: Artificial Sequence
<220> FEATURE:
<223> OTHER INFORMATION: Chimeric Zcytor14 protein

<400> SEQUENCE: 12

Met Pro Val Pro Trp Phe Leu Leu Ser Leu Ala Leu Gly Arg Ser Pro
1               5                   10                  15
Val Val Leu Ser Leu Glu Arg Leu Val Gly Pro Gln Asp Ala Thr His
            20                  25                  30
Cys Ser Pro Gly Leu Ser Cys Arg Leu Trp Asp Ser Asp Ile Leu Cys
        35                  40                  45
Leu Pro Gly Asp Ile Val Pro Ala Pro Gly Pro Val Leu Ala Pro Thr
    50                  55                  60
His Leu Gln Thr Glu Leu Val Leu Arg Cys Gln Lys Glu Thr Asp Cys
65                  70                  75                  80
```

```
Asp Leu Cys Leu Arg Val Ala Val His Leu Ala Val His Gly His Trp
                85                  90                  95

Glu Glu Pro Glu Asp Glu Lys Phe Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
        195                 200                 205

Val Leu Asn Val Ser Glu Glu Gln His Phe Gly Leu Ser Leu Tyr Trp
210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
        275                 280                 285

Ala Arg Leu Arg Leu Leu Thr Leu Gln Ser Trp Leu Leu Asp Ala Pro
290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Val Asn Ser Ser Glu Lys Leu Gln Leu Gln Glu Cys Leu Trp
            340                 345                 350

Ala Asp Ser Leu Gly Pro Leu Lys Asp Asp Val Leu Leu Leu Glu Thr
        355                 360                 365

Arg Gly Pro Gln Asp Asn Arg Ser Leu Cys Ala Leu Glu Pro Ser Gly
370                 375                 380

Cys Thr Ser Leu Pro Ser Lys Ala Ser Thr Arg Ala Ala Arg Leu Gly
385                 390                 395                 400

Glu Tyr Leu Leu Gln Asp Leu Gln Ser Gly Gln Cys Leu Gln Leu Trp
                405                 410                 415

Asp Asp Asp Leu Gly Ala Leu Trp Ala Cys Pro Met Asp Lys Tyr Ile
            420                 425                 430

His Lys Arg Trp Ala Leu Val Trp Leu Ala Cys Leu Leu Phe Ala Ala
        435                 440                 445

Ala Leu Ser Leu Ile Leu Leu Leu Lys Lys Asp His Ala Lys Ala Ala
        450                 455                 460

Ala Arg Gly Arg Ala Ala Leu Leu Leu Tyr Ser Ala Asp Asp Ser Gly
465                 470                 475                 480

Phe Glu Arg Leu Val Gly Ala Leu Ala Ser Ala Leu Cys Gln Leu Pro
                485                 490                 495

Leu Arg Val Ala Val Asp Leu Trp Ser Arg Arg Glu Leu Ser Ala Gln
            500                 505                 510
```

```
Gly Pro Val Ala Trp Phe His Ala Gln Arg Arg Gln Thr Leu Gln Glu
            515                 520                 525
Gly Gly Val Val Val Leu Leu Phe Ser Pro Gly Ala Val Ala Leu Cys
        530                 535                 540
Ser Glu Trp Leu Gln Asp Gly Val Ser Gly Pro Gly Ala His Gly Pro
545                 550                 555                 560
His Asp Ala Phe Arg Ala Ser Leu Ser Cys Val Leu Pro Asp Phe Leu
                565                 570                 575
Gln Gly Arg Ala Pro Gly Ser Tyr Val Gly Ala Cys Phe Asp Arg Leu
            580                 585                 590
Leu His Pro Asp Ala Val Pro Ala Leu Phe Arg Thr Val Pro Val Phe
        595                 600                 605
Thr Leu Pro Ser Gln Leu Pro Asp Phe Leu Gly Ala Leu Gln Gln Pro
    610                 615                 620
Arg Ala Pro Arg Ser Gly Arg Leu Gln Glu Arg Ala Glu Gln Val Ser
625                 630                 635                 640
Arg Ala Leu Gln Pro Ala Leu Asp Ser Tyr Phe His Pro Gly Thr
                645                 650                 655
Pro Ala Pro Gly Arg Gly Val Gly Pro Gly Ala Gly Pro Gly Ala Gly
            660                 665                 670
Asp Gly Thr
        675

<210> SEQ ID NO 13
<211> LENGTH: 1874
<212> TYPE: DNA
<213> ORGANISM: Homo sapiens

<400> SEQUENCE: 13
gaattccggc aggcacaaac tcatccatcc ccagttgatt ggaagaaaca acgatgactc      60
ctgggaagac ctcattggtg tcactgctac tgctgctgag cctggaggcc atagtgaagg     120
caggaatcac aatcccacga aatccaggat gcccaaattc tgaggacaag aacttccccc     180
ggactgtgat ggtcaacctg aacatccata accggaatac caataccaat cccaaaaggt     240
cctcagatta ctacaaccga tccacctcac cttggaatct ccaccgcaat gaggaccctg     300
agagatatcc ctctgtgatc tgggaggcaa agtgccgcca cttgggctgc atcaacgctg     360
atgggaacgt ggactaccac atgaactctg tccccatcca gcaagagatc ctggtcctgc     420
gcagggagcc tccacactgc cccaactcct tccggctgga agatactg tgtccgtgg      480
gctgcacctg tgtcaccccg attgtccacc atgtggccta agagctctgg ggagcccaca     540
ctccccaaag cagttagact atggagagcc gacccagccc tcaggaacc tcatccttc      600
aaagacagcc tcatttcgga ctaaactcat tagagttctt aaggcagttt gtccaattaa     660
agcttcagag gtaacacttg gccaagatat gagatctgaa ttacctttcc ctcttttccaa    720
gaaggaaggt ttgactgagt accaatttgc ttcttgttta cttttttaag ggctttaagt     780
tatttatgta tttaatatgc cctgagataa ctttggggta taagattcca ttttaatgaa     840
ttacctactt tattttgttt gtcttttttaa agaagataag attctgggct tgggaatttt    900
attatttaaa aggtaaaacc tgtatttatt tgagctatt aaggatctat ttatgtttaa     960
gtatttagaa aaaggtgaaa agcactatt atcagttctg cctaggtaaa tgtaagatag    1020
aattaaatgg cagtgcaaaa tttctgagtc tttacaacat acggatatag tatttcctcc    1080
tctttgtttt taaaagttat aacatggctg aaaagaaaga ttaaacctac tttcatatgt    1140
```

-continued

```
attaatttaa attttgcaat ttgttgaggt tttacaagag atacagcaag tctaactctc    1200
tgttccatta aacccttata ataaaatcct tctgtaataa taaagtttca aaagaaaatg    1260
tttatttgtt ctcattaaat gtattttagc aaactcagct cttccctatt gggaagagtt    1320
atgcaaattc tcctataagc aaaacaaagc atgtctttga gtaacaatga cctggaaata    1380
cccaaaattc caagttctcg atttcacatg ccttcaagac tgaacaccga ctaaggtttt    1440
catactatta gccaatgctg tagacagaag cattttgata ggaatagagc aaataagata    1500
atggccctga ggaatggcat gtcattatta aagatcatat ggggaaaatg aaaccctccc    1560
caaaatacaa gaagttctgg gaggagacat tgtcttcaga ctacaatgtc cagtttctcc    1620
cctagactca ggcttccttt ggagattaag gcccctcaga gatcaacaga ccaacatttt    1680
tctcttcctc aagcaacact cctagggcct ggcttctgtc tgatcaaggc accacacaac    1740
ccagaaagga gctgatgggg cagaatgaac tttaagtatg agaaaagttc agcccaagta    1800
aaataaaaac tcaatcacat tcaattccag agtagtttca agtttcacat cgtaaccatt    1860
ttcgcccgga attc                                                      1874
```

```
<210> SEQ ID NO 14
<211> LENGTH: 155
<212> TYPE: PRT
<213> ORGANISM: Homo sapiens

<400> SEQUENCE: 14

Met Thr Pro Gly Lys Thr Ser Leu Val Ser Leu Leu Leu Leu Ser
  1               5                  10                  15

Leu Glu Ala Ile Val Lys Ala Gly Ile Thr Ile Pro Arg Asn Pro Gly
                 20                  25                  30

Cys Pro Asn Ser Glu Asp Lys Asn Phe Pro Arg Thr Val Met Val Asn
             35                  40                  45

Leu Asn Ile His Asn Arg Asn Thr Asn Thr Asn Pro Lys Arg Ser Ser
         50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155
```

```
<210> SEQ ID NO 15
<211> LENGTH: 923
<212> TYPE: DNA
<213> ORGANISM: Homo sapiens

<400> SEQUENCE: 15
ggcttcagtt actagctagg ctactgagtt tagttctcag tttggcacct tgataccttt     60
aggtgtgagt gttcccattt ccaggtgagg aactgaggtg caaagagaag ccctgatccc    120
ataaaaggac aggaatgctg agttccgcca gaccatgcat ctcttgctag taggtgaggc    180
gagtctctaa ctgattgcag cgtcttctat tttccaggtc aagtacttgc tgctgtcgat    240
```

-continued

| | |
|---|---|
| attggggctt gcctttctga gtgaggcggc agctcggaaa atccccaaag taggacatac | 300 |
| ttttttccaa aagcctgaga gttgcccgcc tgtgccagga ggtagtatga agcttgacat | 360 |
| tggcatcatc aatgaaaacc agcgcgtttc catgtcacgt aacatcgaga gccgctccac | 420 |
| ctcccccctgg aattacactg tcacttggga ccccaaccgg taccctcgg aagttgtaca | 480 |
| ggcccagtgt aggaacttgg gctgcatcaa tgctcaagga aggaagaca tctccatgaa | 540 |
| ttccgttccc atccagcaag agaccctggt cgtccgagg aagcaccaag gctgctctgt | 600 |
| ttctttccag ttggagaagg tgctggtgac tgttggctgc acctgcgtca ccctgtcat | 660 |
| ccaccatgtg cagtaagagg tgcatatcca ctcagctgaa gaagctgtag aaatgccact | 720 |
| ccttacccag tgctctgcaa caagtcctgt ctgaccccca attccctcca cttcacagga | 780 |
| ctcttaataa gacctgcacg gatggaaaca taaaatattc acaatgtatg tgtgtatgta | 840 |
| ctacacttta tatttgatat ctaaaatgtt aggagaaaaa ttaatatatt cagtgctaat | 900 |
| ataataaagt attaataatg tta | 923 |

<210> SEQ ID NO 16
<211> LENGTH: 153
<212> TYPE: PRT
<213> ORGANISM: Homo sapiens

<400> SEQUENCE: 16

Met Val Lys Tyr Leu Leu Ser Ile Leu Gly Leu Ala Phe Leu Ser
1               5                   10                  15

Glu Ala Ala Arg Lys Ile Pro Lys Val Gly His Thr Phe Phe Gln
            20                  25                  30

Lys Pro Glu Ser Cys Pro Pro Val Pro Gly Gly Ser Met Lys Leu Asp
        35                  40                  45

Ile Gly Ile Ile Asn Glu Asn Gln Arg Val Ser Met Ser Arg Asn Ile
    50                  55                  60

Glu Ser Arg Ser Thr Ser Pro Trp Asn Tyr Thr Val Thr Trp Asp Pro
65                  70                  75                  80

Asn Arg Tyr Pro Ser Glu Val Val Gln Ala Gln Cys Arg Asn Leu Gly
                85                  90                  95

Cys Ile Asn Ala Gln Gly Lys Glu Asp Ile Ser Met Asn Ser Val Pro
            100                 105                 110

Ile Gln Gln Glu Thr Leu Val Val Arg Arg Lys His Gln Gly Cys Ser
        115                 120                 125

Val Ser Phe Gln Leu Glu Lys Val Leu Val Thr Val Gly Cys Thr Cys
    130                 135                 140

Val Thr Pro Val Ile His His Val Gln
145                 150

<210> SEQ ID NO 17
<211> LENGTH: 1172
<212> TYPE: DNA
<213> ORGANISM: Mus musculus

<400> SEQUENCE: 17

| | |
|---|---|
| gatccacctc acacgaggca caagtgcacc cagcaccagc tgatcaggac gcgcaaacat | 60 |
| gagtccaggg agagcttcat ctgtgtctct gatgctgttg ctgctgctga gcctggcggc | 120 |
| tacagtgaag gcagcagcga tcatccctca agctcagcg tgtccaaaca ctgaggccaa | 180 |
| ggacttcctc cagaatgtga aggtcaacct caaagtcttt aactcccttg gcgcaaaagt | 240 |
| gagctccaga aggccctcag actacctcaa ccgttccacg tcaccctgga ctctccaccg | 300 |

```
                                    -continued caatgaagac cctgatagat atccctctgt gatctgggaa gctcagtgcc gccaccagcg      360
ctgtgtcaat gcggagggaa agctggacca ccacatgaat tctgttctca tccagcaaga      420
gatcctggtc ctgaagaggg agcctgagag ctgccccttc actttcaggg tcgagaagat      480
gctggtgggt gtgggctgca cctgcgtggc ctcgattgtc cgccaggcag cctaaacaga      540
gacccgcggc tgaccccctaa gaaaccccca cgtttctcag caaacttact tgcatttta      600 aaacagttcg tgctattgat tttcagcaag gaatgtggat tcagaggcag attcagaatt      660
gtctgccctc cacaatgaaa agaaggtgta aagggggtccc aaactgcttc gtgtttgttt      720
ttctgtggac tttaaattat ttgtgtattt acaatatccc aagatagctt tgaagcgtaa      780
cttattttaa tgaagtatct acattattat tatgtttctt tctgaagaag acaaaattca      840
agactcagaa attttattat ttaaaaggta aagcctatat ttatatgagc tatttatgaa      900
tctatttatt tttcttcagt atttgaagta ttaagaacat gattttcaga tctacctagg      960
gaagtcctaa gtaagattaa atattaatgg aaatttcagc tttactattt gtttatttaa     1020
ggttctctcc tctgaatggg gtgaaaacca aacttagttt tatgtttaat aactttttaa     1080
attattgaag attcaaaaaa ttggataatt tagctcccta ctctgtttta aaaaaaatt      1140 gtaacaatat cactgtaata ataaagtttt gg                                   1172

<210> SEQ ID NO 18
<211> LENGTH: 158
<212> TYPE: PRT
<213> ORGANISM: Mus musculus

<400> SEQUENCE: 18

Met Ser Pro Gly Arg Ala Ser Ser Val Ser Leu Met Leu Leu Leu Leu
  1               5                  10                  15

Leu Ser Leu Ala Ala Thr Val Lys Ala Ala Ile Ile Pro Gln Ser
             20                  25                  30

Ser Ala Cys Pro Asn Thr Glu Ala Lys Asp Phe Leu Gln Asn Val Lys
         35                  40                  45

Val Asn Leu Lys Val Phe Asn Ser Leu Gly Ala Lys Val Ser Ser Arg
     50                  55                  60

Arg Pro Ser Asp Tyr Leu Asn Arg Ser Thr Ser Pro Trp Thr Leu His
 65                  70                  75                  80

Arg Asn Glu Asp Pro Asp Arg Tyr Pro Ser Val Ile Trp Glu Ala Gln
                 85                  90                  95

Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
        115                 120                 125

Pro Glu Ser Cys Pro Phe Thr Phe Arg Val Glu Lys Met Leu Val Gly
    130                 135                 140

Val Gly Cys Thr Cys Val Ala Ser Ile Val Arg Gln Ala Ala
145                 150                 155

<210> SEQ ID NO 19
<211> LENGTH: 462
<212> TYPE: DNA
<213> ORGANISM: Mus musculus

<400> SEQUENCE: 19
atggtcaagt ctttgctact gttgatgttg ggacttgcca ttctgaggga ggtagcagct       60
cggaagaacc ccaaagcagg ggttcctgcc ttgcagaagg ctgggaactg tcctccctg      120
```

```
gaggataaca ctgtgagagt tgacattcga atcttcaacc aaaaccaggg catttctgtc    180
ccacgtgaat tccagaaccg ctccagttcc ccatgggatt acaacatcac tcgagacccc    240
caccggttcc cctcagagat cgctgaggcc cagtgcagac actcaggctg catcaatgcc    300
cagggtcagg aagacagcac catgaactcc gtcgccattc agcaagaaat cctggtcctt    360
cggagggagc cccagggctg ttctaattcc ttcaggttgg agaagatgct cctaaaagtt    420
ggctgcacct gtgtcaagcc cattgtccac caagcggcct ga                      462
```

```
<210> SEQ ID NO 20
<211> LENGTH: 153
<212> TYPE: PRT
<213> ORGANISM: Mus musculus

<400> SEQUENCE: 20

Met Val Lys Ser Leu Leu Leu Met Leu Gly Leu Ala Ile Leu Arg
 1               5                  10                  15

Glu Val Ala Ala Arg Lys Asn Pro Lys Ala Gly Val Pro Ala Leu Gln
                20                  25                  30

Lys Ala Gly Asn Cys Pro Pro Leu Glu Asp Asn Thr Val Arg Val Asp
            35                  40                  45

Ile Arg Ile Phe Asn Gln Asn Gln Gly Ile Ser Val Pro Arg Glu Phe
        50                  55                  60

Gln Asn Arg Ser Ser Ser Pro Trp Asp Tyr Asn Ile Thr Arg Asp Pro
65                  70                  75                  80

His Arg Phe Pro Ser Glu Ile Ala Glu Ala Gln Cys Arg His Ser Gly
                85                  90                  95

Cys Ile Asn Ala Gln Gly Gln Glu Asp Ser Thr Met Asn Ser Val Ala
            100                 105                 110

Ile Gln Gln Glu Ile Leu Val Leu Arg Arg Glu Pro Gln Gly Cys Ser
        115                 120                 125

Asn Ser Phe Arg Leu Glu Lys Met Leu Leu Lys Val Gly Cys Thr Cys
    130                 135                 140

Val Lys Pro Ile Val His Gln Ala Ala
145                 150

<210> SEQ ID NO 21
<211> LENGTH: 320
<212> TYPE: PRT
<213> ORGANISM: Homo sapien

<400> SEQUENCE: 21

Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
```

```
              115                 120                 125
Phe Glu Phe Leu Ser Lys Leu Arg His His Arg Arg Trp Arg Phe
130                 135                 140
Thr Phe Ser His Phe Val Val Asp Pro Asp Gln Glu Tyr Glu Val Thr
145                 150                 155                 160
Val His His Leu Pro Lys Pro Ile Pro Asp Gly Asp Pro Asn His Gln
                165                 170                 175
Ser Lys Asn Phe Leu Val Pro Asp Cys Glu His Ala Arg Met Lys Val
            180                 185                 190
Thr Thr Pro Cys Met Ser Ser Gly Ser Leu Trp Asp Pro Asn Ile Thr
        195                 200                 205
Val Glu Thr Leu Glu Ala His Gln Leu Arg Val Ser Phe Thr Leu Trp
210                 215                 220
Asn Glu Ser Thr His Tyr Gln Ile Leu Leu Thr Ser Phe Pro His Met
225                 230                 235                 240
Glu Asn His Ser Cys Phe Glu His Met His His Ile Pro Ala Pro Arg
                245                 250                 255
Pro Glu Glu Phe His Gln Arg Ser Asn Val Thr Leu Thr Leu Arg Asn
            260                 265                 270
Leu Lys Gly Cys Cys Arg His Gln Val Gln Ile Gln Pro Phe Phe Ser
        275                 280                 285
Ser Cys Leu Asn Asp Cys Leu Arg His Ser Ala Thr Val Ser Cys Pro
290                 295                 300
Glu Met Pro Asp Thr Pro Glu Pro Ile Pro Asp Tyr Met Pro Leu Trp
305                 310                 315                 320

<210> SEQ ID NO 22
<211> LENGTH: 221
<212> TYPE: PRT
<213> ORGANISM: Homo sapien

<400> SEQUENCE: 22

Lys Pro Arg Trp His Lys Asn Leu Thr Gly Pro Gln Ile Ile Thr Leu
1               5                   10                  15
Asn His Thr Asp Leu Val Pro Cys Leu Cys Ile Gln Val Trp Pro Leu
            20                  25                  30
Glu Pro Asp Ser Val Arg Thr Asn Ile Cys Pro Phe Arg Glu Asp Pro
        35                  40                  45
Arg Ala His Gln Asn Leu Trp Gln Ala Ala Arg Leu Arg Leu Leu Thr
    50                  55                  60
Leu Gln Ser Trp Leu Leu Asp Ala Pro Cys Ser Leu Pro Ala Glu Ala
65                  70                  75                  80
Ala Leu Cys Trp Arg Ala Pro Gly Gly Asp Pro Cys Gln Pro Leu Val
                85                  90                  95
Pro Pro Leu Ser Trp Glu Asn Val Thr Val Asp Lys Val Leu Glu Phe
            100                 105                 110
Pro Leu Leu Lys Gly His Pro Asn Leu Cys Val Gln Val Asn Ser Ser
        115                 120                 125
Glu Lys Leu Gln Leu Gln Glu Cys Leu Trp Ala Asp Ser Leu Gly Pro
    130                 135                 140
Leu Lys Asp Asp Val Leu Leu Leu Glu Thr Arg Gly Pro Gln Asp Asn
145                 150                 155                 160
Arg Ser Leu Cys Ala Leu Glu Pro Ser Gly Cys Thr Ser Leu Pro Ser
                165                 170                 175
Lys Ala Ser Thr Arg Ala Ala Arg Leu Gly Glu Tyr Leu Leu Gln Asp
```

```
                    180                 185                 190
Leu Gln Ser Gly Gln Cys Leu Gln Leu Trp Asp Asp Leu Gly Ala
        195                 200                 205

Leu Trp Ala Cys Pro Met Asp Lys Tyr Ile His Lys Arg
        210                 215                 220

<210> SEQ ID NO 23
<211> LENGTH: 2180
<212> TYPE: DNA
<213> ORGANISM: Homo sapien

<400> SEQUENCE: 23
aactacccag cacagccccc tccgccccct ctggaggctg aagagggatt ccagcccctg     60
ccacccacag acacgggctg actggggtgt ctgccccct tggggggggg cagcacaggg    120
cctcaggcct gggtgccacc tggcacctag aagatgcctg tgcctggtt cttgctgtcc    180 ttggcactgg gccgaagccc agtggtcctt tctctggaga ggcttgtggg gcctcaggac    240
gctacccact gctctccggg cctctcctgc cgcctctggg acagtgacat actctgcctg    300
cctggggaca tcgtgcctgc tccggggccc gtgctggcgc tacgcacct gcagacagag    360 ctggtgctga ggtgccagaa ggagaccgac tgtgacctct gtctgcgtgt ggctgtccac    420
ttggccgtgc atgcctctct ccaggcccaa gtcgtgctct ccttccaggc ctaccctact    480
gcccgctgcg tcctgctgga ggtgcaagtg cctgctgccc ttgtgcagtt tggtcagtct    540
gtgggctctg tggtatatga ctgcttcgag gctgccctag ggagtgaggt acgaatctgg    600
tcctatactc agcccaggta cgagaaggaa ctcaaccaca cacagcagct gcctgccctg    660
ccctggctca acgtgtcagc agatggtgac aacgtgcatc tggttctgaa tgtctctgag    720
gagcagcact tcggcctctc cctgtactgg aatcaggtcc agggccccccc aaaaccccgg    780 tggcacaaaa acctgactgg accgcagatc attaccttga ccacacaga cctggttccc    840 tgcctctgta ttcaggtgtg gcctctggaa cctgactccg ttaggacgaa catctgcccc    900
ttcagggagg accccccgcgc acaccagaac ctctggcaag ccgcccgact gcgactgctg    960
accctgcaga gctggctgct ggacgcaccg tgctcgctgc ccgcagaagc ggcactgtgc   1020
tggcgggctc cgggtgggga cccctgccag ccactggtcc caccgctttc ctgggagaac   1080
gtcactgtgg acaaggttct cgagttccca ttgctgaaag gccacccctaa cctctgtgtt   1140 caggtgaaca gctcggagaa gctgcagctg caggagtgct tgtgggctga ctccctgggg   1200
cctctcaaag acgatgtgct actgttggag acacgaggcc cccaggacaa cagatccctc   1260
tgtgccttgg aacccagtgg ctgtacttca ctacccagca aagcctccac gagggcagct   1320
cgccttggag agtacttact acaagacctg cagtcaggcc agtgtctgca gctatgggac   1380
gatgacttgg gagcgctatg gccctgcccc atggacaaat acatccacaa gcgctgggcc   1440
ctcgtgtggc tggcctgcct actctttgcc gctgcgcttt ccctcatcct ccttctcaaa   1500
aaggatcacg cgaaagcggc cgccagggggc gcgcggctc tgctcctcta tcagccgat   1560 gactcgggtt tcgagcgcct ggtgggcgcc ctggcgtcgg ccctgtgcca gctgccgctg   1620
cgcgtggccg tagacctgtg gagccgtcgt gaactgagcg cgcaggggcc cgtggcttgg   1680
tttcacgcgc agcggcgcca gaccctgcag gagggcggcg tggtggtctt gctcttctct   1740
cccggtgcgg tggcgctgtg cagcgagtgg ctacaggatg gggtgtccgg gcccggggcg   1800 cacggccccgc acgacgcctt ccgcgcctcg ctcagctgcg tgctgcccga cttcttgcag   1860
ggccgggcgc ccggcagcta cgtggggggcc tgcttcgaca ggctgctcca cccggacgcc   1920
```

```
gtacccgccc ttttccgcac cgtgcccgtc ttcacactgc cctcccaact gccagacttc    1980
ctgggggccc tgcagcagcc tcgcgccccg cgttccgggc ggctccaaga gagagcggag    2040
caagtgtccc gggcccttca gccagccctg gatagctact tccatccccc ggggactccc    2100
gcgccgggac gcggggtggg accagggggcg ggacctgggg cggggacgg gacttaaata    2160 aaggcagacg ctgttttttct                                                2180
```

<210> SEQ ID NO 24
<211> LENGTH: 667
<212> TYPE: PRT
<213> ORGANISM: Homo sapien

<400> SEQUENCE: 24

```
Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
 50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Ala Ser Leu
                 85                  90                  95

Gln Ala Gln Val Val Leu Ser Phe Gln Ala Tyr Pro Thr Ala Arg Cys
            100                 105                 110

Val Leu Leu Glu Val Gln Val Pro Ala Ala Leu Val Gln Phe Gly Gln
        115                 120                 125

Ser Val Gly Ser Val Val Tyr Asp Cys Phe Glu Ala Ala Leu Gly Ser
    130                 135                 140

Glu Val Arg Ile Trp Ser Tyr Thr Gln Pro Arg Tyr Glu Lys Glu Leu
145                 150                 155                 160

Asn His Thr Gln Gln Leu Pro Ala Leu Pro Trp Leu Asn Val Ser Ala
                165                 170                 175

Asp Gly Asp Asn Val His Leu Val Leu Asn Val Ser Glu Glu Gln His
            180                 185                 190

Phe Gly Leu Ser Leu Tyr Trp Asn Gln Val Gln Gly Pro Pro Lys Pro
        195                 200                 205

Arg Trp His Lys Asn Leu Thr Gly Pro Gln Ile Ile Thr Leu Asn His
    210                 215                 220

Thr Asp Leu Val Pro Cys Leu Cys Ile Gln Val Trp Pro Leu Glu Pro
225                 230                 235                 240

Asp Ser Val Arg Thr Asn Ile Cys Pro Phe Arg Glu Asp Pro Arg Ala
                245                 250                 255

His Gln Asn Leu Trp Gln Ala Ala Arg Leu Arg Leu Leu Thr Leu Gln
            260                 265                 270

Ser Trp Leu Leu Asp Ala Pro Cys Ser Leu Pro Ala Glu Ala Ala Leu
        275                 280                 285

Cys Trp Arg Ala Pro Gly Gly Asp Pro Cys Gln Pro Leu Val Pro Pro
    290                 295                 300

Leu Ser Trp Glu Asn Val Thr Val Asp Lys Val Leu Glu Phe Pro Leu
305                 310                 315                 320

Leu Lys Gly His Pro Asn Leu Cys Val Gln Val Asn Ser Ser Glu Lys
                325                 330                 335
```

```
Leu Gln Leu Gln Glu Cys Leu Trp Ala Asp Ser Leu Gly Pro Leu Lys
            340                 345                 350

Asp Asp Val Leu Leu Glu Thr Arg Gly Pro Gln Asp Asn Arg Ser
        355                 360                 365

Leu Cys Ala Leu Glu Pro Ser Gly Cys Thr Ser Leu Pro Ser Lys Ala
370                 375                 380

Ser Thr Arg Ala Ala Arg Leu Gly Glu Tyr Leu Leu Gln Asp Leu Gln
385                 390                 395                 400

Ser Gly Gln Cys Leu Gln Leu Trp Asp Asp Leu Gly Ala Leu Trp
            405                 410                 415

Ala Cys Pro Met Asp Lys Tyr Ile His Lys Arg Trp Ala Leu Val Trp
            420                 425                 430

Leu Ala Cys Leu Leu Phe Ala Ala Ala Leu Ser Leu Ile Leu Leu Leu
            435                 440                 445

Lys Lys Asp His Ala Lys Ala Ala Arg Gly Arg Ala Ala Leu Leu
450                 455                 460

Leu Tyr Ser Ala Asp Asp Ser Gly Phe Glu Arg Leu Val Gly Ala Leu
465                 470                 475                 480

Ala Ser Ala Leu Cys Gln Leu Pro Leu Arg Val Ala Val Asp Leu Trp
            485                 490                 495

Ser Arg Arg Glu Leu Ser Ala Gln Gly Pro Val Ala Trp Phe His Ala
            500                 505                 510

Gln Arg Arg Gln Thr Leu Gln Glu Gly Gly Val Val Leu Leu Phe
            515                 520                 525

Ser Pro Gly Ala Val Ala Leu Cys Ser Glu Trp Leu Gln Asp Gly Val
530                 535                 540

Ser Gly Pro Gly Ala His Gly Pro His Asp Ala Phe Arg Ala Ser Leu
545                 550                 555                 560

Ser Cys Val Leu Pro Asp Phe Leu Gln Gly Arg Ala Pro Gly Ser Tyr
            565                 570                 575

Val Gly Ala Cys Phe Asp Arg Leu Leu His Pro Asp Ala Val Pro Ala
            580                 585                 590

Leu Phe Arg Thr Val Pro Val Phe Thr Leu Pro Ser Gln Leu Pro Asp
            595                 600                 605

Phe Leu Gly Ala Leu Gln Gln Pro Arg Ala Pro Arg Ser Gly Arg Leu
610                 615                 620

Gln Glu Arg Ala Glu Gln Val Ser Arg Ala Leu Gln Pro Ala Leu Asp
625                 630                 635                 640

Ser Tyr Phe His Pro Pro Gly Thr Pro Ala Pro Gly Arg Gly Val Gly
            645                 650                 655

Pro Gly Ala Gly Pro Gly Ala Gly Asp Gly Thr
            660                 665

<210> SEQ ID NO 25
<211> LENGTH: 2269
<212> TYPE: DNA
<213> ORGANISM: Mus musculus

<400> SEQUENCE: 25
aaatcgaaag cactccagct gaaactgggc ctggagtcca ggctcactgg agtggggaag      60
catggctgga gaggaattct agcccttgct ctctcccagg acacggggc tgattgtcag     120 caggggcgag gggtctgccc ccccttgggg gggcaggacg gggcctcagg cctgggtgct    180
gtccggcacc tggaagatgc ctgtgtcctg gttcctgctg tccttggcac tgggccgaaa    240
```

```
cctgtggtc gtctctctgg agagactgat ggagcctcag gacactgcac gctgctctct    300
aggcctctcc tgccacctct gggatggtga cgtgctctgc ctgcctggaa gcctccagtc    360
tgccccaggc cctgtgctag tgcctacccg cctgcagacg gagctggtgc tgaggtgtcc    420
acagaagaca gattgcgccc tctgtgtccg tgtggtggtc cacttggccg tgcatgggca    480
ctgggcagag cctgaagaag ctggaaagtc tgattcagaa ctccaggagt ctaggaacgc    540
ctctctccag gcccaggtgg tgctctcctt ccaggcctac cccatcgccc gctgtgccct    600
gctggaggtc caggtgcccg ctgacctggt gcagcctggt cagtccgtgg gttctgcggt    660
atttgactgt ttcgaggcta gtcttggggc tgaggtacag atctggtcct acacgaagcc    720
caggtaccag aaagagctca acctcacaca gcagctgcct gtcctgccct ggctcaatgt    780
gtctacagat ggtgacaatg tccttctgac actggatgtc tctgaggagc aggactttag    840
cttcttactg tacctgcgtc cagtcccgga tgctctcaaa tccttgtggt acaaaaacct    900
gactggacct cagaacatta ctttaaacca cacagacctg gttccctgcc tctgcattca    960
ggtgtggtcg ctagagccag actctgagag ggtcgaattc tgccccttcc gggaagatcc    1020
cggtgcacac aggaacctct ggcacatagc caggctgcgg gtactgtccc aggggtatg    1080 gcagctagat gcgccttgct gtctgccggg caaggtaaca ctgtgctggc aggcaccaga    1140
ccagagtccc tgccagccac ttgtgccacc agtgccccag aagaacgcca ctgtgaatga    1200
gccacaagat ttccagttgg tggcaggcca ccccaacctc tgtgtccagg tgagcacctg    1260
ggagaaggtt cagctgcaag cgtgcttgtg ggctgactcc ttggggccct caaggatga    1320 tatgctgtta gtggagatga aaaccggcct caacaacaca tcagtctgtg ccttggaacc    1380
cagtggctgt acaccactgc ccagcatggc ctccacgaga gctgctcgcc tgggagagga    1440
gttgctgcaa gacttccgat cacaccagtg tatgcagctg tggaacgatg acaacatggg    1500
atcgctatgg gcctgcccca tggacaagta catccacagg cgctgggtcc tagtatggct    1560
ggcctgccta ctcttggctg cggcgctttt cttcttcctc cttctaaaaa aggaccgcag    1620
gaaagcggcc cgtggctccc gcacggcctt gctcctccac tccgccgacg gagcgggcta    1680
cgagcgtctg gtgggagcac tggcgtccgc gttgagccaa atgccactgc gcgtggccgt    1740
ggacctgtgg agccgccgcg agctgagcgc gcacggagcc ctagcctggt tccaccacca    1800
gcgacgccgt atcctgcagg agggtggcgt ggtaatcctt ctcttctcgc ccgcggccgt    1860
ggcgcagtgt cagcagtggc tgcagctcca gacagtggag cccgggccgc atgacgccct    1920
cgccgcctgg ctcagctgcg tgctacccga tttcctgcaa ggccgggcga ccggccgcta    1980
cgtcggggtc tacttcgacg ggctgctgca cccagactct gtgccctccc gttccgcgt    2040 cgccccgctc ttctccctgc cctcgcagct gccggctttc ctggatgcac tgcagggagg    2100
ctgctccact tccgcggggc gacccgcgga ccgggtggaa cgagtgaccc aggcgctgcg    2160
gtccgccctg gacagctgta cttctagctc ggaagcccca ggctgctgcg aggaatggga    2220
cctgggaccc tgcactacac tagaataaaa gccgatacag tattcctaa              2269
```

<210> SEQ ID NO 26
<211> LENGTH: 683
<212> TYPE: PRT
<213> ORGANISM: Mus musculus

<400> SEQUENCE: 26

Met Pro Val Ser Trp Phe Leu Leu Ser Leu Ala Leu Gly Arg Asn Pro
1               5                   10                  15

Val Val Val Ser Leu Glu Arg Leu Met Glu Pro Gln Asp Thr Ala Arg

```
              20                  25                  30
Cys Ser Leu Gly Leu Ser Cys His Leu Trp Asp Gly Asp Val Leu Cys
             35                  40                  45

Leu Pro Gly Ser Leu Gln Ser Ala Pro Gly Pro Val Leu Val Pro Thr
 50                  55                  60

Arg Leu Gln Thr Glu Leu Val Leu Arg Cys Pro Gln Lys Thr Asp Cys
 65                  70                  75                  80

Ala Leu Cys Val Arg Val Val His Leu Ala Val His Gly His Trp
                 85                  90                  95

Ala Glu Pro Glu Glu Ala Gly Lys Ser Asp Ser Glu Leu Gln Glu Ser
                100                 105                 110

Arg Asn Ala Ser Leu Gln Ala Gln Val Val Leu Ser Phe Gln Ala Tyr
            115                 120                 125

Pro Ile Ala Arg Cys Ala Leu Leu Glu Val Gln Val Pro Ala Asp Leu
        130                 135                 140

Val Gln Pro Gly Gln Ser Val Gly Ser Ala Val Phe Asp Cys Phe Glu
145                 150                 155                 160

Ala Ser Leu Gly Ala Glu Val Gln Ile Trp Ser Tyr Thr Lys Pro Arg
                165                 170                 175

Tyr Gln Lys Glu Leu Asn Leu Thr Gln Gln Leu Pro Val Leu Pro Trp
            180                 185                 190

Leu Asn Val Ser Thr Asp Gly Asp Asn Val Leu Leu Thr Leu Asp Val
        195                 200                 205

Ser Glu Glu Gln Asp Phe Ser Phe Leu Leu Tyr Leu Arg Pro Val Pro
    210                 215                 220

Asp Ala Leu Lys Ser Leu Trp Tyr Lys Asn Leu Thr Gly Pro Gln Asn
225                 230                 235                 240

Ile Thr Leu Asn His Thr Asp Leu Val Pro Cys Leu Cys Ile Gln Val
                245                 250                 255

Trp Ser Leu Glu Pro Asp Ser Glu Arg Val Glu Phe Cys Pro Phe Arg
            260                 265                 270

Glu Asp Pro Gly Ala His Arg Asn Leu Trp His Ile Ala Arg Leu Arg
        275                 280                 285

Val Leu Ser Pro Gly Val Trp Gln Leu Asp Ala Pro Cys Cys Leu Pro
    290                 295                 300

Gly Lys Val Thr Leu Cys Trp Gln Ala Pro Asp Gln Ser Pro Cys Gln
305                 310                 315                 320

Pro Leu Val Pro Val Pro Gln Lys Asn Ala Thr Val Asn Glu Pro
                325                 330                 335

Gln Asp Phe Gln Leu Val Ala Gly His Pro Asn Leu Cys Val Gln Val
            340                 345                 350

Ser Thr Trp Glu Lys Val Gln Leu Gln Ala Cys Leu Trp Ala Asp Ser
        355                 360                 365

Leu Gly Pro Phe Lys Asp Asp Met Leu Leu Val Glu Met Lys Thr Gly
    370                 375                 380

Leu Asn Asn Thr Ser Val Cys Ala Leu Glu Pro Ser Gly Cys Thr Pro
385                 390                 395                 400

Leu Pro Ser Met Ala Ser Thr Arg Ala Ala Arg Leu Gly Glu Glu Leu
                405                 410                 415

Leu Gln Asp Phe Arg Ser His Gln Cys Met Gln Leu Trp Asn Asp Asp
            420                 425                 430

Asn Met Gly Ser Leu Trp Ala Cys Pro Met Asp Lys Tyr Ile His Arg
        435                 440                 445
```

```
Arg Trp Val Leu Val Trp Leu Ala Cys Leu Leu Ala Ala Ala Leu
450                 455                 460

Phe Phe Phe Leu Leu Leu Lys Lys Asp Arg Arg Lys Ala Ala Arg Gly
465                 470                 475                 480

Ser Arg Thr Ala Leu Leu His Ser Ala Asp Gly Ala Gly Tyr Glu
                485                 490                 495

Arg Leu Val Gly Ala Leu Ala Ser Ala Leu Ser Gln Met Pro Leu Arg
                500                 505                 510

Val Ala Val Asp Leu Trp Ser Arg Arg Glu Leu Ser Ala His Gly Ala
                515                 520                 525

Leu Ala Trp Phe His His Gln Arg Arg Ile Leu Gln Glu Gly Gly
                530                 535                 540

Val Val Ile Leu Leu Phe Ser Pro Ala Val Ala Gln Cys Gln Gln
545                 550                 555                 560

Trp Leu Gln Leu Gln Thr Val Glu Pro Gly Pro His Asp Ala Leu Ala
                565                 570                 575

Ala Trp Leu Ser Cys Val Leu Pro Asp Phe Leu Gln Gly Arg Ala Thr
                580                 585                 590

Gly Arg Tyr Val Gly Val Tyr Phe Asp Gly Leu Leu His Pro Asp Ser
                595                 600                 605

Val Pro Ser Pro Phe Arg Val Ala Pro Leu Phe Ser Leu Pro Ser Gln
                610                 615                 620

Leu Pro Ala Phe Leu Asp Ala Leu Gln Gly Gly Cys Ser Thr Ser Ala
625                 630                 635                 640

Gly Arg Pro Ala Asp Arg Val Glu Arg Val Thr Gln Ala Leu Arg Ser
                645                 650                 655

Ala Leu Asp Ser Cys Thr Ser Ser Glu Ala Pro Gly Cys Cys Glu
                660                 665                 670

Glu Trp Asp Leu Gly Pro Cys Thr Thr Leu Glu
                675                 680

<210> SEQ ID NO 27
<211> LENGTH: 449
<212> TYPE: PRT
<213> ORGANISM: Mus musculus

<400> SEQUENCE: 27

Met Pro Val Ser Trp Phe Leu Leu Ser Leu Ala Leu Gly Arg Asn Pro
1               5                   10                  15

Val Val Val Ser Leu Glu Arg Leu Met Glu Pro Gln Asp Thr Ala Arg
                20                  25                  30

Cys Ser Leu Gly Leu Ser Cys His Leu Trp Asp Gly Asp Val Leu Cys
                35                  40                  45

Leu Pro Gly Ser Leu Gln Ser Ala Pro Gly Pro Val Leu Val Pro Thr
            50                  55                  60

Arg Leu Gln Thr Glu Leu Val Arg Cys Pro Gln Lys Thr Asp Cys
65                  70                  75                  80

Ala Leu Cys Val Arg Val Val His Leu Ala Val His Gly His Trp
                85                  90                  95

Ala Glu Pro Glu Glu Ala Gly Lys Ser Asp Ser Glu Leu Gln Glu Ser
                100                 105                 110

Arg Asn Ala Ser Leu Gln Ala Gln Val Val Leu Ser Phe Gln Ala Tyr
                115                 120                 125

Pro Ile Ala Arg Cys Ala Leu Leu Glu Val Gln Val Pro Ala Asp Leu
                130                 135                 140
```

```
Val Gln Pro Gly Gln Ser Val Gly Ser Ala Val Phe Asp Cys Phe Glu
145                 150                 155                 160

Ala Ser Leu Gly Ala Glu Val Gln Ile Trp Ser Tyr Thr Lys Pro Arg
                165                 170                 175

Tyr Gln Lys Glu Leu Asn Leu Thr Gln Gln Leu Pro Val Leu Pro Trp
            180                 185                 190

Leu Asn Val Ser Thr Asp Gly Asp Asn Val Leu Thr Leu Asp Val
        195                 200                 205

Ser Glu Glu Gln Asp Phe Ser Phe Leu Leu Tyr Leu Arg Pro Val Pro
    210                 215                 220

Asp Ala Leu Lys Ser Leu Trp Tyr Lys Asn Leu Thr Gly Pro Gln Asn
225                 230                 235                 240

Ile Thr Leu Asn His Thr Asp Leu Val Pro Cys Leu Cys Ile Gln Val
                245                 250                 255

Trp Ser Leu Glu Pro Asp Ser Glu Arg Val Glu Phe Cys Pro Phe Arg
                260                 265                 270

Glu Asp Pro Gly Ala His Arg Asn Leu Trp His Ile Ala Arg Leu Arg
            275                 280                 285

Val Leu Ser Pro Gly Val Trp Gln Leu Asp Ala Pro Cys Cys Leu Pro
        290                 295                 300

Gly Lys Val Thr Leu Cys Trp Gln Ala Pro Asp Gln Ser Pro Cys Gln
305                 310                 315                 320

Pro Leu Val Pro Pro Val Pro Gln Lys Asn Ala Thr Val Asn Glu Pro
                325                 330                 335

Gln Asp Phe Gln Leu Val Ala Gly His Pro Asn Leu Cys Val Gln Val
            340                 345                 350

Ser Thr Trp Glu Lys Val Gln Leu Gln Ala Cys Leu Trp Ala Asp Ser
        355                 360                 365

Leu Gly Pro Phe Lys Asp Asp Met Leu Leu Val Glu Met Lys Thr Gly
    370                 375                 380

Leu Asn Asn Thr Ser Val Cys Ala Leu Glu Pro Ser Gly Cys Thr Pro
385                 390                 395                 400

Leu Pro Ser Met Ala Ser Thr Arg Ala Ala Arg Leu Gly Glu Glu Leu
                405                 410                 415

Leu Gln Asp Phe Arg Ser His Gln Cys Met Gln Leu Trp Asn Asp Asp
            420                 425                 430

Asn Met Gly Ser Leu Trp Ala Cys Pro Met Asp Lys Tyr Ile His Arg
        435                 440                 445
Arg

<210> SEQ ID NO 28
<211> LENGTH: 222
<212> TYPE: PRT
<213> ORGANISM: Mus musculus

<400> SEQUENCE: 28

Lys Ser Leu Trp Tyr Lys Asn Leu Thr Gly Pro Gln Asn Ile Thr Leu
1               5                   10                  15

Asn His Thr Asp Leu Val Pro Cys Leu Cys Ile Gln Val Trp Ser Leu
            20                  25                  30

Glu Pro Asp Ser Glu Arg Val Glu Phe Cys Pro Phe Arg Glu Asp Pro
        35                  40                  45

Gly Ala His Arg Asn Leu Trp His Ile Ala Arg Leu Arg Val Leu Ser
    50                  55                  60

Pro Gly Val Trp Gln Leu Asp Ala Pro Cys Cys Leu Pro Gly Lys Val
```

```
              65                  70                  75                  80
Thr Leu Cys Trp Gln Ala Pro Asp Gln Ser Pro Cys Gln Pro Leu Val
                      85                  90                  95
Pro Pro Val Pro Gln Lys Asn Ala Thr Val Asn Glu Pro Gln Asp Phe
            100                 105                 110
Gln Leu Val Ala Gly His Pro Asn Leu Cys Val Gln Val Ser Thr Trp
        115                 120                 125
Glu Lys Val Gln Leu Gln Ala Cys Leu Trp Ala Asp Ser Leu Gly Pro
    130                 135                 140
Phe Lys Asp Asp Met Leu Leu Val Glu Met Lys Thr Gly Leu Asn Asn
145                 150                 155                 160
Thr Ser Val Cys Ala Leu Glu Pro Ser Gly Cys Thr Pro Leu Pro Ser
                165                 170                 175
Met Ala Ser Thr Arg Ala Ala Arg Leu Gly Glu Leu Leu Gln Asp
            180                 185                 190
Phe Arg Ser His Gln Cys Met Gln Leu Trp Asn Asp Asp Asn Met Gly
        195                 200                 205
Ser Leu Trp Ala Cys Pro Met Asp Lys Tyr Ile His Arg Arg
    210                 215                 220

<210> SEQ ID NO 29
<211> LENGTH: 2287
<212> TYPE: DNA
<213> ORGANISM: Mus musculus

<400> SEQUENCE: 29
aaatcgaaag cactccagct gaaactgggc ctggagtcca ggctcactgg agtggggaag      60
catggctgga gaggaattct agcccttgct ctctcccagg acacggggc tgattgtcag      120
caggggcgag gggtctgccc cccttgggg gggcaggacg gggcctcagg cctgggtgct      180
gtccggcacc tggaagatgc ctgtgtcctg gttcctgctg tccttggcac tgggccgaaa      240
ccctgtggtc gtctctctgg agagactgat ggagcctcag acactgcac gctgctctct      300
aggcctctcc tgccacctct gggatggtga cgtgctctgc ctgcctggaa gcctccagtc      360
tgccccaggc cctgtgctag tgcctaccg cctgcagacg gagctggtgc tgaggtgtcc      420
acagaagaca gattgcgccc tctgtgtccg tgtggtggtc acttggccg tgcatgggca      480
ctgggcagag cctgaagaag ctggaaagtc tgattcagaa ctccaggagt ctaggaacgc      540
ctctctccag gcccaggtgg tgctctcctt ccaggcctac cccatcgccc gctgtgccct      600
gctggaggtc caggtgcccg ctgacctggt gcagcctggt cagtccgtgg ttctgcggt      660
atttgactgt ttcgaggcta gtcttggggc tgaggtacag atctggtcct acacgaagcc      720
caggtaccag aaaagagctca acctcacaca gcagctgcct gactgcaggg gtcttgaagt      780
ccggacagc atccagagct gctgggatgg tgacaatgtc cttctgacac tggatgtctc      840
tgaggagcag gactttagct tcttactgta cctgcgtcca gtcccggatg ctctcaaatc      900
cttgtggtac aaaaacctga ctggacctca gaacattact ttaaaccaca cagacctggt      960
tccctgcctc tgcattcagg tgtggtcgct agagccagac tctgagaggg tcgaattctg     1020
cccctcccgg gaagatcccg gtgcacacag gaacctctgg cacatagcca ggctgcgggt     1080
actgtcccca ggggtatggc agctagatgc gccttgctgt ctgccgggca aggtaacact     1140
gtgctggcag gcaccagacc agagtccctg ccagccactt gtgccaccag tgccccagaa     1200
gaacgccact gtgaatgagc cacaagattt ccagttggtg gcaggccacc caacctctg     1260
tgtccaggtg agcacctggg agaaggttca gctgcaagcg tgcttgtggg ctgactcctt     1320
```

```
ggggcccttc aaggatgata tgctgttagt ggagatgaaa accggcctca acaacacatc    1380
agtctgtgcc ttggaaccca gtggctgtac accactgccc agcatggcct ccacgagagc    1440
tgctcgcctg ggagaggagt tgctgcaaga cttccgatca caccagtgta tgcagctgtg    1500
gaacgatgac aacatgggat cgctatgggc ctgccccatg acaagtaca  tccacaggcg    1560
ctgggtccta gtatggctgg cctgcctact cttggctgcg cgcttttct  tcttcctcct    1620
tctaaaaaag gaccgcagga aagcggcccg tggctcccgc acggccttgc tcctccactc    1680
cgccgacgga gcgggctacg agcgtctggt gggagcactg gcgtccgcgt tgagccagat    1740
gccactgcgc gtggccgtgg acctgtggag ccgccgcgag ctgagcgcgc acggagccct    1800
agcctggttc caccaccagc gacgccgtat cctgcaggag ggtggcgtgg taatccttct    1860
cttctcgccc gcggccgtgg cgcagtgtca gcagtggctg cagctccaga cagtggagcc    1920
cgggccgcat gacgccctcg ccgcctggct cagctgcgtg ctacccgatt tcctgcaagg    1980
ccgggcgacc ggccgctacg tcggggtcta cttcgacggg ctgctgcacc cagactctgt    2040
gccctccccg ttccgcgtcg ccccgctctt ctccctgccc tcgcagctgc cggctttcct    2100
ggatgcactg cagggaggct gctccacttc gcggggcga  cccgcggacc gggtggaacg    2160
agtgacccag gcgctgcggt ccgccctgga cagctgtact tctagctcgg aagccccagg    2220
ctgctgcgag gaatgggacc tgggaccctg cactacacta gaataaaagc cgatacagta    2280
ttcctaa                                                               2287

<210> SEQ ID NO 30
<211> LENGTH: 689
<212> TYPE: PRT
<213> ORGANISM: Mus musculus

<400> SEQUENCE: 30

Met Pro Val Ser Trp Phe Leu Leu Ser Leu Ala Leu Gly Arg Asn Pro
 1               5                  10                  15

Val Val Val Ser Leu Glu Arg Leu Met Glu Pro Gln Asp Thr Ala Arg
             20                  25                  30

Cys Ser Leu Gly Leu Ser Cys His Leu Trp Asp Gly Asp Val Leu Cys
         35                  40                  45

Leu Pro Gly Ser Leu Gln Ser Ala Pro Gly Pro Val Leu Val Pro Thr
     50                  55                  60

Arg Leu Gln Thr Glu Leu Val Leu Arg Cys Pro Gln Lys Thr Asp Cys
 65                  70                  75                  80

Ala Leu Cys Val Arg Val Val His Leu Ala Val His Gly His Trp
                 85                  90                  95

Ala Glu Pro Glu Glu Ala Gly Lys Ser Asp Ser Glu Leu Gln Glu Ser
            100                 105                 110

Arg Asn Ala Ser Leu Gln Ala Gln Val Val Leu Ser Phe Gln Ala Tyr
        115                 120                 125

Pro Ile Ala Arg Cys Ala Leu Leu Glu Val Gln Val Pro Ala Asp Leu
    130                 135                 140

Val Gln Pro Gly Gln Ser Val Gly Ser Ala Val Phe Asp Cys Phe Glu
145                 150                 155                 160

Ala Ser Leu Gly Ala Glu Val Gln Ile Trp Ser Tyr Thr Lys Pro Arg
                165                 170                 175

Tyr Gln Lys Glu Leu Asn Leu Thr Gln Gln Leu Pro Asp Cys Arg Gly
            180                 185                 190

Leu Glu Val Arg Asp Ser Ile Gln Ser Cys Trp Asp Gly Asp Asn Val
```

```
                195                 200                 205
Leu Leu Thr Leu Asp Val Ser Glu Glu Gln Asp Phe Ser Phe Leu Leu
    210                 215                 220
Tyr Leu Arg Pro Val Pro Asp Ala Leu Lys Ser Leu Trp Tyr Lys Asn
225                 230                 235                 240
Leu Thr Gly Pro Gln Asn Ile Thr Leu Asn His Thr Asp Leu Val Pro
                245                 250                 255
Cys Leu Cys Ile Gln Val Trp Ser Leu Glu Pro Asp Ser Glu Arg Val
                260                 265                 270
Glu Phe Cys Pro Phe Arg Glu Asp Pro Gly Ala His Arg Asn Leu Trp
            275                 280                 285
His Ile Ala Arg Leu Arg Val Leu Ser Pro Gly Val Trp Gln Leu Asp
        290                 295                 300
Ala Pro Cys Cys Leu Pro Gly Lys Val Thr Leu Cys Trp Gln Ala Pro
305                 310                 315                 320
Asp Gln Ser Pro Cys Gln Pro Leu Val Pro Val Pro Gln Lys Asn
                325                 330                 335
Ala Thr Val Asn Glu Pro Gln Asp Phe Gln Leu Val Ala Gly His Pro
            340                 345                 350
Asn Leu Cys Val Gln Val Ser Thr Trp Glu Lys Val Gln Leu Gln Ala
            355                 360                 365
Cys Leu Trp Ala Asp Ser Leu Gly Pro Phe Lys Asp Asp Met Leu Leu
        370                 375                 380
Val Glu Met Lys Thr Gly Leu Asn Asn Thr Ser Val Cys Ala Leu Glu
385                 390                 395                 400
Pro Ser Gly Cys Thr Pro Leu Pro Ser Met Ala Ser Thr Arg Ala Ala
                405                 410                 415
Arg Leu Gly Glu Glu Leu Leu Gln Asp Phe Arg Ser His Gln Cys Met
            420                 425                 430
Gln Leu Trp Asn Asp Asp Asn Met Gly Ser Leu Trp Ala Cys Pro Met
        435                 440                 445
Asp Lys Tyr Ile His Arg Arg Trp Val Leu Val Trp Leu Ala Cys Leu
    450                 455                 460
Leu Leu Ala Ala Ala Leu Phe Phe Phe Leu Leu Leu Lys Lys Asp Arg
465                 470                 475                 480
Arg Lys Ala Ala Arg Gly Ser Arg Thr Ala Leu Leu Leu His Ser Ala
                485                 490                 495
Asp Gly Ala Gly Tyr Glu Arg Leu Val Gly Ala Leu Ala Ser Ala Leu
            500                 505                 510
Ser Gln Met Pro Leu Arg Val Ala Val Asp Leu Trp Ser Arg Arg Glu
        515                 520                 525
Leu Ser Ala His Gly Ala Leu Ala Trp Phe His His Gln Arg Arg Arg
    530                 535                 540
Ile Leu Gln Glu Gly Gly Val Val Ile Leu Leu Phe Ser Pro Ala Ala
545                 550                 555                 560
Val Ala Gln Cys Gln Gln Trp Leu Gln Leu Gln Thr Val Glu Pro Gly
                565                 570                 575
Pro His Asp Ala Leu Ala Ala Trp Leu Ser Cys Val Leu Pro Asp Phe
            580                 585                 590
Leu Gln Gly Arg Ala Thr Gly Arg Tyr Val Gly Val Tyr Phe Asp Gly
            595                 600                 605
Leu Leu His Pro Asp Ser Val Pro Ser Pro Phe Arg Val Ala Pro Leu
        610                 615                 620
```

```
Phe Ser Leu Pro Ser Gln Leu Pro Ala Phe Leu Asp Ala Leu Gln Gly
625                 630                 635                 640

Gly Cys Ser Thr Ser Ala Gly Arg Pro Ala Asp Arg Val Glu Arg Val
            645                 650                 655

Thr Gln Ala Leu Arg Ser Ala Leu Asp Ser Cys Thr Ser Ser Ser Glu
        660                 665                 670

Ala Pro Gly Cys Cys Glu Glu Trp Asp Leu Gly Pro Cys Thr Thr Leu
        675                 680                 685

Glu

<210> SEQ ID NO 31
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 31
tcccgtcccc cgccccaggt c                                        21

<210> SEQ ID NO 32
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 32
ctctccatcc ttatctttca tcaac                                    25

<210> SEQ ID NO 33
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 33
ctctctgctg gctaaacaaa acac                                     24

<210> SEQ ID NO 34
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 34
ctcatattgc tcaactgtgt gaaaag                                   26

<210> SEQ ID NO 35
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 35
tagaagccac ctgaacacaa atctg                                    25

<210> SEQ ID NO 36
<211> LENGTH: 28
<212> TYPE: DNA
<213> ORGANISM: Artificial Sequence
<220> FEATURE:
```

```
<223> OTHER INFORMATION: oligonucleotide primer

<400> SEQUENCE: 36
atcttgcgtt gtatgttgaa aatcaatt                                          28

<210> SEQ ID NO 37
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 37
ttctccacca ggtaaacaag tctac                                             25

<210> SEQ ID NO 38
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 38
ctctccaggc ccaagtcgtg ctct                                              24

<210> SEQ ID NO 39
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 39
ttgtcctggg ggcctcgtgt ctcc                                              24

<210> SEQ ID NO 40
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 40
acgaagccca ggtaccagaa agag                                              24

<210> SEQ ID NO 41
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 41
aaaagcgccg cagccaagag tagg                                              24

<210> SEQ ID NO 42
<211> LENGTH: 1293
<212> TYPE: DNA
<213> ORGANISM: Homo sapiens

<400> SEQUENCE: 42
ctggagaggc ttgtggggcc tcaggacgct acccactgct ctccgggcct ctcctgccgc       60
ctctgggaca gtgacatact ctgcctgcct ggggacatcg tgcctgctcc gggccccgtg      120
ctggcgccta cgcacctgca gacagagctg gtgctgaggt gccagaagga gaccgactgt      180
```

-continued

```
gacctctgtc tgcgtgtggc tgtccacttg gccgtgcatg ggcactggga agagcctgaa      240
gatgaggaaa agtttggagg agcagctgac tcaggggtgg aggagcctag gaatgcctct      300
ctccaggccc aagtcgtgct ctccttccag gcctacccta ctgcccgctg cgtcctgctg      360
gaggtgcaag tgcctgctgc ccttgtgcag tttggtcagt ctgtgggctc tgtggtatat      420
gactgcttcg aggctgccct agggagtgag gtacgaatct ggtcctatac tcagcccagg      480
tacgagaagg aactcaacca cacacagcag ctgcctgccc tgcccggct caacgtgtca       540 gcagatggtg acaacgtgca tctggttctg aatgtctctg aggagcagca cttcggcctc      600
tccctgtact ggaatcaggt ccagggcccc ccaaaacccc ggtggcacaa aaacctgact      660
ggaccgcaga tcattacctt gaaccacaca gacctggttc cctgcctctg tattcaggtg      720
tggcctctgg aacctgactc cgttaggacg aacatctgcc ccttcaggga ggaccccgc       780 gcacaccaga acctctggca agccgcccga ctgcgactgc tgaccctgca gagctggctg      840
ctggacgcac cgtgctcgct gcccgcagaa gcggcactgt gctggcgggc tccgggtggg      900 gaccctgcc agccactggt cccaccgctt tcctgggaga acgtcactgt ggacaaggtt      960
ctcgagttcc cattgctgaa aggccaccct aacctctgtg ttcaggtgaa cagctcggag      1020
aagctgcagc tgcaggagtg cttgtgggct gactccctgg ggcctctcaa agacgatgtg      1080
ctactgttgg agacacgagg cccccaggac aacagatccc tctgtgcctt ggaacccagt      1140
ggctgtactt cactacccag caaagcctcc acgagggcag ctcgccttgg agagtactta      1200
ctacaagacc tgcagtcagg ccagtgtctg cagctatggg acgatgactt gggagcgcta      1260
tgggcctgcc ccatggacaa atacatccac aag                                   1293
```

<210> SEQ ID NO 43
<211> LENGTH: 431
<212> TYPE: PRT
<213> ORGANISM: Homo sapiens

<400> SEQUENCE: 43

```
Leu Glu Arg Leu Val Gly Pro Gln Asp Ala Thr His Cys Ser Pro Gly
 1               5                  10                  15

Leu Ser Cys Arg Leu Trp Asp Ser Asp Ile Leu Cys Leu Pro Gly Asp
             20                  25                  30

Ile Val Pro Ala Pro Gly Pro Val Leu Ala Pro Thr His Leu Gln Thr
         35                  40                  45

Glu Leu Val Leu Arg Cys Gln Lys Glu Thr Asp Cys Asp Leu Cys Leu
     50                  55                  60

Arg Val Ala Val His Leu Ala Val His Gly His Trp Glu Glu Pro Glu
 65                  70                  75                  80

Asp Glu Glu Lys Phe Gly Gly Ala Ala Asp Ser Gly Val Glu Glu Pro
                 85                  90                  95

Arg Asn Ala Ser Leu Gln Ala Gln Val Val Leu Ser Phe Gln Ala Tyr
            100                 105                 110

Pro Thr Ala Arg Cys Val Leu Leu Glu Val Gln Val Pro Ala Ala Leu
        115                 120                 125

Val Gln Phe Gly Gln Ser Val Gly Ser Val Val Tyr Asp Cys Phe Glu
    130                 135                 140

Ala Ala Leu Gly Ser Glu Val Arg Ile Trp Ser Tyr Thr Gln Pro Arg
145                 150                 155                 160

Tyr Glu Lys Glu Leu Asn His Thr Gln Gln Leu Pro Ala Leu Pro Trp
                165                 170                 175

Leu Asn Val Ser Ala Asp Gly Asp Asn Val His Leu Val Leu Asn Val
```

```
            180                 185                 190
Ser Glu Glu Gln His Phe Gly Leu Ser Leu Tyr Trp Asn Gln Val Gln
            195                 200                 205

Gly Pro Pro Lys Pro Arg Trp His Lys Asn Leu Thr Gly Pro Gln Ile
    210                 215                 220

Ile Thr Leu Asn His Thr Asp Leu Val Pro Cys Leu Cys Ile Gln Val
225                 230                 235                 240

Trp Pro Leu Glu Pro Asp Ser Val Arg Thr Asn Ile Cys Pro Phe Arg
                245                 250                 255

Glu Asp Pro Arg Ala His Gln Asn Leu Trp Gln Ala Ala Arg Leu Arg
            260                 265                 270

Leu Leu Thr Leu Gln Ser Trp Leu Leu Asp Ala Pro Cys Ser Leu Pro
        275                 280                 285

Ala Glu Ala Ala Leu Cys Trp Arg Ala Pro Gly Gly Asp Pro Cys Gln
        290                 295                 300

Pro Leu Val Pro Pro Leu Ser Trp Glu Asn Val Thr Val Asp Lys Val
305                 310                 315                 320

Leu Glu Phe Pro Leu Leu Lys Gly His Pro Asn Leu Cys Val Gln Val
                325                 330                 335

Asn Ser Ser Glu Lys Leu Gln Leu Gln Glu Cys Leu Trp Ala Asp Ser
            340                 345                 350

Leu Gly Pro Leu Lys Asp Asp Val Leu Leu Glu Thr Arg Gly Pro
        355                 360                 365

Gln Asp Asn Arg Ser Leu Cys Ala Leu Glu Pro Ser Gly Cys Thr Ser
        370                 375                 380

Leu Pro Ser Lys Ala Ser Thr Arg Ala Ala Arg Leu Gly Glu Tyr Leu
385                 390                 395                 400

Leu Gln Asp Leu Gln Ser Gly Gln Cys Leu Gln Leu Trp Asp Asp Asp
                405                 410                 415

Leu Gly Ala Leu Trp Ala Cys Pro Met Asp Lys Tyr Ile His Lys
        420                 425                 430

<210> SEQ ID NO 44
<211> LENGTH: 699
<212> TYPE: DNA
<213> ORGANISM: Homo sapiens

<400> SEQUENCE: 44
gagcccagag ggcccacaat caagccctgt cctccatgca aatgcccagc acctaacctc      60
ttgggtggac catccgtctt catcttccct ccaaagatca aggatgtact catgatctcc     120
ctgagcccca tagtcacatg tgtggtggtg gatgtgagcg aggatgaccc agatgtccag     180
atcagctggt ttgtgaacaa cgtggaagta cacacagctc agacacaaac ccatagagag     240
gattacaaca gtactctccg ggtggtcagt gccctcccca tccagcacca ggactggatg     300
agtggcaagg agttcaaatg caaggtcaac aacaaagacc tcccagcgcc catcgagaga     360
accatctcaa acccaaaggt cagtaagaga gctccacagg tatatgtctt gcctccacca     420
gaagaagaga tgactaagaa acaggtcact ctgacctgca tggtcacaga cttcatgcct     480
gaagacattt acgtggagtg gaccaacaac gggaaaacag agctaaacta caagaacact     540
gaaccagtcc tggactctga tggttcttac ttcatgtaca gcaagctgag agtggaaaag     600
aagaactggg tggaaagaaa tagctactcc tgttcagtgg tccacgaggg tctgcacaat     660
caccacacga ctaagagctt ctcccggact ccgggtaaa                            699
```

```
<210> SEQ ID NO 45
<211> LENGTH: 233
<212> TYPE: PRT
<213> ORGANISM: Homo sapiens

<400> SEQUENCE: 45

Glu Pro Arg Gly Pro Thr Ile Lys Pro Cys Pro Pro Cys Lys Cys Pro
  1               5                  10                  15

Ala Pro Asn Leu Leu Gly Gly Pro Ser Val Phe Ile Phe Pro Pro Lys
             20                  25                  30

Ile Lys Asp Val Leu Met Ile Ser Leu Ser Pro Ile Val Thr Cys Val
         35                  40                  45

Val Val Asp Val Ser Glu Asp Asp Pro Asp Val Gln Ile Ser Trp Phe
     50                  55                  60

Val Asn Asn Val Glu Val His Thr Ala Gln Thr Gln Thr His Arg Glu
 65                  70                  75                  80

Asp Tyr Asn Ser Thr Leu Arg Val Val Ser Ala Leu Pro Ile Gln His
                 85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230

<210> SEQ ID NO 46
<211> LENGTH: 69
<212> TYPE: DNA
<213> ORGANISM: Artificial Sequence
<220> FEATURE:
<223> OTHER INFORMATION: oligonucleotide primer

<400> SEQUENCE: 46
gtttcgctca gccaggaaat ccatgccgag ttgagacgct tccgtagact ggagaggctt    60
gtggggcct                                                            69

<210> SEQ ID NO 47
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 47
tgtgggccct ctgggctcct tgtggatgta tttgtc                              36

<210> SEQ ID NO 48
```

```
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 48
gacaaataca tccacaagga gcccagaggg cccaca                                36

<210> SEQ ID NO 49
<211> LENGTH: 55
<212> TYPE: DNA
<213> ORGANISM: Artificial Sequence
<220> FEATURE:
<223> OTHER INFORMATION: oligonucleotide primer

<400> SEQUENCE: 49
caaccccaga gctgttttaa ggcgcgcctc tagattattt acccggagtc cggga           55

<210> SEQ ID NO 50
<211> LENGTH: 76
<212> TYPE: DNA
<213> ORGANISM: Artificial Sequence
<220> FEATURE:
<223> OTHER INFORMATION: oligonucleotide primer

<400> SEQUENCE: 50
caaccccaga gctgttttaa ggcgcgcctc tagattattc catgggcatg tattcttcct     60
tgtggatgta tttgtc                                                     76

<210> SEQ ID NO 51
<211> LENGTH: 10
<212> TYPE: PRT
<213> ORGANISM: Artificial Sequence
<220> FEATURE:
<223> OTHER INFORMATION: C-terminal his tag

<400> SEQUENCE: 51

Gly Ser Gly Gly His His His His His His
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: C-terminal FLAG tag

<400> SEQUENCE: 52

Gly Ser Asp Tyr Lys Asp Asp Asp Asp Lys
 1               5                  10

<210> SEQ ID NO 53
<211> LENGTH: 7
<212> TYPE: PRT
<213> ORGANISM: Artificial Sequence
<220> FEATURE:
<223> OTHER INFORMATION: Glu-Glu tag

<400> SEQUENCE: 53

Glu Glu Tyr Met Pro Met Glu
 1               5

<210> SEQ ID NO 54
<211> LENGTH: 85
<212> TYPE: DNA
<213> ORGANISM: Artificial Sequence
```

```
<220> FEATURE:
<223> OTHER INFORMATION: oligonucleotide primer

<400> SEQUENCE: 54
caaccccaga gctgttttaa ggcgcgcctc tagattagtg atggtgatgg tgatgtccac    60
cagatccctt gtggatgtat ttgtc                                          85

<210> SEQ ID NO 55
<211> LENGTH: 85
<212> TYPE: DNA
<213> ORGANISM: Artificial Sequence
<220> FEATURE:
<223> OTHER INFORMATION: oligonucleotide primer

<400> SEQUENCE: 55
caaccccaga gctgttttaa ggcgcgcctc tagattactt atcatcatca tccttataat    60
cggatccctt gtggatgtat ttgtc                                          85

<210> SEQ ID NO 56
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 56
acgaagccca ggtaccagaa agag                                           24

<210> SEQ ID NO 57
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 57
aaaagcgccg cagccaagag tagg                                           24

<210> SEQ ID NO 58
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 58
cgtaagcggt ggcggttttc                                                20

<210> SEQ ID NO 59
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 59
tgggcagggc acagtcacag                                                20

<210> SEQ ID NO 60
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 60
```

```
acttgccatt ctgagggagg tagc                                           24

<210> SEQ ID NO 61
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 61
cacaggtgca gccaactttt agga                                           24

<210> SEQ ID NO 62
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 62
gtgggccgct ctaggcacca                                                20

<210> SEQ ID NO 63
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 63
cggttggcct tagggttcag ggggg                                          25

<210> SEQ ID NO 64
<211> LENGTH: 2127
<212> TYPE: DNA
<213> ORGANISM: Homo sapiens

<400> SEQUENCE: 64
atggatgcaa tgaagagagg gctctgctgt gtgctgctgc tgtgtggcgc cgtcttcgtt     60
tcgctcagcc aggaaatcca tgccgagttg agacgcttcc gtagactgga gaggcttgtg    120
gggcctcagg acgctaccca ctgctctccg ggcctctcct gccgcctctg ggacagtgac    180
atactctgcc tgcctgggga catcgtgcct gctccgggcc ccgtgctggc gcctacgcac    240
ctgcagacag agctggtgct gaggtgccag aaggagaccg actgtgacct ctgtctgcgt    300
gtggctgtcc acttggccgt gcatgggcac tgggaagagc ctgaagatga ggaaaagttt    360
ggaggagcag ctgactcagg ggtggaggag cctaggaatg cctctctcca ggcccaagtc    420
gtgctctcct tccaggccta ccctactgcc cgctgcgtcc tgctggaggt gcaagtgcct    480
gctgcccttg tgcagtttgg tcagtctgtg ggctctgtgg tatatgactg cttcgaggct    540
gccctaggga gtgaggtacg aatctggtcc tatactcagc ccaggtacga aaggaactc    600 aaccacacac agcagctgcc tgccctgccc tggctcaacg tgtcagcaga tggtgacaac    660
gtgcatctgg ttctgaatgt ctctgaggag cagcacttcg gcctctccct gtactggaat    720
caggtccagg gccccccaaa acccggtgg cacaaaaacc tgactggacc gcagatcatt    780
accttgaacc acacagacct ggttccctgc ctctgtattc aggtgtggcc tctgaacct    840 gactccgtta ggacgaacat ctgccccttc agggaggacc cccgcgcaca ccagaacctc    900
tggcaagccg cccgactgcg actgctgacc ctgcagagct ggctgctgga cgcaccgtgc    960
tcgctgcccg cagaagcggc actgtgctgg cgggctccgg gtggggaccc ctgccagcca   1020
```

```
ctggtcccac cgctttcctg ggagaacgtc actgtggaca aggttctcga gttcccattg   1080
ctgaaaggcc accctaacct ctgtgttcag gtgaacagct cggagaagct gcagctgcag   1140
gagtgcttgt gggctgactc cctggggcct ctcaaagacg atgtgctact gttggagaca   1200
cgaggccccc aggacaacag atccctctgt gccttggaac ccagtggctg tacttcacta   1260
cccagcaaag cctccacgag ggcagctcgc cttggagagt acttactaca agacctgcag   1320
tcaggccagt gtctgcagct atgggacgat gacttgggag cgctatgggc ctgccccatg   1380
gacaaataca tccacaaggg aggaagtggc ggaggaacag aagtttggt ccctcgtgga    1440 agcgacaaaa ctcacacatg cccaccgtgc ccagcacctg aactcctggg gggaccgtca   1500
gtcttcctct tccccccaaa acccaaggac accctcatga tctcccggac ccctgaggtc   1560
acatgcgtgg tggtggacgt gagccacgaa gaccctgagg tcaagttcaa ctggtacgtg   1620
gacggcgtgg aggtgcataa tgccaagaca aagccgcggg aggagcagta caacagcacg   1680
taccgtgtgg tcagcgtcct caccgtcctg caccaggact ggctgaatgg caaggagtac   1740
aagtgcaagg tctccaacaa agccctccca gcccccatcg agaaaaccat ctccaaagcc   1800
aaagggcagc cccgagaacc acaggtgtac accctgcccc catcccggga tgagctgacc   1860
aagaaccagg tcagcctgac ctgcctggtc aaaggcttct atcccagcga catcgccgtg   1920
gagtgggaga gcaatgggca gccggagaac aactacaaga ccacgcctcc cgtgctggac   1980
tccgacggct ccttcttcct ctacagcaag ctcaccgtgg acaagagcag gtggcagcag   2040
gggaacgtct tctcatgctc cgtgatgcat gaggctctgc acaaccacta cacgcagaag   2100
agcctctccc tgtctccggg taaataa                                      2127

<210> SEQ ID NO 65
<211> LENGTH: 708
<212> TYPE: PRT
<213> ORGANISM: Homo sapiens

<400> SEQUENCE: 65

Met Asp Ala Met Lys Arg Gly Leu Cys Cys Val Leu Leu Cys Gly
 1               5                  10                  15

Ala Val Phe Val Ser Leu Ser Gln Glu Ile His Ala Glu Leu Arg Arg
                20                  25                  30

Phe Arg Arg Leu Glu Arg Leu Val Gly Pro Gln Asp Ala Thr His Cys
            35                  40                  45

Ser Pro Gly Leu Ser Cys Arg Leu Trp Asp Ser Asp Ile Leu Cys Leu
        50                  55                  60

Pro Gly Asp Ile Val Pro Ala Pro Gly Pro Val Leu Ala Pro Thr His
65                  70                  75                  80

Leu Gln Thr Glu Leu Val Leu Arg Cys Gln Lys Glu Thr Asp Cys Asp
                85                  90                  95

Leu Cys Leu Arg Val Ala Val His Leu Ala Val His Gly His Trp Glu
            100                 105                 110

Glu Pro Glu Asp Glu Glu Lys Phe Gly Gly Ala Ala Asp Ser Gly Val
        115                 120                 125

Glu Glu Pro Arg Asn Ala Ser Leu Gln Ala Gln Val Val Leu Ser Phe
    130                 135                 140

Gln Ala Tyr Pro Thr Ala Arg Cys Val Leu Leu Glu Val Gln Val Pro
145                 150                 155                 160

Ala Ala Leu Val Gln Phe Gly Gln Ser Val Gly Ser Val Val Tyr Asp
                165                 170                 175
```

```
Cys Phe Glu Ala Ala Leu Gly Ser Glu Val Arg Ile Trp Ser Tyr Thr
            180                 185                 190

Gln Pro Arg Tyr Glu Lys Glu Leu Asn His Thr Gln Gln Leu Pro Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp Lys Val Leu Glu Phe Pro Leu Leu Lys Gly His Pro Asn Leu Cys
        355                 360                 365

Val Gln Val Asn Ser Ser Glu Lys Leu Gln Leu Gln Glu Cys Leu Trp
    370                 375                 380

Ala Asp Ser Leu Gly Pro Leu Lys Asp Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
            420                 425                 430

Glu Tyr Leu Leu Gln Asp Leu Gln Ser Gly Gln Cys Leu Gln Leu Trp
        435                 440                 445

Asp Asp Asp Leu Gly Ala Leu Trp Ala Cys Pro Met Asp Lys Tyr Ile
    450                 455                 460

His Lys Gly Gly Ser Gly Gly Thr Gly Ser Leu Val Pro Arg Gly
465                 470                 475                 480

Ser Asp Lys Thr His Thr Cys Pro Pro Cys Pro Ala Pro Glu Leu Leu
                485                 490                 495

Gly Gly Pro Ser Val Phe Leu Phe Pro Pro Lys Pro Lys Asp Thr Leu
            500                 505                 510

Met Ile Ser Arg Thr Pro Glu Val Thr Cys Val Val Val Asp Val Ser
        515                 520                 525

His Glu Asp Pro Glu Val Lys Phe Asn Trp Tyr Val Asp Gly Val Glu
    530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605
```

```
Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
                660                 665                 670

Val Asp Lys Ser Arg Trp Gln Gln Gly Asn Val Phe Ser Cys Ser Val
            675                 680                 685

Met His Glu Ala Leu His Asn His Tyr Thr Gln Lys Ser Leu Ser Leu
690                 695                 700

Ser Pro Gly Lys
705

<210> SEQ ID NO 66
<211> LENGTH: 1416
<212> TYPE: DNA
<213> ORGANISM: Artificial Sequence
<220> FEATURE:
<223> OTHER INFORMATION: synthetic insert

<400> SEQUENCE: 66
agccaggaaa tccatgccga gttgagacgc ttccgtagac tggagaggct tgtggggcct      60
caggacgcta cccactgctc tccgggcctc tcctgccgcc tctgggacag tgacatactc     120
tgcctgcctg gggacatcgt gcctgctccg ggccccgtgc tggcgcctac gcacctgcag     180
acagagctgg tgctgaggtg ccagaaggag accgactgtg acctctgtct gcgtgtggct     240
gtccacttgg ccgtgcatgg gcactgggaa gagcctgaag atgaggaaaa gtttggagga     300
gcagctgact caggggtgga ggagcctagg aatgcctctc tccaggccca agtcgtgctc     360
tccttccagg cctaccctac tgcccgctgc gtcctgctgg aggtgcaagt gcctgctgcc     420
cttgtgcagt ttggtcagtc tgtgggctct gtggtatatg actgcttcga ggctgcccta     480
gggagtgagg tacgaatctg gtcctatact cagcccaggt acgagaagga actcaaccac     540
acacagcagc tgcctgccct gccctggctc aacgtgtcag cagatggtga caacgtgcat     600
ctggttctga atgtctctga ggagcagcac ttcggcctct ccctgtactg gaatcaggtc     660
cagggccccc caaaaccccg gtggcacaaa aacctgactg gaccgcagat cattaccttg     720
aaccacacag acctggttcc ctgcctctgt attcaggtgt ggcctctgga acctgactcc     780
gttaggacga acatctgccc cttcagggag gaccccgcg cacaccagaa cctctggcaa     840
gccgcccgac tgcgactgct gaccctgcag agctggctgc tggacgcacc gtgctcgctg     900
cccgcagaag cggcactgtg ctggcgggct ccgggtgggg acccctgcca gccactggtc     960
ccaccgcttt cctgggagaa cgtcactgtg acaaggttc tcgagttccc attgctgaaa    1020
ggccacccta acctctgtgt tcaggtgaac agctcggaga gctgcagct gcaggagtgc    1080 ttgtgggctg actccctggg gcctctcaaa gacgatgtgc tactgttgga cacgcaggc    1140 cccccaggaca acagatccct ctgtgccttg aacccagtg gctgtacttc actacccagc    1200
aaagcctcca cgagggcagc tcgccttgga gagtacttac tacaagacct gcagtcaggc    1260
cagtgtctgc agctatggga cgatgacttg ggagcgctat gggcctgccc catggacaaa    1320
tacatccaca aggaggaag tggcggagga acaggaagtt tggtccctcg tggaagcgac    1380
aaaactcaca catgcccacc gtgcccagca cctgaa                              1416
```